(12) United States Patent
Iwai et al.

(10) Patent No.: US 7,488,568 B2
(45) Date of Patent: Feb. 10, 2009

(54) RESIST COMPOSITION, METHOD OF FORMING RESIST PATTERN, COMPOUND AND ACID GENERATOR

(75) Inventors: Takeshi Iwai, Kawasaki (JP); Hideo Hada, Kawasaki (JP); Masaru Takeshita, Kawasaki (JP); Akiya Kawaue, Kawasaki (JP); Keita Ishiduka, Kawasaki (JP); Hiroaki Shimizu, Kawasaki (JP); Kyoko Ohshita, Kawasaki (JP); Tsuyoshi Nakamura, Kawasaki (JP); Komei Hirahara, Kawasaki (JP); Yuichi Suzuki, Kawasaki (JP); Takehiro Seshimo, Kawasaki (JP); Kensuke Matsuzawa, Kawasaki (JP)

(73) Assignee: Tokyo Ohka Kogyo Co., Ltd., Kawasaki-shi (JP)

( * ) Notice: Subject to any disclaimer, the term of this patent is extended or adjusted under 35 U.S.C. 154(b) by 0 days.

(21) Appl. No.: 12/060,695

(22) Filed: Apr. 1, 2008

(65) Prior Publication Data
US 2008/0248422 A1    Oct. 9, 2008

(51) Int. Cl.
G03F 7/004 (2006.01)
G03F 7/30 (2006.01)
C07D 333/46 (2006.01)

(52) U.S. Cl. .................. 430/270.1; 430/326; 430/905; 430/910; 430/922

(58) Field of Classification Search ............ 430/270.1, 430/326, 905, 922; 549/23, 43
See application file for complete search history.

(56) References Cited

U.S. PATENT DOCUMENTS

| 5,908,730 | A | 6/1999 | Nitta et al. | |
|---|---|---|---|---|
| 5,945,517 | A | 8/1999 | Nitta et al. | |
| 6,153,733 | A | 11/2000 | Yukawa et al. | |
| 6,180,313 | B1 | 1/2001 | Yukawa et al. | |
| 7,230,121 | B2* | 6/2007 | Norcini et al. ............... | 549/3 |
| 2004/0110085 | A1 | 6/2004 | Iwai et al. | |
| 2005/0095535 | A1 | 5/2005 | Iwai et al. | |
| 2006/0127806 | A1 | 6/2006 | Iwai et al. | |
| 2006/0127807 | A1 | 6/2006 | Iwai et al. | |
| 2006/0127808 | A1 | 6/2006 | Iwai et al. | |
| 2006/0134552 | A1 | 6/2006 | Iwai et al. | |
| 2006/0134553 | A1 | 6/2006 | Iwai et al. | |
| 2006/0246377 | A1 | 11/2006 | Yamato et al. | |
| 2007/0190455 | A1 | 8/2007 | Iwai et al. | |
| 2007/0224540 | A1* | 9/2007 | Kamimura et al. ....... | 430/270.1 |
| 2007/0275307 | A1* | 11/2007 | Hada et al. .................. | 430/5 |

FOREIGN PATENT DOCUMENTS

| JP | 09-208554 | 8/1997 |
|---|---|---|
| JP | 2005-37888 | 2/2005 |

* cited by examiner

Primary Examiner—John S Chu
(74) Attorney, Agent, or Firm—Knobbe, Martens, Olson & Bear LLP

(57) ABSTRACT

A resist composition including a base component (A) and an acid-generator component (B), the acid-generator component (B) including an acid generator (B1) including a compound represented by general formula (b1-8) shown below (wherein $R^{401}$ represents an acid dissociable, dissolution inhibiting group; $R^{41}$ to $R^{43}$ each independently represents a halogen atom, a halogenated alkyl group, an alkyl group, an acetyl group, an alkoxy group, a carboxy group or a hydroxyalkyl group; Q represents a divalent linking group or a single bond; and $X^-$ represents an anion) or an acid generator (B1') including a compound represented by general formula (b1-9) shown below (wherein $R^{402}$ and $R^{403}$ each independently represents a hydrogen atom, an alkyl group or a halogenated alkyl group; $R^{404}$ represents an alkyl group or a halogenated alkyl group, wherein $R^{403}$ and $R^{404}$ may be bonded to each other to form a ring structure; and $X^-$ represents an anion).

[Chemical Formula 1]

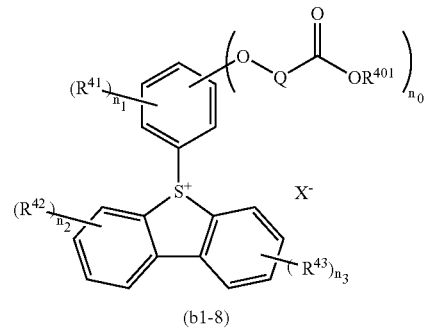

(b1-8)

[Chemical Formula 2]

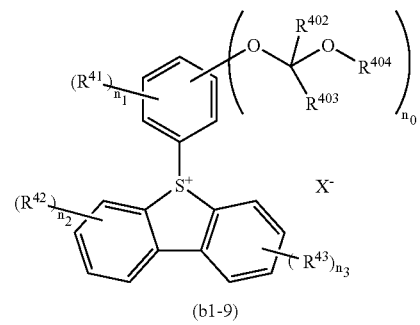

(b1-9)

15 Claims, No Drawings

US 7,488,568 B2

RESIST COMPOSITION, METHOD OF FORMING RESIST PATTERN, COMPOUND AND ACID GENERATOR

TECHNICAL FIELD

The present invention relates to a resist composition, a method of forming a resist pattern using the resist composition, a novel compound useful as an acid generator for the resist composition, and the acid generator.

Priority is claimed on Japanese Patent Application No. 2007-101926, filed Apr. 9, 2007, Japanese Patent Application No. 2007-135427, filed May 22, 2007, and Japanese Patent Application No. 2007-306388, filed Nov. 27, 2007, the contents of which are incorporated herein by reference.

BACKGROUND ART

In lithography techniques, for example, a resist film composed of a resist material is formed on a substrate, and the resist film is subjected to selective exposure of radial rays such as light or electron beam through a mask having a predetermined pattern, followed by development, thereby forming a resist pattern having a predetermined shape on the resist film. A resist material in which the exposed portions become soluble in a developing solution is called a positive-type, and a resist material in which the exposed portions become insoluble in a developing solution is called a negative-type.

In recent years, in the production of semiconductor elements and liquid crystal display elements, advances in lithography techniques have lead to rapid progress in the field of pattern miniaturization.

Typically, these miniaturization techniques involve shortening the wavelength of the exposure light source. Conventionally, ultraviolet radiation typified by g-line and i-line radiation has been used, but nowadays KrF excimer lasers and ArF excimer lasers are now starting to be introduced in mass production. Furthermore, research is also being conducted into lithography techniques that use exposure light source having a wavelength shorter than these excimer lasers, such as $F_2$ excimer lasers, electron beam, extreme ultraviolet radiation (EV), and X ray.

Resist materials for use with these types of exposure light sources require lithography properties such as a high resolution capable of reproducing patterns of minute dimensions, and a high level of sensitivity to these types of exposure light sources. As a resist material which satisfies these conditions, a chemically amplified resist is used, which includes a base resin that exhibits a changed solubility in an alkali developing solution under action of acid and an acid generator that generates acid upon exposure. For example, a chemically amplified positive resist contains, as a base resin, a resin which exhibits increased solubility in an alkali developing solution under action of acid, and an acid generator. In the formation of a resist pattern, when acid is generated from the acid generator upon exposure, the exposed portions become alkali soluble.

Until recently, polyhydroxystyrene (PHS) or derivative resins thereof in which the hydroxyl groups are protected with acid-dissociable, dissolution-inhibiting groups (PHS-based resins), which exhibit high transparency to a KrF excimer laser (248 nm), have been used as the base resin component of chemically amplified resists. However, because PHS-based resins contain aromatic rings such as benzene rings, their transparency is inadequate for light with wavelengths shorter than 248 nm, such as light of 193 nm. Accordingly, chemically amplified resists that use a PHS-based resin as the base resin component suffer from low levels of resolution in processes that use light of 193 nm.

As a result, resins that contain structural units derived from (meth)acrylate esters within the main chain (acrylic resins) are now widely used as base resins for resists that use ArF excimer laser lithography, as they exhibit excellent transparency in the vicinity of 193 nm. In the case of a positive resist, as the base resin, those which have a structural unit derived from (meth)acrylate ester including an aliphatic polycyclic group-containing, tertiary alkyl ester-type acid dissociable, dissolution inhibiting group, such as a structural unit derived from 2-alkyl-2-adamantyl(meth)acrylate are mainly used (for example, see Patent Document 1).

Here, the term "(meth)acrylate ester" is a generic term that includes either or both of the acrylate ester having a hydrogen atom bonded to the α-position and the methacrylate ester having a methyl group bonded to the α-position. The term "(meth)acrylate" is a generic term that includes either or both of the acrylate having a hydrogen atom bonded to the α-position and the methacrylate having a methyl group bonded to the α-position. The term "(meth)acrylic acid" is a generic term that includes either or both of acrylic acid having a hydrogen atom bonded to the α-position and methacrylic acid having a methyl group bonded to the α-position.

On the other hand, as acid generators usable in a chemically amplified resist, various types have been proposed including, for example, onium salt-based acid generators such as iodonium salts and sulfonium salts; oxime sulfonate-based acid generators; diazomethane-based acid generators; nitrobenzylsulfonate-based acid generators; iminosulfonate-based acid generators; and disulfone-based acid generators. Currently, as acid generators, those which include a triphenylsulfonium skeleton, dinaphthyl monophenylsulfonium skeleton, or the like are used (for example, see Patent Document 2).

[Patent Document 1] Japanese Unexamined Patent Application, First Publication No. 2003-241385

[Patent Document 2] Japanese Unexamined Patent Application, First Publication No. 2005-37888

DISCLOSURE OF INVENTION

Means to Solve the Problems

In recent years, as requirements for high resolution increase with progress in the miniaturization of resist patterns, improvement in various lithography properties has been demanded.

As an example of such lithography properties, line width roughness (hereafter, frequently abbreviated as "LWR") can be mentioned. LWR is a phenomenon in which the line width of a line pattern becomes heterogeneous when a resist pattern is formed using a resist composition, and improvement in the level of LWR becomes an important issue as pattern miniaturization progresses.

Further, as the cation for onium salt-based acid generators, highly hydrophobic cations such as triphenylsulfonium and dinaphthyl monophenylsulfonium have typically been used. However, onium salt-based acid generators having such a cation had a problem in that the solubility thereof was low in an organic solvent (resist solvent) for dissolving various components of a resist. Such low solubility in a resist solvent lowers the post exposure stability of the latent image formed by the pattern-wise exposure of the resist, thereby causing deterioration of the resist pattern shape. Furthermore, such onium salt-based acid generators having a highly hydrophobic cation is disadvantages in that it suppresses dissolution of the resist film in an alkali developing solution during developing at both of exposed portions and unexposed portions.

The present invention takes the above circumstances into consideration, with an object of providing a novel compound preferable as an acid generator for a resist composition, an acid generator including the compound, a resist composition containing the acid generator, and a method of forming a resist pattern using the resist composition.

Means to Solve the Problems

For solving the above-mentioned problems, the present inventors propose the following aspects.

Specifically, a first aspect of the present invention is a resist composition including a base component (A) which exhibits changed solubility in an alkali developing solution under action of acid and an acid-generator component (B) which generates acid upon irradiation, the acid-generator component (B) including an acid generator (B1) including a compound represented by general formula (b1-8) shown below or an acid generator (B1') including a compound represented by general formula (b1-9) shown below:

[Chemical Formula 1]

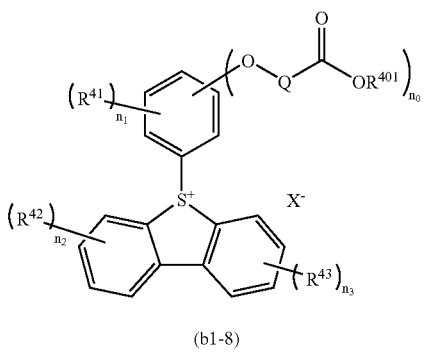

(b1-8)

wherein $R^{401}$ represents an acid dissociable, dissolution inhibiting group; $R^{41}$ to $R^{43}$ each independently represents a halogen atom, a halogenated alkyl group, an alkyl group, an acetyl group, an alkoxy group, a carboxy group or a hydroxyalkyl group; Q represents a divalent linking group or a single bond; $n_0$ represents an integer of 1 to 3, and $n_1$ to $n_3$ each independently represents an integer of 0 to 3, with the proviso that $n_0+n_1$ is 5 or less; and $X^-$ represents an anion;

[Chemical Formula 2]

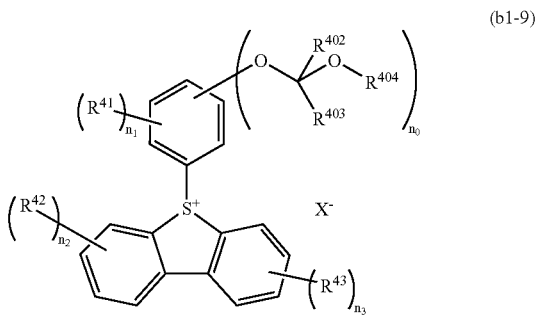

(b1-9)

wherein $R^{41}$ to $R^{43}$ each independently represents a halogen atom, a halogenated alkyl group, an alkyl group, an acetyl group, an alkoxy group, a carboxy group or a hydroxyalkyl group; $R^{402}$ and $R^{403}$ each independently represents a hydrogen atom, an allyl group or a halogenated alkyl group; $R^{404}$ represents an alkyl group or a halogenated alkyl group, wherein $R^{403}$ and $R^{404}$ may be bonded to each other to form a ring structure; $n_0$ represents an integer of 1 to 3, and $n_1$ to $n_3$ each independently represents an integer of 0 to 3, with the proviso that $n_0+n_1$ is 5 or less; and $X^-$ represents an anion.

Further, a second aspect of the present invention is a method of forming a resist pattern, including: applying a resist composition of the above-mentioned first aspect of the present invention to a substrate to form a resist film on the substrate; conducting exposure of the resist film; and alkali-developing the resist film to form a resist pattern.

Furthermore, a third aspect of the present invention is a compound represented by general formula (b1-8) shown above.

Still further, a fourth aspect of the present invention is an acid generator including the compound represented by general formula (b1-8) shown above.

Still further, a fifth aspect of the present invention is a compound represented by general formula (b1-9) shown above.

Still further, a sixth aspect of the present invention is an acid generator including the compound represented by general formula (b1-9) shown above.

In the present description and claims, the term "structural unit" refers to a monomer unit that contributes to the formation of a resin component (polymer).

The term "exposure" is used as a general concept that includes irradiation with any form of radiation.

The term "acid dissociable, dissolution inhibiting group" refers to an organic group which can be dissociated by action of acid.

The term "aliphatic cyclic group" refers to a monocyclic group or polycyclic group that has no aromaticity.

An "alkyl group" includes linear, branched or cyclic, monovalent saturated hydrocarbon, unless otherwise specified.

A "lower alkyl group" is an alkyl group of 1 to 5 carbon atoms.

EFFECT OF THE INVENTION

According to the present invention, there are provided a novel compound preferable as an acid generator for a resist composition, an acid generator including the compound, a resist composition containing the acid generator, and a method of forming a resist pattern using the resist composition.

BEST MODE FOR CARRYING OUT THE INVENTION

<<Compound of Third Aspect>>

First, the compound of the third aspect of the present invention will be described. The compound of the third aspect of the present invention is represented by general formula (b1-8) shown above.

In general formula (b1-8) above, $R^{401}$ represents an acid dissociable, dissolution inhibiting group, and $R^{41}$, $R^{42}$ and $R^{43}$ each independently represents a halogen atom, a halogenated alkyl group, an alkyl group, an acetyl group, an alkoxy group, a carboxy group or a hydroxyalkyl group.

As the acid dissociable, dissolution inhibiting group for $R^{401}$, there is no particular limitation as long as it is an organic group which can be dissociated by action of acid. Examples of acid dissociable, dissolution inhibiting groups include cyclic or linear tertiary alkyl ester-type acid dissociable, dissolution inhibiting groups and acetal-type acid dissociable, dissolution inhibiting groups such as alkoxyalkyl groups. Among these, tertiary alkyl ester-type acid dissociable, dissolution inhibiting groups are preferable.

$R^{401}$ is preferably an acid dissociable, dissolution inhibiting group represented by general formula (b1-8-0) shown below.

[Chemical Formula 3]

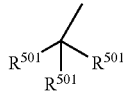

(b1-8-0)

wherein the plurality of $R^{501}$ may be the same or different, and at least one $R^{501}$ represents a linear or branched alkyl group of 1 to 4 carbon atoms; and the remaining two $R^{501}$ each independently represents a linear or branched alkyl group of 1 to 4 carbon atoms or a monovalent aliphatic cyclic group of 4 to 20 carbon atoms, or the remaining two $R^{501}$ may be bonded to each other to form a divalent aliphatic cyclic group of 4 to 20 carbon atoms including the carbon atom to which the two $R^{501}$ are bonded.

As aliphatic cyclic groups, groups in which one or more hydrogen atoms have been removed from a monocycloalkane or a polycycloalkane such as a bicycloalkane, tricycloalkane or tetracycloalkane may be exemplified. Specific examples include groups in which one or more hydrogen atoms have been removed from a monocycloalkane such as cyclopentane and cyclohexane; and groups in which one or more hydrogen atoms have been removed from a polycycloalkane such as adamantane, norbornane, isobornane, tricyclodecane or tetracyclododecane. More specific examples include a cyclopentyl group, a cyclohexyl group, a norbornyl group and an adamantyl group.

As linear or branched alkyl groups of 1 to 4 carbon atoms, a methyl group, an ethyl group, a propyl group, an isopropyl group, an n-butyl group, an isobutyl group and a tert-butyl group may be exemplified.

As the acid dissociable, dissolution inhibiting group represented by general formula (b1-8-0) above, examples of those in which the plurality of $R^{501}$ each independently represents a linear or branched alkyl group of 1 to 4 carbon atoms include a tert-butyl group, a tert-pentyl group and a tert-hexyl group.

As the acid dissociable, dissolution inhibiting group represented by general formula (b1-8-0) above, examples of those in which at least one $R^{501}$ represents a linear or branched alkyl group of 1 to 4 carbon atoms and the remaining two $R^{501}$ each independently represents a linear or branched alkyl group of 1 to 4 carbon atoms or a monovalent aliphatic cyclic group of 4 to 20 carbon atoms include a 1-(1-adamantyl)-1-methylethyl group, a 1-(1-adamantyl)-methylpropyl group, a 1-(1-adamantyl)-methylbutyl group, a 1-(1-adamantyl)-methylpentyl group, a 1-(1-cyclopentyl)-1-methyethyl group, a 1-(1-cyclopentyl)-1-methypropyl group, a 1-(1-cyclopentyl)-1-methybutyl group, a 1-(1-cyclopentyl)-1-methypentyl group, a 1-(1-cyclohexyl)-1-methyethyl group, a 1-(1-cyclohexyl)-1-methypropyl group, a 1-(1-cyclohexyl)-1-methybutyl group and a 1-(1-cyclohexyl)-1-methypentyl group.

As the acid dissociable, dissolution inhibiting group represented by general formula (b1-8-0) above, examples of those in which one $R^{501}$ represents a linear or branched alkyl group of 1 to 4 carbon atoms and the remaining two $R^{501}$ are bonded to each other to form a divalent aliphatic cyclic group of 4 to 20 carbon atoms including the carbon atom to which the two $R^{501}$ are bonded include 2-alkyl-2-adamantyl groups such as a 2-methyl-2-adamantyl group and a 2-ethyl-2-adamantyl group; and 1-alkyl-1-cycloalkyl groups such as a 1-methyl-1-cyclopentyl group, a 1-ethyl-1-cyclopentyl group, a 1-methyl-1-cyclohexyl group and a 1-ethyl-1-cyclohexyl group.

As the acid dissociable, dissolution inhibiting group represented by general formula (b1-8-0) above, among the groups exemplified above, any one of those in which the plurality of $R^{501}$ each independently represents a linear or branched alkyl group of 1 to 4 carbon atoms or any one of those in which one $R^{501}$ represents a linear or branched alkyl group of 1 to 4 carbon atoms and the remaining two $R^{501}$ are bonded to each other to form a divalent aliphatic cyclic group of 4 to 20 carbon atoms including the carbon atom to which the two $R^{501}$ are bonded is preferable, and a tert-butyl group or a 2-methyl-2-adamantyl group is particularly desirable.

With respect to $R^{41}$, $R^{42}$ and $R^{43}$, the alkyl group is preferably a lower alkyl group of 1 to 5 carbon atoms, more preferably a linear or branched alkyl group, still more preferably a methyl group, an ethyl group, a propyl group, an isopropyl group, an n-butyl group, a tert-butyl group, a tert-pentyl group or a tert-pentyl group, and most preferably a methyl group.

The alkoxy group is preferably an alkoxy group of 1 to 5 carbon atoms, more preferably a linear or branched alkoxy group, and most preferably a methoxy group or an ethoxy group.

The hydroxyalkyl group is preferably any one of the above-exemplified alkyl groups in which one or more hydrogen atoms have been substituted with hydroxy groups. Specific examples include a hydroxymethyl group, a hydroxyethyl group and a hydroxypropyl group.

Examples of halogen atoms include a fluorine atom, a chlorine atom, a bromine atom and an iodine atom, and a fluorine atom is preferable.

The halogenated alkyl group is preferably a halogenated alkyl group of 1 to 5 carbon atoms, more preferably a halogenated alkyl group of 1 to 5 carbon atoms which have been substituted with fluorine atoms, and most preferably a trifluoromethyl group or a pentafluoroethyl group.

$n_0$ represents an integer of 1 to 3, preferably 1 or 2, and more preferably 1.

$n_1$ represents an integer of 0 to 3, preferably 1 or 2, and more preferably 2.

$n_2$ and $n_3$ each independently represents an integer of 0 to 3, preferably 0 or 1, and more preferably 0.

However, $n_0+n_1$ is 5 or less.

In general formula (b1-8) above, Q represents a divalent linking group or a single bond.

Examples of divalent linking groups include linear, branched or cyclic alkylene groups of 1 to 8 carbon atoms, such as a methylene group, an ethylene group, a propylene group, an isopropylene group, a cyclopropylene group, an n-butylene group, an isobutylene group, a cyclopentylene group, a cyclohexylene group, a cycloheptylene group and a cyclooctylene group. Further, the divalent linking group for Q may contain an oxygen atom. Examples of such divalent linking groups containing an oxygen atom include ether groups and ester groups. Among these, in consideration of ease in synthesizing, linear alkylene groups are preferable, and a methylene group is particularly desirable.

In general formula (b1-8) above, $X^-$ represents an anion. As the anion moiety of $X^-$, there is no particular limitation, and any anion moiety can be appropriately used which is known as an anion moiety of an onium salt-based acid generator. For example, an anion represented by general formula: $R^{14}SO_3^-$ (wherein $R^{14}$ represents a linear, branched or cyclic alkyl group, a halogenated alkyl group, an aryl group or an alkenyl group) or an anion represented by general formula: $R^1$—O—$Y^1$—$SO_3^-$ (wherein $R^1$ represents a monovalent aliphatic hydrocarbon group, a monovalent aromatic organic group or a monovalent hydroxyalkyl group; and $Y^1$ represents an alkylene group of 1 to 4 carbon atoms which may be fluorinated) can be used.

In general formula: $R^{14}SO_3^-$ above, $R^{14}$ represents a linear, branched or cyclic alkyl group, a halogenated alkyl group, an aryl group or an alkenyl group.

The linear or branched alkyl group for $R^{14}$ preferably has 1 to 10 carbon atoms, more preferably 1 to 8 carbon atoms, and most preferably 1 to 4 carbon atoms.

The cyclic alkyl group for $R^{14}$ preferably has 4 to 15 carbon atoms, more preferably 4 to 10 carbon atoms, and most preferably 6 to 10 carbon atoms.

As $R^{14}$, a halogenated alkyl group is preferable. That is, in general formula (b1-8) above, it is preferable that $X^-$ be a halogenated alkylsulfonate ion. A halogenated alkyl is an alkyl in which some or all of the hydrogen atoms have been substituted with halogen atoms. As the halogenated alkyl group, the alkyl groups for $R^{41}$, $R^{42}$ and $R^{43}$ which have been substituted with halogen atoms can be exemplified. Examples of halogen atoms include a fluorine atom, a chlorine atom, a bromine atom and an iodine atom. In the halogenated alkyl, it is preferable that 50 to 100% of the hydrogen atoms are substituted with halogen atoms, and it is more preferable that all hydrogen atoms are substituted with halogen atoms.

As the halogenated alkyl group, a fluorinated alkyl group is preferable. The fluorinated alkyl group preferably has 1 to 10 carbon atoms, more preferably 1 to 8 carbon atoms, and most preferably 1 to 4 carbon atoms. The fluorination ratio of the fluorinated alkyl group (percentage of the number of fluorine atoms substituting the hydrogen atoms within the alkyl group, based on the total number of hydrogen atoms within the alkyl group prior to fluorination, and the same applies to the fluorination ratio described below) is preferably from 10 to 100%, more preferably from 50 to 100%, and it is particularly desirable that all of the hydrogen atoms are substituted with fluorine atoms, as the acid strength increases.

The aryl group for $R^{14}$ is preferably an aryl group of 6 to 20 carbon atoms which may have a substituent. Examples of substituents include a halogen atom, a hetero atom and an alkyl group. The aryl group may have a plurality of substituents.

The alkenyl group for $R^{14}$ is preferably an alkenyl group of 2 to 10 carbon atoms which may have a substituent. Examples of substituents include a halogen atom, a hetero atom and an alkyl group. The alkenyl group may have a plurality of substituents.

In general formula $R^1$—O—$Y^1$—$SO_3^-$ above, $R^1$ represents a monovalent aliphatic hydrocarbon group, a monovalent aromatic organic group or a monovalent hydroxyalkyl group; and $Y^1$ represents an alkylene group of 1 to 4 carbon atoms which may be fluorinated.

As the monovalent aliphatic hydrocarbon group for $R^1$, for example, a linear, branched or cyclic, monovalent saturated hydrocarbon group of 1 to 15 carbon atoms, or a linear or branched, monovalent unsaturated hydrocarbon group of 2 to 5 carbon atoms can be mentioned.

Examples of linear, monovalent saturated hydrocarbon groups include a methyl group, ethyl group, propyl group, butyl group, pentyl group, hexyl group, heptyl group, octyl group, nonyl group and decanyl group.

Examples of branched, monovalent saturated hydrocarbon groups include a 1-methylethyl group, 1-methylpropyl group, 2-methylpropyl group, 1-methybutyl group, 2-methylbutyl group, 3-methylbutyl group, 1-ethylbutyl group, 2-ethylbutyl group, 1-methylpentyl group, 2-methylpentyl group, 3-methylpentyl group and 4-methylpentyl group.

The cyclic, monovalent saturated hydrocarbon group may be either a polycyclic group or a monocyclic group. For example, groups in which one hydrogen atom has been removed from a monocycloalkane or a polycycloalkane such as a bicycloalkane, tricycloalkane or tetracycloalkane can be mentioned. Specific examples include groups in which one hydrogen atom has been removed from a monocycloalkane such as cyclopentane, cyclohexane, cycloheptane or cyclooctane; and groups in which one hydrogen atom has been removed from a polycycloalkane such as adamantane, norbornane, isobornane, tricyclodecane or tetracyclododecane.

Examples of linear, monovalent unsaturated hydrocarbon group include propenyl group (allyl group) and butynyl group.

Examples of branched, monovalent unsaturated hydrocarbon group include 1-methylpropenyl group and 2-methylpropenyl group.

The monovalent aliphatic hydrocarbon group for $R^1$ preferably has 3 to 4 carbon atoms, and it is particularly desirable that the monovalent aliphatic hydrocarbon group have 3 carbon atoms.

Examples of monovalent aromatic organic groups for $R^1$ include aryl groups in which one hydrogen atom has been removed from an aromatic hydrocarbon ring, such as a phenyl group, a biphenyl group, a fluorenyl group, a naphthyl group, an anthracyl group, and a phenantryl group; and heteroaryl groups in which some of the carbon atoms constituting the ring(s) of these groups are substituted with hetero atoms such as an oxygen atom, a sulfur atom, and a nitrogen atom. These aryl groups and heteroaryl groups may have a substituent such as an alkyl group of 1 to 10 carbon atoms, a halogenated alkyl group, an alkoxy group, a hydroxyl group or a halogen atom. The alkyl group or halogenated alkyl group as the substituent preferably has 1 to 8 carbon atoms, and more preferably 1 to 4 carbon atoms. The halogenated alkyl group is preferably a fluorinated alkyl group. Examples of halogen atoms include a fluorine atom, a chlorine atom, a bromine atom and an iodine atom, and a fluorine atom is preferable.

The monovalent hydroxyalkyl group for $R^1$ is a linear, branched or cyclic, monovalent saturated hydrocarbon group in which at least one hydrogen atom has been substituted with a hydroxyl group. Linear or branched, monovalent saturated hydrocarbon groups which one or two hydrogen atoms have been substituted with hydroxyl groups are preferable. Specific examples include a 1-hydroxypropyl group, 2-hydroxypropyl group, 3-hydroxypropyl group and 2,3-dihydroxypropyl group.

The monovalent hydroxyalkyl group for $R^1$ preferably has 3 to 10 carbon atoms, more preferably 3 to 8 carbon atoms, and most preferably 3 to 6 carbon atoms.

Examples of alkylene groups of 1 to 4 carbon atoms for $Y^1$ which may be fluorinated include —$CF_2$—, —$CF_2CF_2$—, —$CF_2CF_2CF_2$—, —$CF(CF_3)CF_2$—, —$CF(CF_2CF_3)$—, —$C(CF_3)_2$—, —$CF_2CF_2CF_2CF_2$—, —$CF(CF_3)CF_2CF_2$—, —CF$_2$CF(CF$_3$)CF$_2$—, —CF(CF$_3$(CF(CF$_3$)—, —C(CF$_3$)$_2$CF$_2$—, —CF(CF$_2$CF$_3$)CF$_2$—, —CF(CF$_2$CF$_2$CF$_3$)—, —C(CF$_3$)(CF$_2$CF$_3$)—; —CHF—, —CH$_2$CF$_2$—, —CH$_2$CH$_2$CF$_2$—, —CH$_2$CF$_2$CF$_2$—, —CH(CF$_3$)CH$_2$—, —CH(CF$_2$CF$_3$)—, —C(CH$_3$)(CF$_3$)—, —CH$_2$CH$_2$CH$_2$CF$_2$—, —CH$_2$CH$_2$CF$_2$CF$_2$—, —CH(CF$_3$)CH$_2$CH$_2$—, —CH$_2$CH(CF$_3$)CH$_2$—, —CH(CF$_3$)CH(CF$_3$)—, —C(CF$_3$)$_2$CH$_2$—; —CH$_2$—, —CH$_2$CH$_2$—, —CH$_2$CH$_2$CH$_2$—, —CH(CH$_3$)CH$_2$—, —CH(CH$_2$CH$_3$)—, —C(CH$_3$)$_2$—, —CH$_2$CH$_2$CH$_2$CH$_2$—, —CH(CH$_3$)CH$_2$CH$_2$—, —CH$_2$CH(CH$_3$)CH$_2$—, —CH(CH$_3$)CH(CH$_3$)—, —C(CH$_3$)$_2$CH$_2$—, —CH(CH$_2$CH$_3$)CH$_2$—, —CH(CH$_2$CH$_2$CH$_3$)—, and —C(CH$_3$)(CH$_2$CH$_3$)—.

As the alkylene group of 1 to 4 carbon atoms for Y$^1$ which may be fluorinated, it is preferable that the carbon atom bonded to S be fluorinated. Examples of such fluorinated alkylene groups include —CF$_2$—, —CF$_2$CF$_2$—, —CF$_2$CF$_2$CF$_2$—, —CF(CF$_3$)CF$_2$—, —CF$_2$CF$_2$CF$_2$CF$_2$—, —CF(CF$_3$)CF$_2$CF$_2$—, —CF$_2$CF(CF$_3$)CF$_2$—, —CF(CF$_3$)CF(CF$_3$)—, —C(CF$_3$)$_2$CF$_2$—, —CF(CF$_2$CF$_3$)CF$_2$—; —CH$_2$CF$_2$—, —CH$_2$CH$_2$CF$_2$—, —CH$_2$CF$_2$CF$_2$—; —CH$_2$CH$_2$CH$_2$CF$_2$—, —CH$_2$CH$_2$CF$_2$CF$_2$—, and —CH$_2$CF$_2$CF$_2$CF$_2$—.

Among these, —CF$_2$CF$_2$—, —CF$_2$CF$_2$CF$_2$—, and CH$_2$CF$_2$CF$_2$— are preferable, —CF$_2$CF$_2$— and —CF$_2$CF$_2$CF$_2$— are more preferable, and —CF$_2$CF$_2$— is particularly desirable.

In general formula (b1-8) above, as X$^-$, anions represented by general formula (b-3) shown below and anions represented by general formula (b-4) shown below may be used.

[Chemical Formula 4]

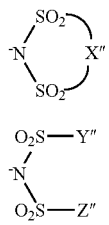

(b-3)

(b-4)

wherein X" represents an alkylene group of 2 to 6 carbon atoms in which at least one hydrogen atom has been substituted with a fluorine atom; and Y" and Z" each independently represents an alkyl group of 1 to 10 carbon atoms in which at least one hydrogen atom has been substituted with a fluorine atom.

In general formula (b-3) above, X" represents a linear or branched alkylene group in which at least one hydrogen atom has been substituted with a fluorine atom, and the alkylene group preferably has 2 to 6 carbon atoms, more preferably 3 to 5 carbon atoms, and most preferably 3 carbon atoms.

In general formula (b-4) above, Y" and Z" each independently represents a linear or branched alkyl group in which at least one hydrogen atom has been substituted with a fluorine atom, and the alkyl group preferably has 1 to 10 carbon atoms, more preferably 1 to 7 carbon atoms, and most preferably 1 to 3 carbon atoms.

The smaller the number of carbon atoms of the alkylene group for X" or those of the alkyl group for Y" and Z" within the above-mentioned range of the number of carbon atoms, the more the solubility in a resist solvent is improved.

Further, in the alkylene group for X" or the alkyl group for Y" and Z", it is preferable that the number of hydrogen atoms substituted with fluorine atoms is as large as possible because the acid strength increases and the transparency to high energy radiation of 200 nm or less or electron beam is improved. The fluorination ratio the alkylene group or alkyl group is preferably from 70 to 100%, more preferably from 90 to 100%, and it is particularly desirable that the alkyene group or alkyl group be a perfluoroalkylene or perfluoroalkyl group in which all hydrogen atoms are substituted with fluorine atoms.

As the compound of the third aspect of the present invention, specific examples of those in which the plurality of R$^{501}$ each independently represents a linear or branched alkyl group of 1 to 4 carbon atoms and Q represents a single bond include compounds represented by formulas (b1-81) to (b1-89) shown below, and specific examples of those in which Q represents a divalent linking group include compounds represented by formulas (b1-121) to (b1-129) shown below.

Further, as the compound of the third aspect of the present invention, specific examples of those in which at least one R$^{501}$ represents a linear or branched alkyl group of 1 to 4 carbon atoms and the remaining two R$^{501}$ each independently represents a linear or branched alkyl group of 1 to 4 carbon atoms or a monovalent aliphatic cyclic group of 4 to 20 carbon atoms, and Q represents a single bond, include compounds represented by formulas (b1-91) to (b1-99) shown below, and specific examples of those in which Q represents a divalent linking group include compounds represented by formulas (b1-131) to (b1-139) shown below.

Furthermore, as the compound of the third aspect of the present invention, specific examples of those in which at least one R$^{501}$ represents a linear or branched alkyl group of 1 to 4 carbon atoms and the remaining two R$^{501}$ are bonded to each other to form a divalent aliphatic cyclic group of 4 to 20 carbon atoms including the carbon atom to which the two R$^{501}$ are bonded, and Q represents a single bond, include compounds represented by formulas (b1-101) to (b1-119) shown below, and specific examples of those in which Q represents a divalent linking group include compounds represented by formulas (b1-141) to (b1-159) shown below.

[Chemical Formula 5]

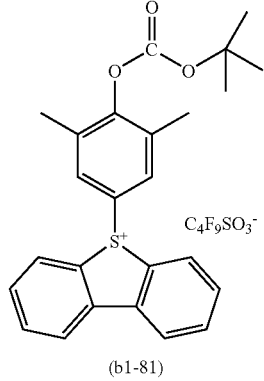

(b1-81)

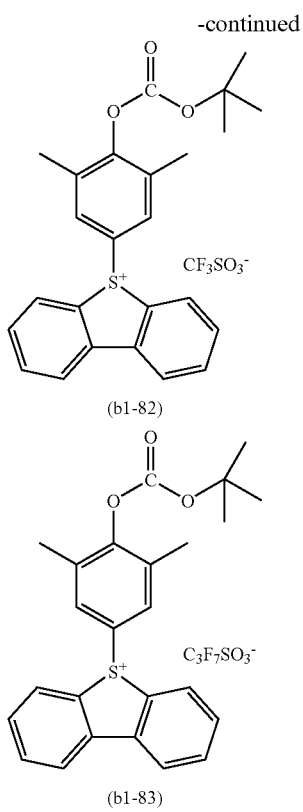
(b1-82)
(b1-83)
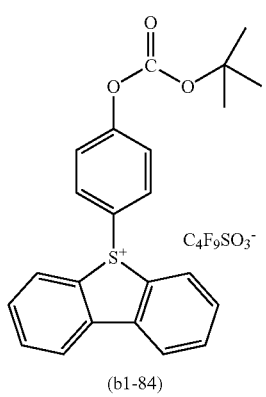
(b1-84)
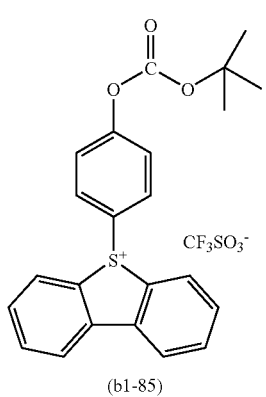
(b1-85)
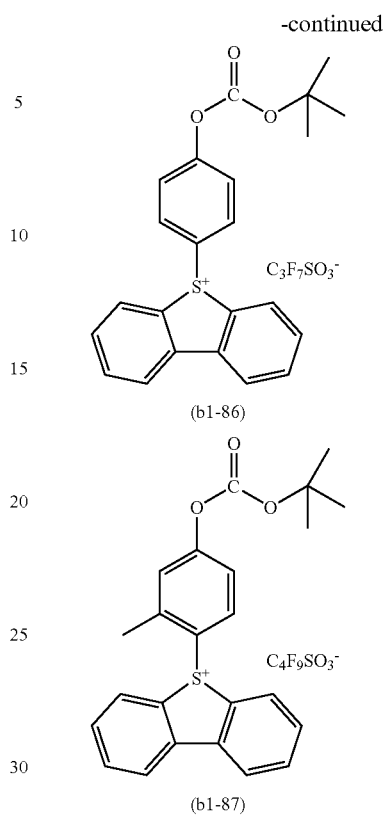
(b1-86)
(b1-87)
[Chemical Formula 6]
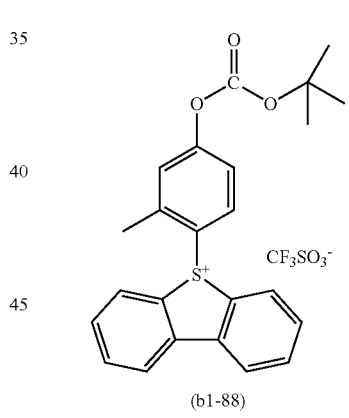
(b1-88)
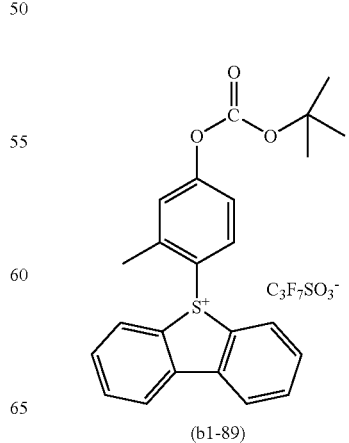
(b1-89)

-continued
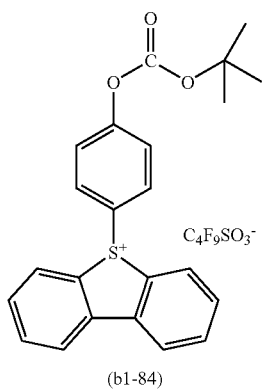
(b1-84)
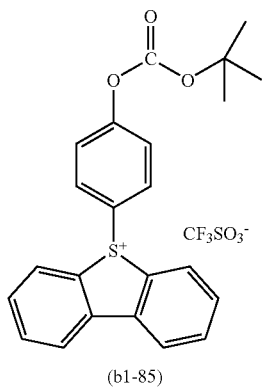
(b1-85)
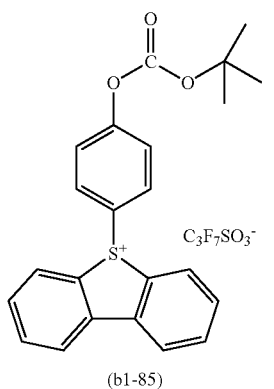
(b1-85)
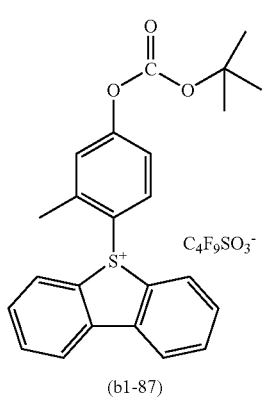
(b1-87)
-continued
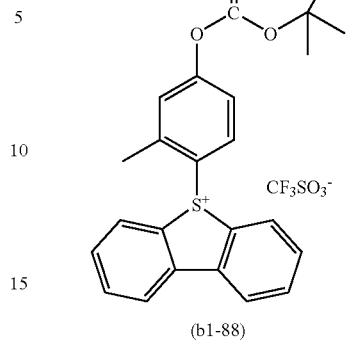
(b1-88)
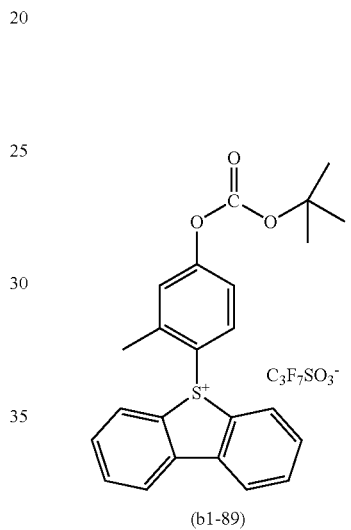
(b1-89)
[Chemical Formula 8]
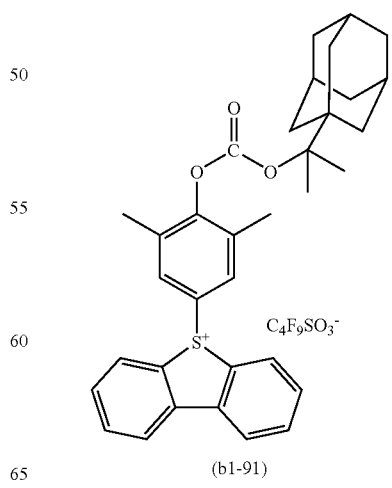
(b1-91)

-continued
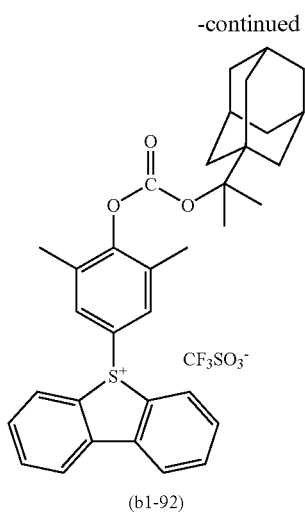
(b1-92)
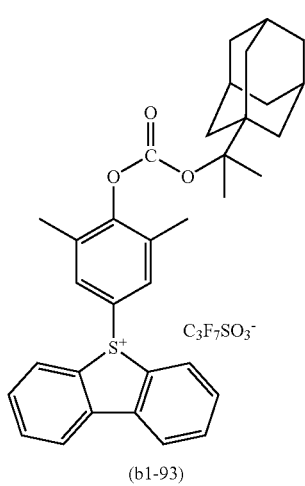
(b1-93)
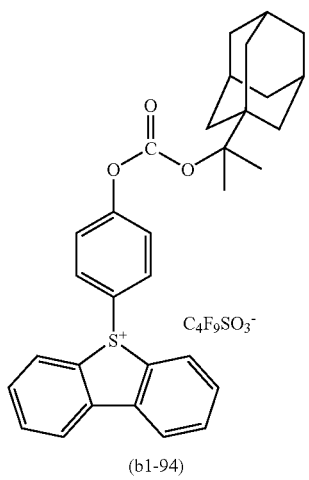
(b1-94)
-continued
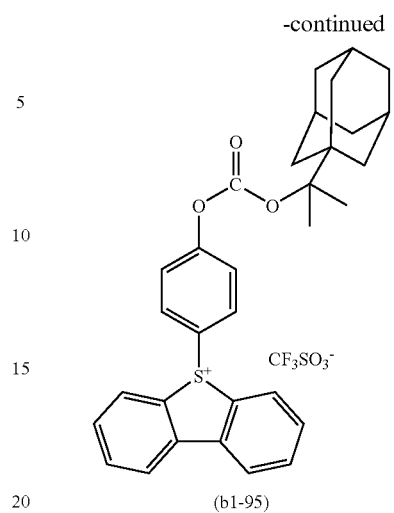
(b1-95)
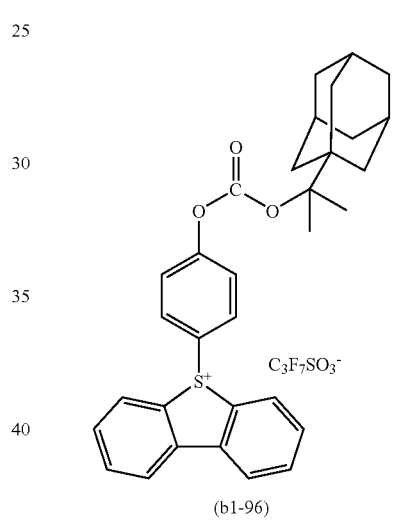
(b1-96)
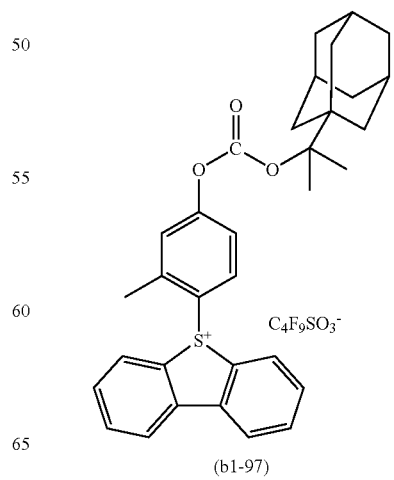
(b1-97)

-continued
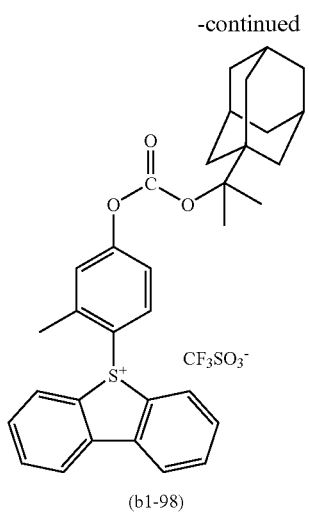
(b1-98)
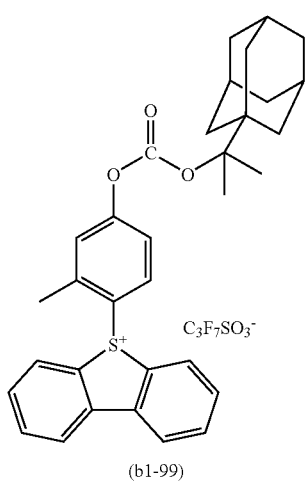
(b1-99)
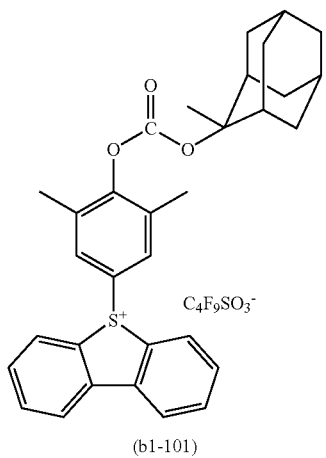
(b1-101)
-continued
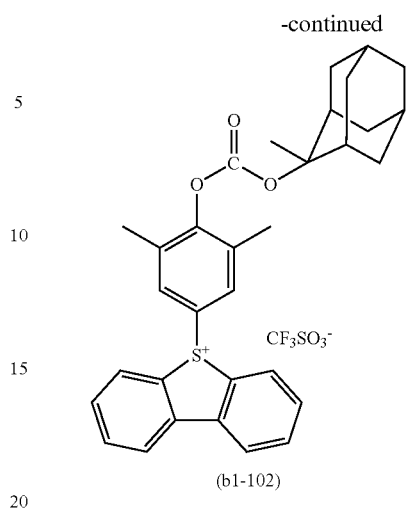
(b1-102)
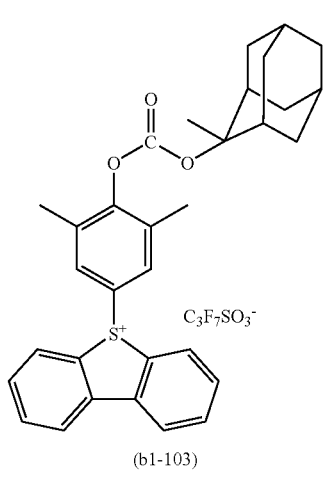
(b1-103)
[Chemical Formula 9]
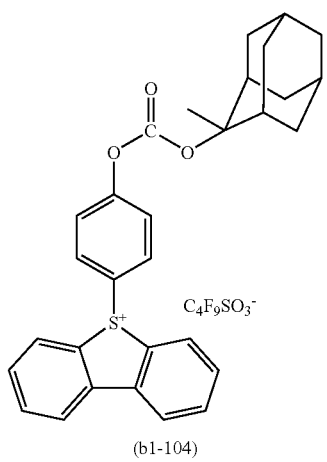
(b1-104)

-continued
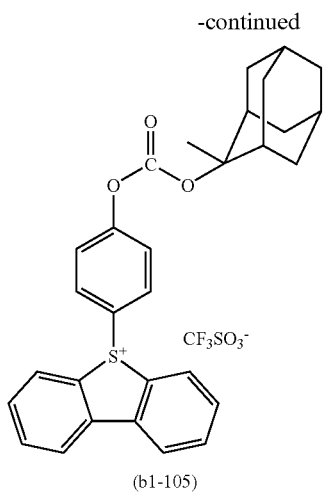
(b1-105)
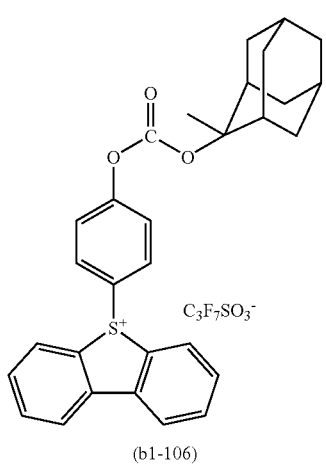
(b1-106)
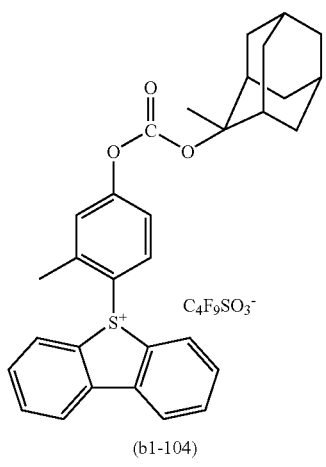
(b1-104)
-continued
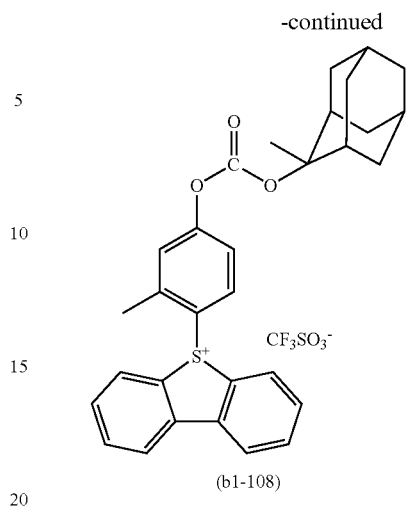
(b1-108)
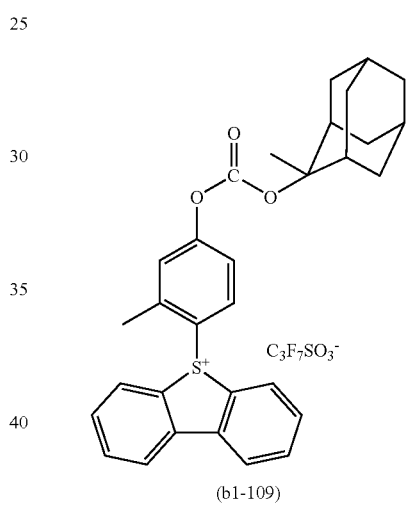
(b1-109)
[Chemical Formula 10]
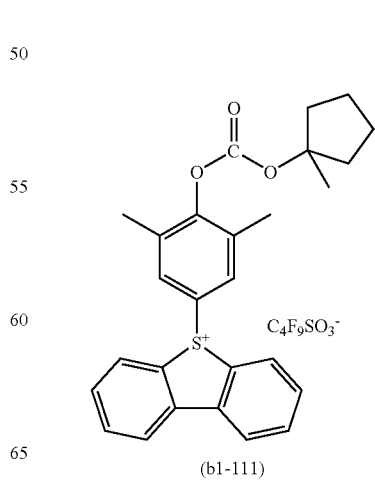
(b1-111)

-continued
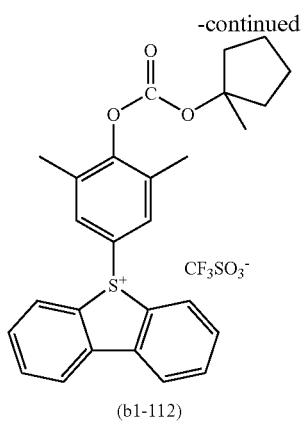
(b1-112)
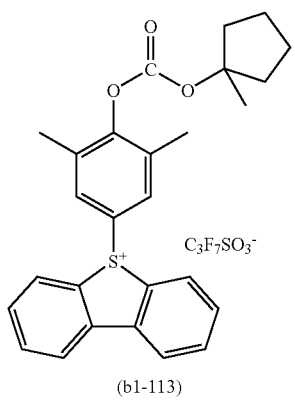
(b1-113)
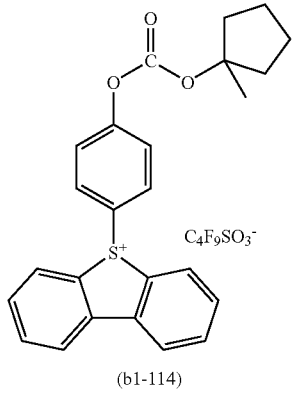
(b1-114)
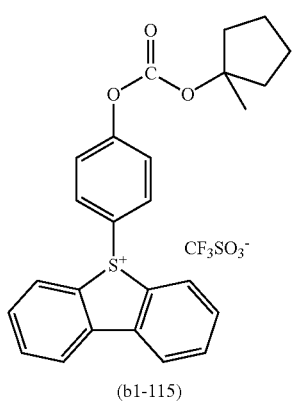
(b1-115)
-continued
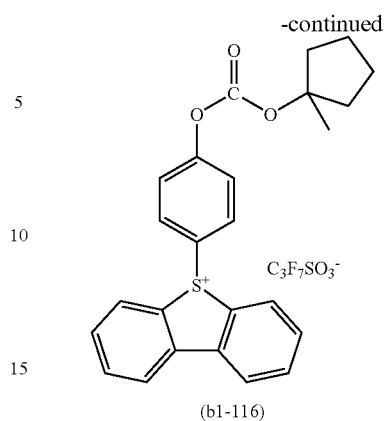
(b1-116)
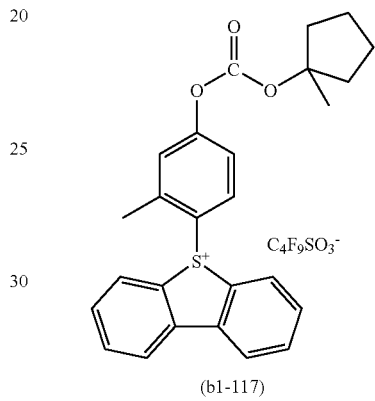
(b1-117)
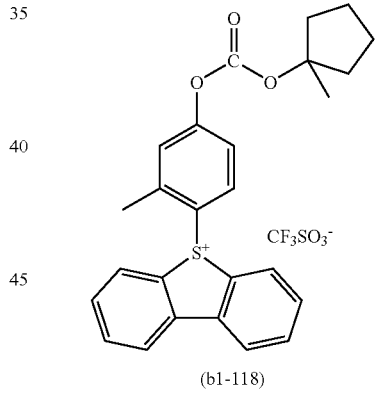
(b1-118)
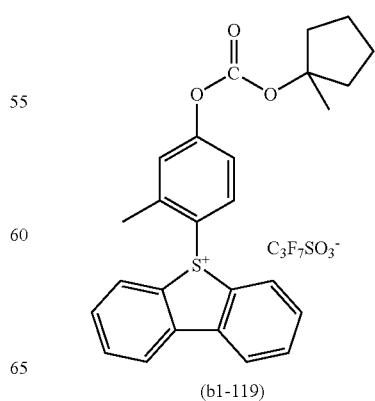
(b1-119)

-continued
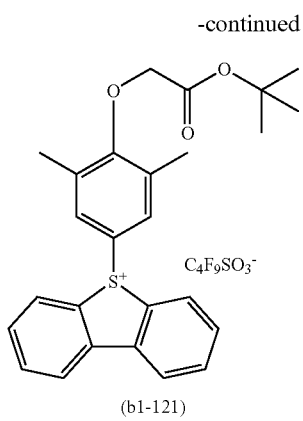
(b1-121)
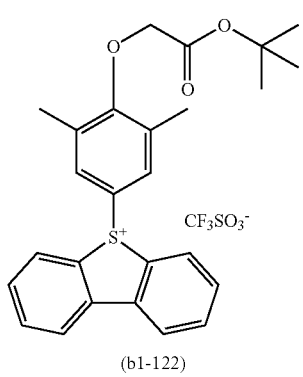
(b1-122)
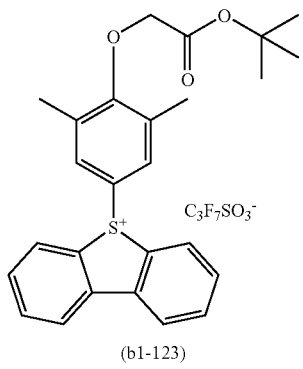
(b1-123)
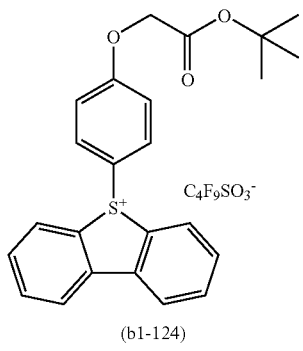
(b1-124)
[Chemical Formula 11]
-continued
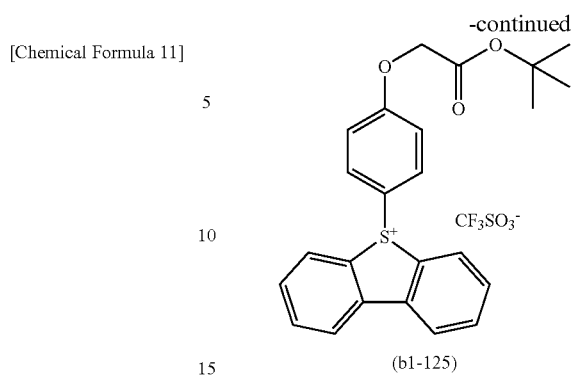
(b1-125)
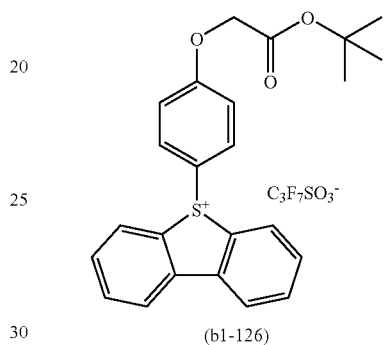
(b1-126)
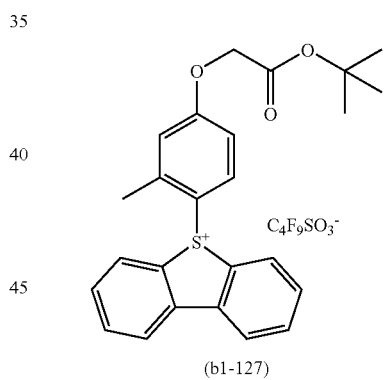
(b1-127)
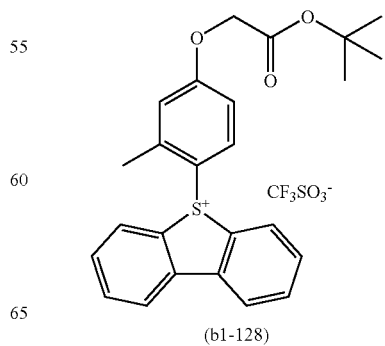
(b1-128)

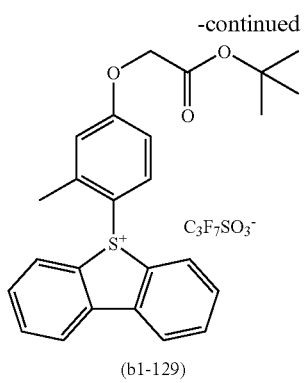
(b1-129)
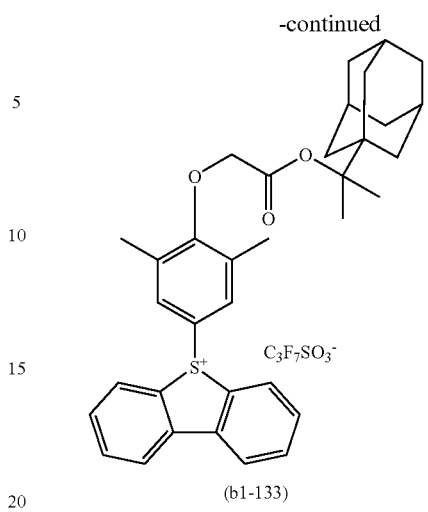
(b1-133)
[Chemical Formula 12]
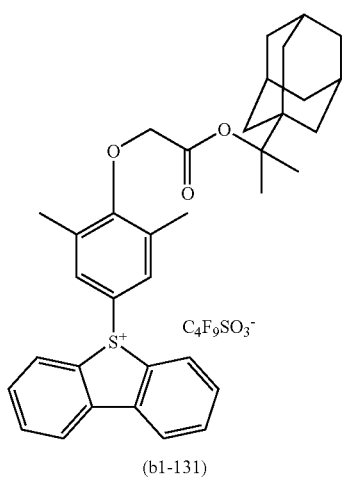
(b1-131)
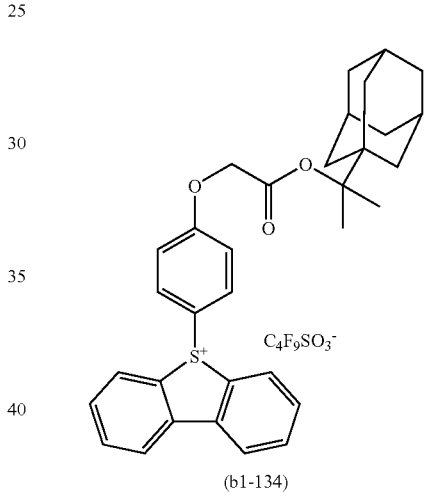
(b1-134)
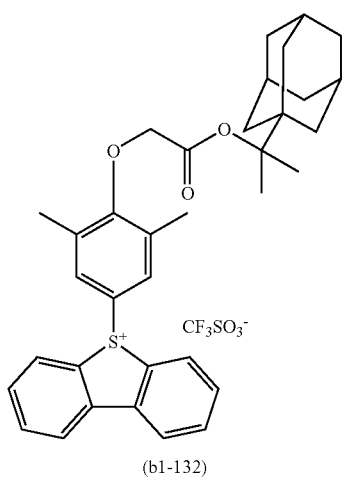
(b1-132)

-continued
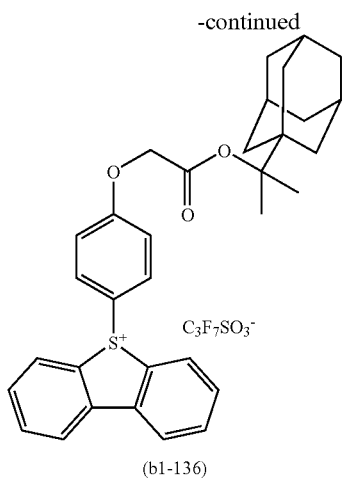
(b1-136)
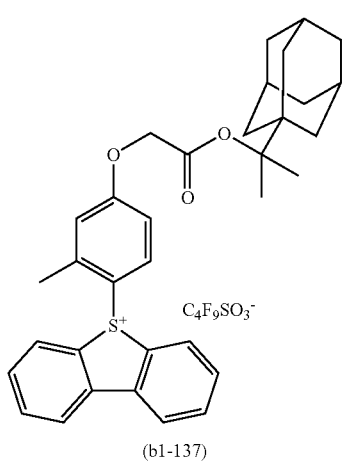
(b1-137)
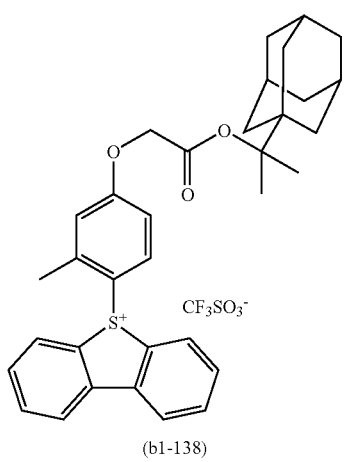
(b1-138)
-continued
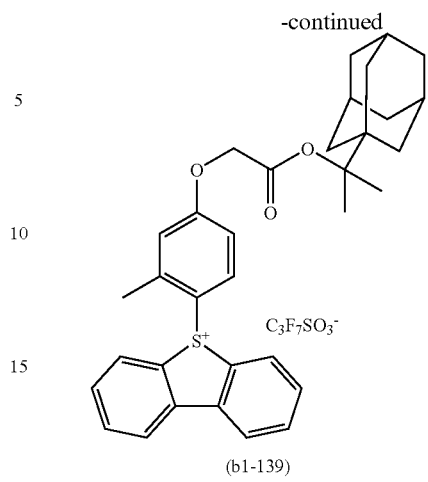
(b1-139)
[Chemical Formula 13]
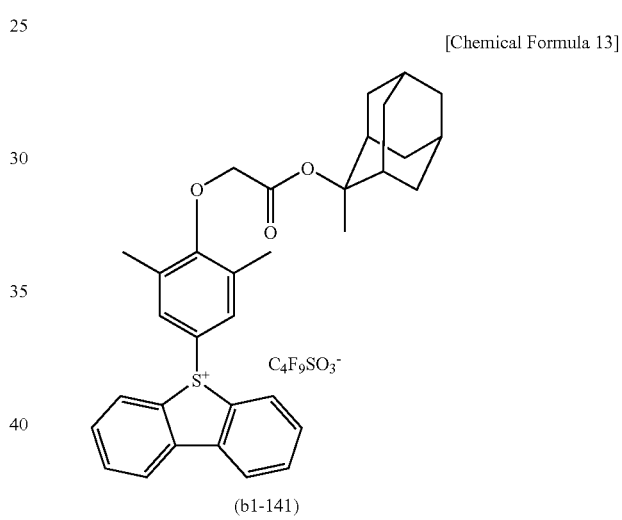
(b1-141)
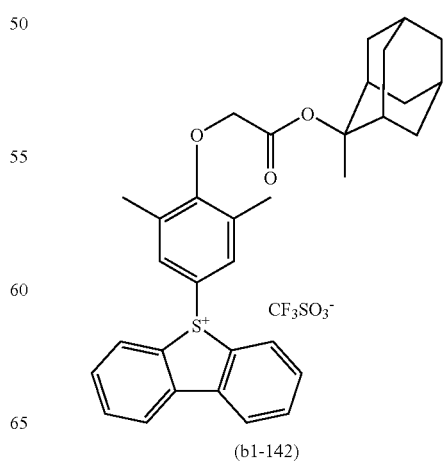
(b1-142)

-continued
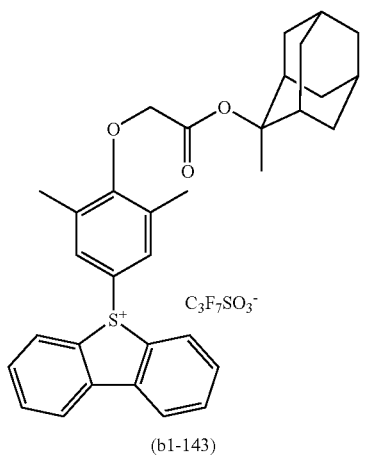
(b1-143)
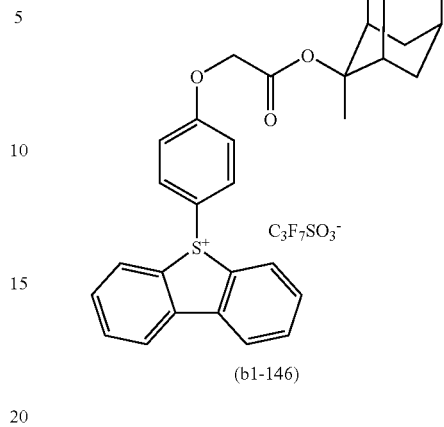
(b1-146)
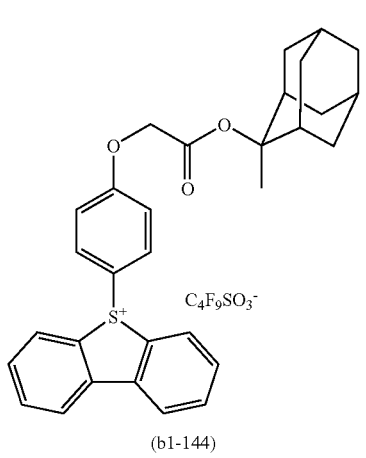
(b1-144)
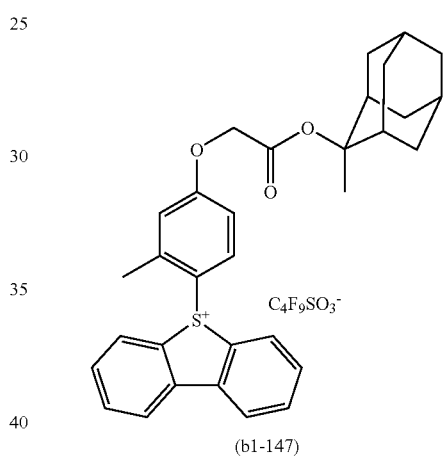
(b1-147)
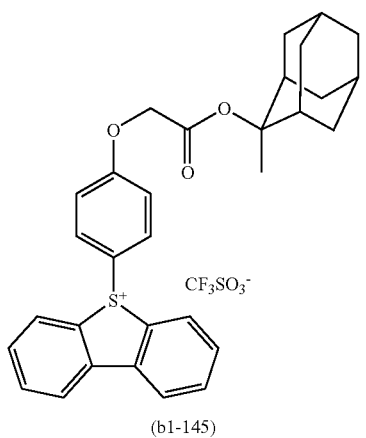
(b1-145)
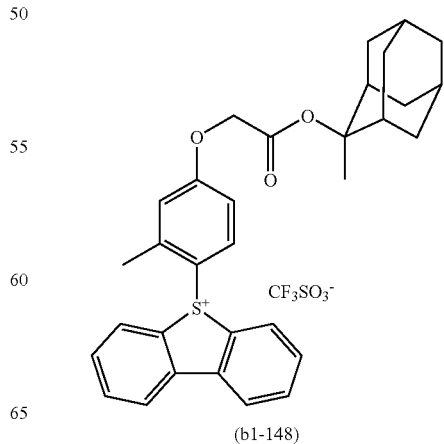
(b1-148)

-continued
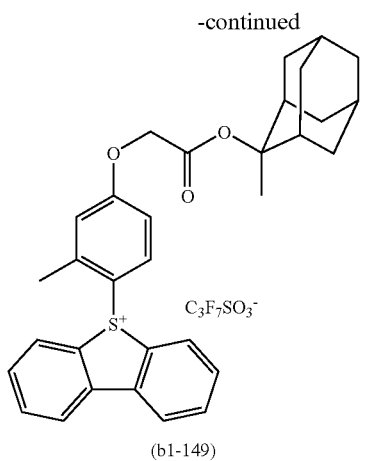
(b1-149)
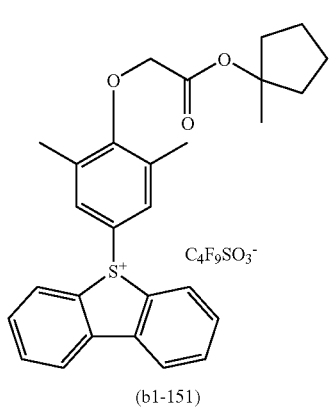
(b1-151)
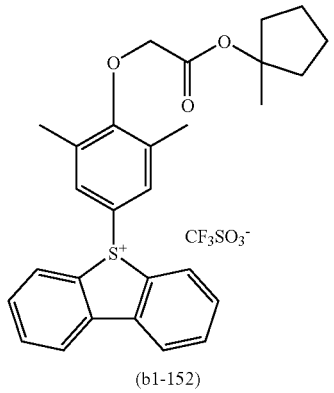
(b1-152)
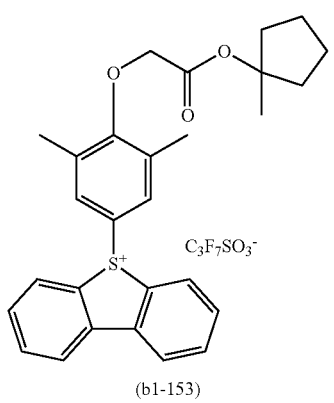
(b1-153)
[Chemical Formula 14]
-continued
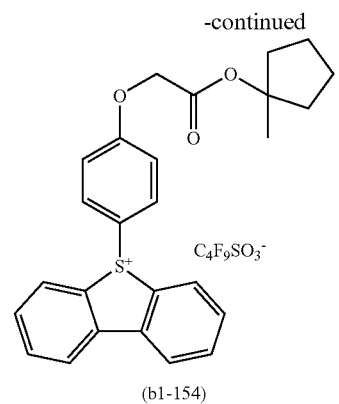
(b1-154)
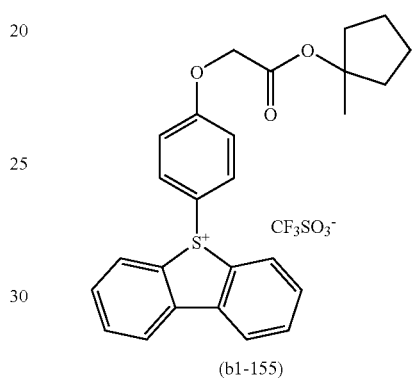
(b1-155)
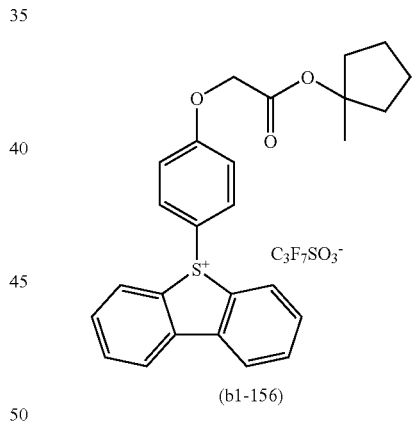
(b1-156)
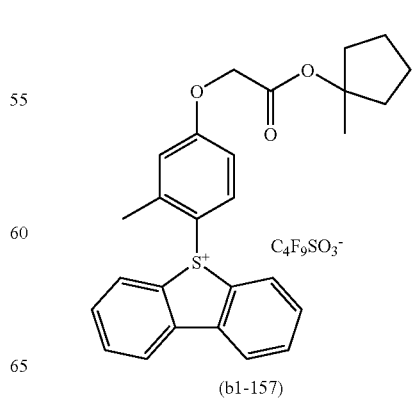
(b1-157)

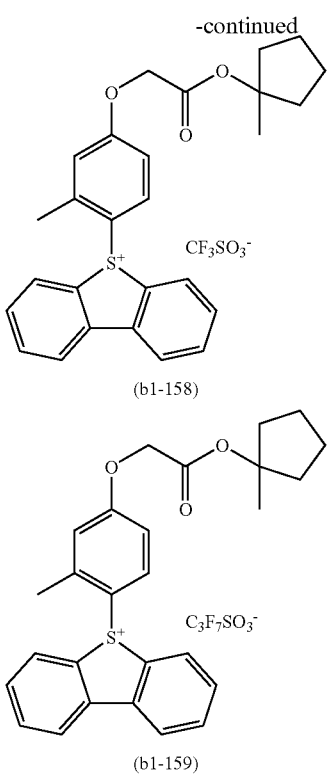

(b1-158)

(b1-159)

Among these, compounds represented by formulas (b1-81), (b1-141) and (b1-142) shown above are preferable.

<Production Method of Compound of Third Aspect>

As the compound (b1-8) of the third aspect of the present invention, those in which Q represents a single bond can be produced, for example, as follows. A compound represented by general formula (b1-5) shown below (hereafter, referred to as "intermediate compound (b1-5)"), a compound represented by general formula (b1-8-20) shown below, and an amine catalyst (e.g., N,N-dimethylaminopyridine, triethylamine, or the like) are added to an organic solvent (e.g., dichloromethane, tetrahydrofuran, or the like), and a reaction is effected at 5 to 50° C. for 10 minutes to 12 hours, preferably 30 minutes to 3 hours. Then, the reaction product is washed with diluted hydrochloric acid, water or the like, and, for example, an organic solvent (e.g., dichloromethane, tetrahydrofuran, or the like) solution of the reaction product can be dropwise added to a poor solvent (e.g., hexane, dibutylether, or the like), thereby obtaining the compound (b1-8) in which Q represents a single bond.

[Chemical Formula 15]

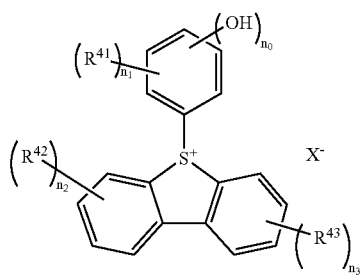

(b1-5)

wherein $R^{41}$, $R^{42}$, $R^{43}$, $n_0$, $n_1$, $n_2$, $n_3$ and $X^-$ are the same as $R^{41}$, $R^{42}$, $R^{43}$, $n_0$, $n_1$, $n_2$, $n_3$ and $X^-$ defined for general formula (b1-8) above, respectively.

[Chemical Formula 16]

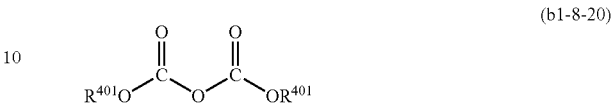

(b1-8-20)

wherein $R^{401}$ is the same as $R^{401}$ defined for general formula (b1-8) above.

Further, as the compound (b1-8) of the third aspect of the present invention, those in which Q represents a divalent linking group can be produced as follows. An intermediate compound (b1-5) and a base (e.g., sodium hydride, or the like) are added to an organic solvent (e.g., dichloromethane, tetrahydrofuran, or the like). Then, a compound represented by general formula: Br-Q-C(=O)—O—$R^{401}$ (wherein Q and $R^{401}$ are as defined above) or the like is added, and a reaction is effected under reflux for 1 to 40 hours, preferably 10 to 30 hours. Thereafter, the reaction product is added to water and extracted with an organic solvent (e.g., dichloromethane or the like), and the organic layer is condensed. Then, the resultant is dissolved in an organic solvent (e.g., dichloromethane or the like), washed with diluted hydrochloric acid, water or the like, and dropwise added to a poor solvent (e.g., hexane, dibutylether, or the like), thereby obtaining the compound (b1-8) in which Q represents a divalent linking group.

Furthermore, an intermediate compound (b1-5) can be produced as follows. A compound represented by general formula (b1-5-20) shown below is added to a methanesulfonic acid solution of diphosphorus pentaoxide, and the resultant is cooled to about room temperature. Then, a compound represented by general formula (b1-5-21) is gradually added thereto, and a reaction is effected at room temperature for 2 to 40 hours, preferably 5 to 20 hours. Thereafter, the reaction product is washed with a mixed solvent of water and an organic solvent (e.g., dichloromethane, chlorobenzene, iodobenzene, or the like), and the water phase is extracted. Then, for example, a potassium salt represented by general formula (b1-5-22) shown below is added thereto, and a reaction is effected at room temperature for 0.5 to 8 hours, preferably 1.0 to 4 hours, thereby obtaining an intermediate compound (b1-5).

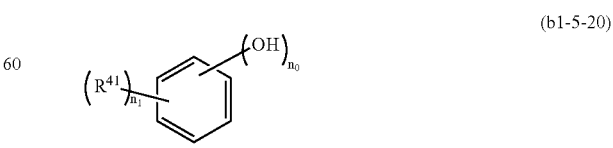

(b1-5-20)

wherein $R^{41}$, $n_0$ and $n_1$ are the same as $R^{41}$, $n_0$ and $n_1$ defined in general formula (b1-8) above, respectively.

[Chemical Formula 18]

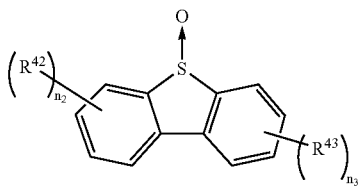

(b1-5-21)

wherein $R^{42}$, $R^{43}$, $n_2$ and $n_3$ are the same as $R^{42}$, $R^{43}$, $n_2$ and $n_3$ defined in general formula (b1-8) above, respectively.

$$K^+X^- \quad \quad (b1\text{-}5\text{-}22)$$

wherein $X^-$ is the same as $X^-$ defined in general formula (b1-8) above

<<Acid Generator of Fourth Aspect>>

The acid generator of the fourth aspect of the present invention (hereafter, frequently referred to as "acid generator (B1)") includes a compound represented by general formula (b1-8) above. In general formula (b1-8), as $R^{410}$, $R^{41}$, $R^{42}$, $R^{43}$, Q, $n_0$, $n_1$, $n_2$, $n_3$ and $X^-$, the same as those described above in connection with the compound of the third aspect of the present invention can be exemplified.

<<Compound of Fifth Aspect>

Next, the compound of the fifth aspect of the present invention will be described.

The compound of the fifth aspect of the present invention is represented by general formula (b1-9) shown above.

In general formula (b1-9) above, $R^{41}$, $R^{42}$ and $R^{43}$ each independently represents a halogen atom, a halogenated alkyl group, an alkyl group, an acetyl group, an alkoxy group, a carboxy group or a hydroxyalkyl group; $R^{402}$ and $R^{403}$ each independently represents a hydrogen atom, an alkyl group or a halogenated alkyl group; and $R^{404}$ represents an alkyl group or a halogenated alkyl group.

With respect to $R^{41}$, $R^{42}$ and $R^{43}$, the alkyl group, alkoxy group, hydroxyalkyl group, halogen atom and halogenated alkyl group are respectively the same as the alkyl group, alkoxy group, hydroxyalkyl group, halogen atom and halogenated alkyl group for $R^{41}$, $R^{42}$ and $R^{43}$ in general formula (b1-8) above.

As $R^{41}$, $R^{42}$ and $R^{43}$, an alkyl group is preferable.

In general formula (b1-9) above, as the alkyl group and halogenated alkyl group for $R^{402}$ and $R^{403}$, the same as the alkyl group and halogenated alkyl group for $R^{41}$, $R^{42}$ and $R^{43}$ can be exemplified.

As $R^{42}$ and $R^{403}$, a hydrogen atom is preferable.

In general formula (b1-9) above, the alkyl group for $R^{404}$ is a linear, branched or cyclic alkyl group, preferably having 1 to 15 carbon atoms.

The linear or branched alkyl group preferably has 1 to 10 carbon atoms, more preferably 1 to 8 carbon atoms, and most preferably 1 to 4 carbon atoms.

The cyclic alkyl group preferably has 4 to 15 carbon atoms, more preferably 4 to 12 carbon atoms, and most preferably 5 to 10 carbon atoms. Examples thereof include groups in which one hydrogen atom has been removed from a monocycloalkane or a polycycloalkane such as a bicycloalkane, tricycloalkane or tetracycloalkane. Specific examples include groups in which one hydrogen atom has been removed from a monocycloalkane such as cyclopentane or cyclohexane; and groups in which one hydrogen atom has been removed from a polycycloalkane such as adamantane, norbornane, isobornane, tricyclodecane or tetracyclododecane. Among these, groups in which one hydrogen atom has been removed from cyclopentane, cyclohexane, norbornane and adamantane are preferable, and groups in which one hydrogen atom has been removed from cyclohexane and adamantane are particularly desirable.

As the halogenated alkyl group for $R^{404}$, linear, branched or cyclic alkyl groups in which one or more hydrogen atoms have been substituted with halogen atoms can be exemplified. As the halogen atom, the same as the halogen atom for $R^{41}$ to $R^{43}$ can be exemplified.

As $R^{404}$, an alkyl group is preferable, and a cyclic alkyl group is more preferable.

$R^{403}$ and $R^{404}$ may be bonded to each other to form a ring structure. That is, $R^{403}$ and $R^{404}$ may each independently represent a linear or branched alkylene group (preferably an alkylene group of 1 to 5 carbon atoms), wherein the terminal of $R^{403}$ is bonded to the terminal of $R^{404}$.

In this case, the cyclic group is constituted of $R^{403}$, $R^{404}$, the oxygen atom to which $R^{404}$ is bonded, and the carbon atom to which the oxygen atom and $R^{403}$ are bonded. As the cyclic group, a 4- to 7-membered ring is preferable, and a 4- to 6-membered ring is more preferable. Specific examples of the cyclic group include tetrahydropyranyl group and tetrahydrofuranyl group.

In general formula (b1-9) above, $n_0$ and $n_1$ to $n_3$ are the same as $n_0$ and $n_1$ to $n_3$ in general formula (b1-8) above.

In general formula (b1-9) above, $X^-$ represents an anion. As the anion moiety of $X^-$, there is no particular limitation, and any anion moiety can be appropriately used which is known as an anion moiety of an onium salt-based acid generator. For example, an anion represented by general formula: $R^{14}SO_3^-$ (wherein $R^{14}$ represents a linear, branched or cyclic alkyl group, a halogenated alkyl group, an aryl group or an alkenyl group) or an anion represented by general formula: $R^1$—O—$Y^1$—$SO_3^-$ (wherein $R^1$ represents a monovalent aliphatic hydrocarbon group, a monovalent aromatic organic group or a monovalent hydroxyalkyl group; and $Y^1$ represents an alkylene group of 1 to 4 carbon atoms which may be fluorinated) can be used.

General formula $R^{14}SO_3^-$ above is the same as general formula $R^{14}SO_3^-$ described above in connection with the compound of the third aspect of the present invention.

In general formula $R^1$—O—$Y^1$—$SO_3^-$ above, $R^1$ represents a monovalent aliphatic hydrocarbon group, a monovalent aromatic organic group or a monovalent hydroxyalkyl group; and $Y^1$ represents an alkylene group of 1 to 4 carbon atoms which may be fluorinated.

As the monovalent aliphatic hydrocarbon group for $R^1$, for example, a linear, branched or cyclic, monovalent saturated hydrocarbon group of 1 to 15 carbon atoms, or a linear or branched, monovalent unsaturated hydrocarbon groups of 2 to 5 carbon atoms can be mentioned.

As examples of linear, monovalent saturated hydrocarbon groups, the same as those described above in connection with the compound of the third aspect of the present invention can be exemplified.

As examples of branched, monovalent saturated hydrocarbon groups, the same as those described above in connection with the compound of the third aspect of the present invention can be exemplified.

As examples of cyclic, monovalent saturated hydrocarbon groups, the same as those described above in connection with the compound of the third aspect of the present invention can be exemplified.

As examples of linear, monovalent unsaturated hydrocarbon group, the same as those described above in connection with the compound of the third aspect of the present invention can be exemplified, as well as a vinyl group.

As examples of branched, monovalent unsaturated hydrocarbon groups, the same as those described above in connection with the compound of the third aspect of the present invention can be exemplified.

The monovalent aliphatic hydrocarbon group for $R^1$ preferably has 2 to 4 carbon atoms, and it is particularly desirable that the monovalent aliphatic hydrocarbon group have 3 carbon atoms.

Examples of monovalent aromatic organic groups for $R^1$ include the same as those described above in connection with the compound of the third aspect of the present invention can be exemplified, as well as anthryl group, benzyl group and phenethyl group; and arylalkyl groups, such as a 1-naphthylmethyl group, 2-naphthylmethyl group, 1-naphthylethyl group and 2-naphthylethyl group. In the above-mentioned arylalkyl groups, the alkyl chain preferably has 1 to 4 carbon atoms, more preferably 1 or 2 carbon atoms, and it is particularly desirable that the alkyl chain has 1 carbon atom. These aryl groups, heteroaryl groups and arylalkyl groups may have a substituent such as an alkyl group of 1 to 10 carbon atoms, a halogenated alkyl group, an alkoxy group, a hydroxyl group or a halogen atom. The alkyl group or halogenated alkyl group as the substituent preferably has 1 to 8 carbon atoms, and more preferably 1 to 4 carbon atoms. The halogenated alkyl group is preferably a fluorinated alkyl group. Examples of halogen atoms include a fluorine atom, a chlorine atom, a bromine atom and an iodine atom, and a fluorine atom is preferable.

The monovalent hydroxyalkyl group for $R^1$ is the same as those described above in connection with the third aspect of the present invention. Specific examples include those exemplified above in connection with the third aspect of the present invention, as well as hydroxymethyl group and hydroxyethyl group.

The monovalent hydroxyalkyl group for $R^1$ preferably has 1 to 10 carbon atoms, more preferably 1 to 8 carbon atoms, still more preferably 1 to 6 carbon atoms, and most preferably 1 to 3 carbon atoms.

As examples of alkylene groups of 1 to 4 carbon atoms for $Y^1$ which may be fluorinated, the same as those described above in connection with the compound of the third aspect of the present invention can be exemplified.

Further, as examples of fluorinated alkylene groups preferable for $Y^1$, the same as those described above in connection with the compound of the third aspect of the present invention can be exemplified.

In general formula (b1-9) above, as $X^-$, anions represented by general formula (b-3) shown above and anions represented by general formula (b-4) shown above may be used.

Specific examples of the compound of the fifth aspect of the present invention are shown below.

[Chemical Formula 19]

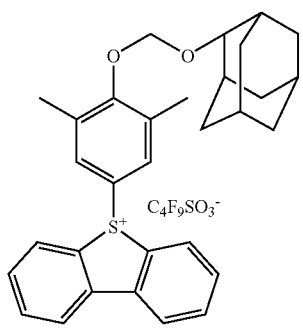

(b1-91')

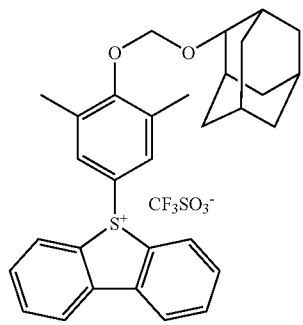

(b1-92')

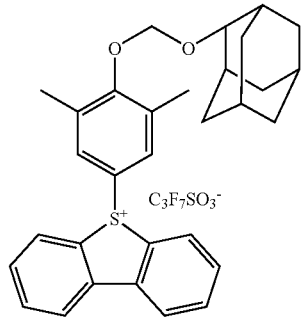

(b1-93')

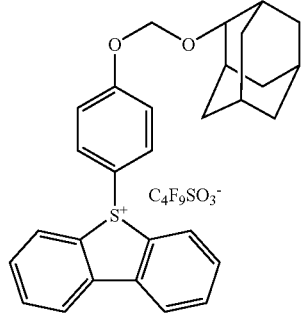

(b1-94')

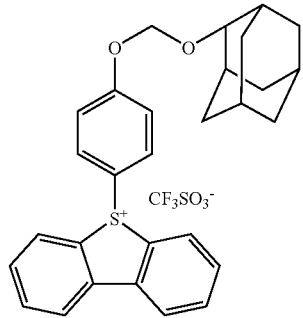

(b1-95')

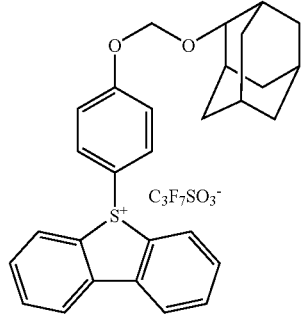

(b1-96')

-continued
(b1-97')
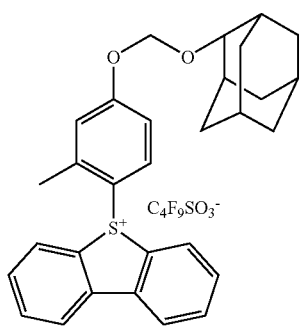
(b1-98')
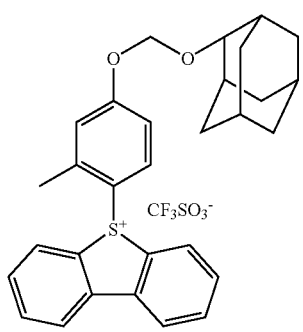
(b1-99')
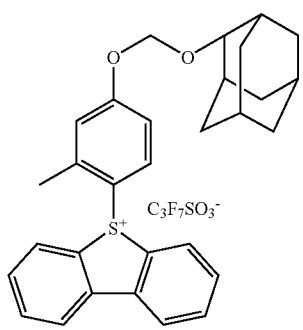
[Chemical Formula 20]
(b1-100')
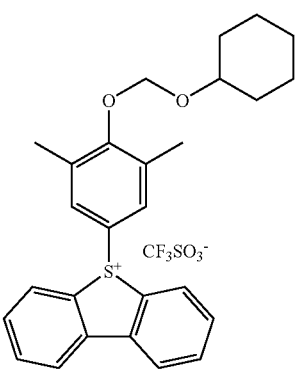
-continued
(b1-101')
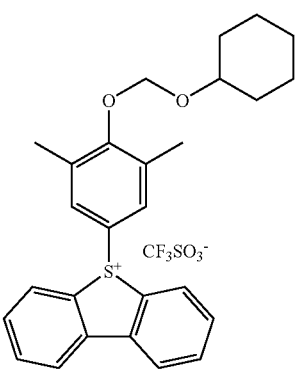
(b1-102')
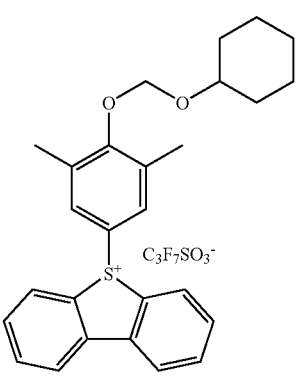
(b1-103')
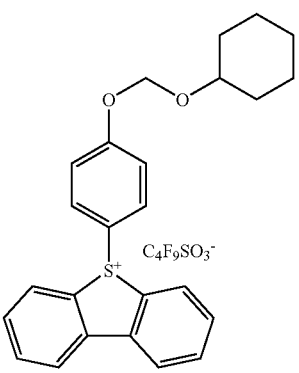
(b1-104')
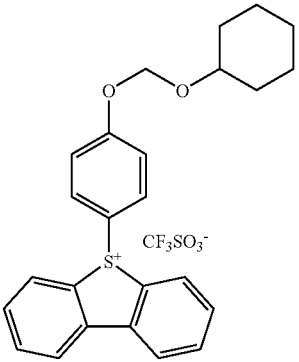

-continued

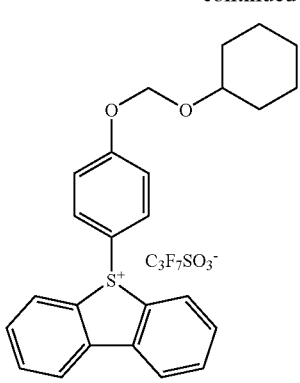
(b1-105')

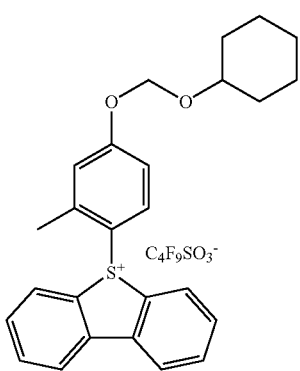
(b1-106')

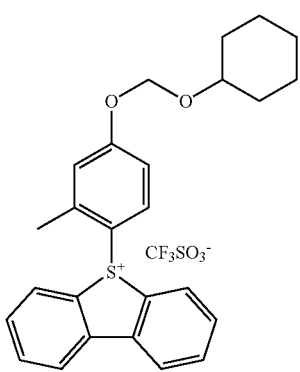
(b1-107')

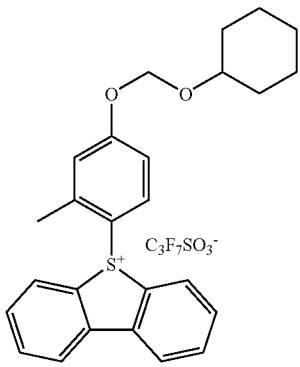
(b1-108')

Among these, compounds represented by formula (b1-91') and (b1-100') shown above are preferable.

<Production Method of Compound of Fifth Aspect>

The compound (b1-9) of the fifth aspect of the present invention can be produced as follows.

Specifically, a compound represented by general formula (b1-5) shown below (hereafter, referred to as "intermediate compound (b1-5)") is added to an organic solvent (e.g., dichloromethane, tetrahydrofuran, or the like), and cooled down to −10 to 10° C. Then, a basic catalyst (e.g., a strongly basic catalyst such as sodium hydride) is added thereto, followed by addition of a compound represented by general formula (b1-9-20). At this time, it is preferable that the compound represented by general formula (b1-9-20) be dissolved in the above-mentioned organic solvent and dropwise added in the form of a solution. Then, a reaction is effected at room temperature for 10 minutes to 12 hours, preferably 30 minutes to 3 hours. Thereafter, the reaction product is washed with diluted hydrochloric acid, water or the like, and an organic solvent (e.g., dichloromethane, tetrahydrofuran, or the like) solution of the reaction product can be dropwise added to a poor solvent (e.g., hexane, dibutylether, or the like), thereby obtaining the compound (b1-9).

[Chemical Formula 21]

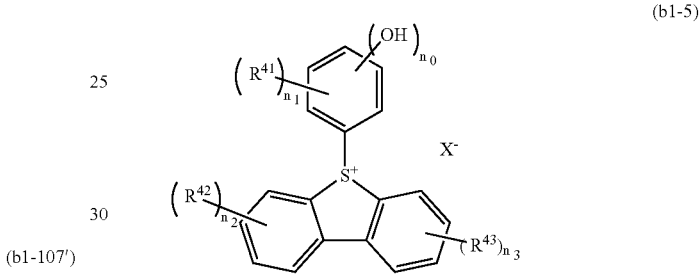
(b1-5)

wherein $R^{41}$, $R^{42}$, $R^{43}$, $n_0$, $n_1$, $n_2$, $n_3$ and $X^-$ are the same as $R^{41}$, $R^{42}$, $R^{43}$, $n_0$, $n_1$, $n_2$, $n_3$ and $X^-$ defined for general formula (b1-9) above, respectively.

[Chemical Formula 22]

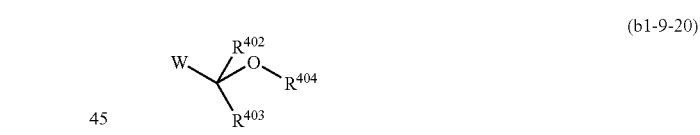
(b1-9-20)

wherein $R^{402}$, $R^{403}$ and $R^{404}$ are the same as $R^{402}$, $R^{403}$ and $R^{404}$ defined for general formula (b1-9) above, respectively; and W represents a halogen atom.

In formula (b1-9-20) above, W represents a halogen atom. Examples thereof include a fluorine atom, a chlorine atom, a bromine atom and an iodine atom, and a chlorine atom is preferable.

Further, the intermediate compound (b1-5) can be produced in the same manner as described above in connection with the compound of the third aspect of the present invention.

<<Acid Generator of Sixth Aspect>>

The acid generator of the sixth aspect of the present invention (hereafter, frequently referred to as "acid generator (B1')") includes a compound represented by general formula (b1-9) above. In general formula (b1-9), as $R^{402}$, $R^{403}$, $R^{404}$, $R^{41}$, $R^{42}$, $R^{43}$, $n_0$, $n_1$, $n_2$, $n_3$ and $X^-$, the same as those described above in connection with the compound of the fifth aspect of the present invention can be exemplified.

<<Resist Composition>>

The resist composition of the first aspect of the present invention includes a base component (A) (hereafter, frequently referred to as "component (A)") which exhibits changed solubility in an alkali developing solution under action of acid and an acid-generator component (B) which generates acid upon irradiation, and the acid-generator component (B) (hereafter, frequently referred to as "component (B)") contains an acid generator (B1) including a compound represented by general formula (b1-8) shown above or an acid generator (B1') including a compound represented by general formula (b1-9) shown above. In general formula (b1-8), as $R^{410}$, $R^{41}$, $R^{42}$, $R^{43}$, Q, $n_0$, $n_1$, $n_2$, $n_3$ and $X^-$, the same as those described above in connection with the compound of the third aspect of the present invention can be exemplified. Further, in general formula (b1-9), as $R^{402}$, $R^{403}$, $R^{404}$, $R^{41}$, $R^{42}$, $R^{43}$, $n_0$, $n_1$, $n_2$, $n_3$ and $X^-$, the same as those described above in connection with the compound of the fifth aspect of the present invention can be exemplified.

In the resist composition of the present invention, as the component (A), a polymeric material which exhibits changed solubility in an alkali developing solution under action of acid may be used. Alternatively, as the component (A), a low molecular weight material which exhibits changed solubility in an alkali developing solution under action of acid may be used.

Further, the resist composition of the present invention may be a negative resist composition or a positive resist composition.

When the resist composition of the present invention is a negative resist composition, for example, the component (A) is an alkali-soluble resin, and a cross-linking agent (C) is blended with the resist composition.

In the negative resist composition, during resist pattern formation, when acid is generated from the component (B) upon exposure, the action of this acid causes cross-linking between the alkali-soluble resin and the cross-linking agent, and the cross-linked portion becomes alkali insoluble.

As the alkali-soluble resin, it is preferable to use a resin having a structural unit derived from at least one of α-(hydroxyalkyl)acrylic acid and a lower alkyl ester of α-(hydroxyalkyl)acrylic acid, as it enables formation of a satisfactory resist pattern with minimal swelling. Here, the term "α-(hydroxyalkyl) acrylic acid" refers to one or both of acrylic acid in which a hydrogen atom is bonded to the carbon atom on the α-position having the carboxyl group bonded thereto, and α-hydroxyalkylacrylic acid in which a hydroxyalkyl group preferably a hydroxyalkyl group of 1 to 5 carbon atoms) is bonded to the carbon atom on the α-position.

As the cross-linking agent (C), typically, an amino-based cross-linking agent such as a glycoluril having a methylol group or alkoxymethyl group is preferable, as it enables formation of a resist pattern with minimal swelling. The amount of the cross-linking agent (C) added is preferably within the range from 1 to 50 parts by weight, relative to 100 parts by weight of the alkali-soluble resin.

When the resist composition of the present invention is a positive resist composition, the component (A) exhibits increased solubility in an alkali developing solution under action of acid. More specifically, the component (A) is an alkali-insoluble resin having acid dissociable, dissolution inhibiting groups, and during resist pattern formation, when acid is generated from the component (B) upon exposure, the acid dissociable, dissolution inhibiting groups are dissociated by the generated acid, and the component (A) becomes alkali soluble. Therefore, in the formation of a resist pattern, by conducting selective exposure of a resist film formed by applying the positive resist composition onto a substrate, the exposed portions become alkali soluble, whereas the unexposed portions remain alkali-insoluble, and hence, a resist pattern can be formed by alkali developing.

In the resist composition of the present invention, the component (A) is preferably a resin component (A1) (hereafter referred to as "component (A1)") which exhibits increased solubility in an alkali-developing solution under action of acid. That is, the resist composition of the present invention is preferably a positive resist composition.

<Component (A1)>

The component (A1) suitably used for such a positive resist composition preferably has a structural unit (a1) derived from an acrylate ester having an acid dissociable, dissolution inhibiting group.

Further, it is preferable that the component (A1) also has a structural unit (a2) derived from an acrylate ester having a lactone-containing cyclic group.

Furthermore, it is preferable that the component (A1) also has a structural unit (a3) derived from an acrylate ester having a polar group-containing aliphatic hydrocarbon group.

In the present descriptions and the claims, the term "structural unit derived from an acrylate ester" refers to a structural unit which is formed by the cleavage of the ethylenic double bond of an acrylate ester.

The term "acrylate ester" is a generic term that includes acrylate esters having a hydrogen atom bonded to the carbon atom on the α-position, and acrylate esters having a substituent (an atom other than a hydrogen atom or a group) bonded to the carbon atom on the α-position. As the substituent, a lower alkyl group or a halogenated lower alkyl group can be mentioned.

With respect to the "structural unit derived from an acrylate ester", the "α-position (the carbon atom on the α-position)" refers to the carbon atom having the carbonyl group bonded thereto, unless specified otherwise.

With respect to the acrylate ester, specific examples of the lower alkyl group for the substituent at the α-position include linear or branched alkyl groups such as a methyl group, ethyl group, propyl group, isopropyl group, n-butyl group, isobutyl group, tert-butyl group, pentyl group, isopentyl group, and neopentyl group.

Specific examples of the halogenated lower alkyl group include groups in which some or all of the hydrogen atoms of the aforementioned "lower alkyl group for the substituent at the α-position" are substituted with halogen atoms. Examples of halogen atoms include fluorine atoms, chlorine atoms, bromine atoms and iodine atoms, and fluorine atoms are particularly desirable.

In the present invention, it is preferable that a hydrogen atom, a lower alkyl group or a halogenated lower alkyl group is bonded to the α-position of the acrylate ester, more preferably a hydrogen atom, a lower alkyl group or a fluorinated lower alkyl group. In terms of industrial availability, a hydrogen atom or a methyl group is particularly desirable.

—Structural Unit (a1)

Structural unit (a1) is a structural unit derived from an acrylate ester having an acid dissociable, dissolution inhibiting group.

As the acid-dissociable, dissolution-inhibiting group in the structural unit (a1), any of the groups that have been proposed as acid-dissociable, dissolution-inhibiting groups for the base resins of chemically amplified resists can be used, provided the group has an alkali dissolution-inhibiting effect that renders the entire component (A1) alkali-insoluble prior to dissociation, and then following dissociation by action of acid, causes the entire component (A1) to change to an alkali-soluble state.

Generally, groups that form either a cyclic or linear tertiary alkyl ester with the carboxyl group of the (meth)acrylate ester, and acetal-type acid dissociable, dissolution inhibiting groups such as alkoxyalkyl groups are widely known. In the present description, the term "(meth)acrylate ester" is a generic term that includes either or both of the acrylate ester having a hydrogen atom bonded to the α-position and the methacrylate ester having a methyl group bonded to the α-position.

Here, a tertiary alkyl ester describes a structure in which an ester is formed by substituting the hydrogen atom of a carboxyl group with a linear or cyclic tertiary alkyl group, and a tertiary carbon atom within the linear or cyclic tertiary alkyl group is bonded to the oxygen atom at the terminal of the carbonyloxy group (—C(O)—O—). In this tertiary alkyl ester, the action of acid causes cleavage of the bond between the oxygen atom and the tertiary carbon atom.

The linear or cyclic alkyl group may have a substituent.

Hereafter, for the sake of simplicity, groups that exhibit acid dissociability as a result of the formation of a tertiary alkyl ester with a carboxyl group are referred to as "tertiary alkyl ester-type acid-dissociable, dissolution-inhibiting groups".

Examples of tertiary alkyl ester-type acid dissociable, dissolution inhibiting groups include aliphatic branched, acid dissociable, dissolution inhibiting groups and aliphatic cyclic group-containing acid dissociable, dissolution inhibiting groups.

In the present description and claims, the term "aliphatic" is a relative concept used in relation to the term "aromatic", and defines a group or compound that has no aromaticity.

The term "aliphatic branched" refers to a branched structure having no aromaticity.

The "aliphatic branched, acid dissociable, dissolution inhibiting group" is not limited to be constituted of only carbon atoms and hydrogen atoms (not limited to hydrocarbon groups), but is preferably a hydrocarbon group.

Further, the "hydrocarbon group" may be either saturated or unsaturated, but is preferably saturated.

Examples of aliphatic branched, acid dissociable, dissolution inhibiting groups include tertiary alkyl groups of 4 to 8 carbon atoms, and specific examples include a tert-butyl group, tert-pentyl group and tert-heptyl group.

The term "aliphatic cyclic group" refers to a monocyclic group or polycyclic group that has no aromaticity.

The "aliphatic cyclic group" within the structural unit (a1) may or may not have a substituent. Examples of substituents include lower alkyl groups of 1 to 5 carbon atoms, fluorine atom, fluorinated lower alkyl groups of 1 to 5 carbon atoms, and oxygen atom (=O).

The basic ring of the "aliphatic cyclic group" exclusive of substituents is not limited to be constituted from only carbon and hydrogen (not limited to hydrocarbon groups), but is preferably a hydrocarbon group. Further, the "hydrocarbon group" may be either saturated or unsaturated, but is preferably saturated. Furthermore, the "aliphatic cyclic group" is preferably a polycyclic group.

As such aliphatic cyclic groups, groups in which one or more hydrogen atoms have been removed from a monocycloalkane or a polycycloalkane such as a bicycloalkane, tricycloalkane or tetracycloalkane which may or may not be substituted with a lower alkyl group, a fluorine atom or a fluorinated lower alkyl group, may be exemplified. Specific examples include groups in which one or more hydrogen atoms have been removed from a monocycloalkane such as cyclopentane and cyclohexane; and groups in which one or more hydrogen atoms have been removed from a polycycloalkane such as adamantane, norbornane, isobornane, tricyclodecane or tetracyclododecane.

As the aliphatic cyclic group-containing acid dissociable, dissolution inhibiting group, for example, a group which has a tertiary carbon atom on the ring structure of the cycloalkyl group can be mentioned. Specific examples include 2-methyl-2-adamantyl group and a 2-ethyl-2-adamantyl group. Further, groups having an aliphatic cyclic group such as an adamantyl group, cyclohexyl group, cyclopentyl group, norbornyl group, tricyclodecanyl group or tetracyclodecanyl group, and a branched alkylene group having a tertiary carbon atom bonded thereto, as in the structural units represented by general formulas (a1"-1) to (a1"-6) shown below, can be exemplified.

[Chemical Formula 23]

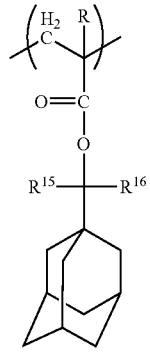

(a1"-1)

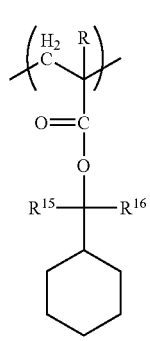

(a1"-2)

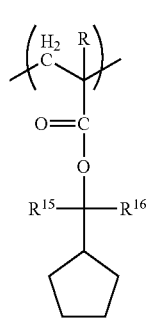

(a1"-3)

-continued (a1″-4)

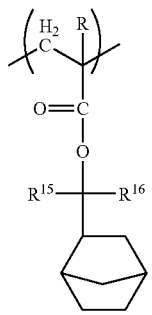

(a1″-5)

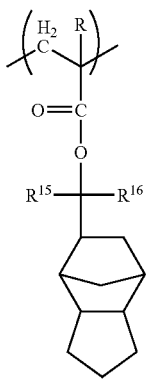

(a1″-6)

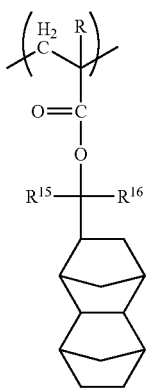

wherein R represents a hydrogen atom, a lower alkyl group or a halogenated lower alkyl group; and $R^{15}$ and $R^{16}$ each independently represents an alkyl group (which may be linear or branched, and preferably has 1 to 5 carbon atoms).

In general formulas (a1″-1) to (a1″-6) above, the lower alkyl group or halogenated lower alkyl group for R are the same as the lower alkyl group or halogenated lower alkyl group which can be bonded to the α-position of the aforementioned acrylate ester.

An "acetal-type acid dissociable, dissolution inhibiting group" is generally substituted with a hydrogen atom at the terminal of an alkali-soluble group such as a carboxy group or hydroxyl group, so as to be bonded with an oxygen atom. When acid is generated upon exposure, the generated acid acts to break the bond between the acetal-type acid dissociable, dissolution inhibiting group and the oxygen atom to which the acetal-type, acid dissociable, dissolution inhibiting group is bonded.

Examples of acetal-type acid dissociable, dissolution inhibiting groups include groups represented by general formula (p1) shown below.

[Chemical Formula 24]

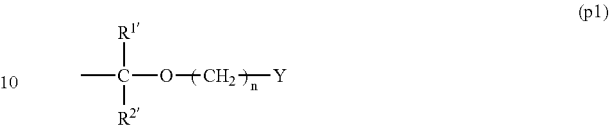

(p1)

wherein $R^{1\prime}$ and $R^{2\prime}$ each independently represents a hydrogen atom or a lower alkyl group; n represents an integer of 0 to 3; and Y represents a lower alkyl group or an aliphatic cyclic group.

In general formula (p1) above, n is preferably an integer of 0 to 2, more preferably 0 or 1, and most preferably 0.

As the lower alkyl group for $R^{1\prime}$ and $R^{2\prime}$, the same as the lower alkyl groups for R above can be exemplified. As the lower alkyl group for $R^{1\prime}$ and $R^{2\prime}$, a methyl group or ethyl group is preferable, and a methyl group is particularly desirable.

In the present invention, it is preferable that at least one of $R^{1\prime}$ and $R^{2\prime}$ be a hydrogen atom. That is, it is preferable that the acid dissociable, dissolution inhibiting group (p1) is a group represented by general formula (p1-1) shown below.

[Chemical Formula 25]

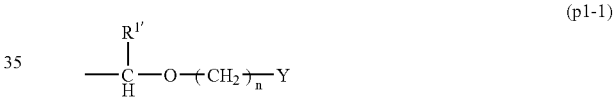

(p1-1)

wherein $R^{1\prime}$, n and Y are as defined above.

As the lower alkyl group for Y, the same as the lower alkyl groups for R above can be exemplified.

As the aliphatic cyclic group for Y, any of the aliphatic monocyclic/polycyclic groups which have been proposed for conventional ArF resists and the like can be appropriately selected for use. For example, the same groups described above in connection with the "aliphatic cyclic group" can be exemplified.

Further, as the acetal-type, acid dissociable, dissolution inhibiting group, groups represented by general formula (p2) shown below can also be exemplified.

[Chemical Formula 26]

(p2)

wherein $R^{17}$ and $R^{18}$ each independently represents a linear or branched alkyl group or a hydrogen atom; and $R^{19}$ represents a linear, branched or cyclic alkyl group; or $R^{17}$ and $R^{19}$ each independently represents a linear or branched alkylene group, wherein the terminal of $R^{17}$ is bonded to the terminal of $R^{19}$ to form a ring.

The alkyl group for $R^{17}$ and $R^{18}$ preferably has 1 to 15 carbon atoms, and may be either linear or branched. As the alkyl group, an ethyl group or a methyl group is preferable, and a methyl group is most preferable.

It is particularly desirable that either one of $R^{17}$ and $R^{18}$ be a hydrogen atom, and the other be a methyl group.

$R^{19}$ represents a linear, branched or cyclic alkyl group which preferably has 1 to 15 carbon atoms, and may be any of linear, branched or cyclic.

When $R^{19}$ represents a linear or branched alkyl group, it is preferably an alkyl group of 1 to 5 carbon atoms, more preferably an ethyl group or methyl group, and most preferably an ethyl group.

When $R^{19}$ represents a cycloalkyl group, it preferably has 4 to 15 carbon atoms, more preferably 4 to 12 carbon atoms, and most preferably 5 to 10 carbon atoms. As examples of the cycloalkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be exemplified. Specific examples include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane. Of these, a group in which one or more hydrogen atoms have been removed from adamantane is preferable.

In general formula (p2) above, $R^{17}$ and $R^{19}$ may each independently represent a linear or branched alkylene group preferably an alkylene group of 1 to 5 carbon atoms), and the terminal of $R^{19}$ may be bonded to the terminal of $R^{17}$.

In such a case, a cyclic group is formed by $R^{17}$, $R^{19}$, the oxygen atom having $R^{19}$ bonded thereto and the carbon atom having the oxygen atom and $R^{17}$ bonded thereto. Such a cyclic group is preferably a 4 to 7-membered ring, and more preferably a 4 to 6-membered ring. Specific examples of the cyclic group include tetrahydropyranyl group and tetrahydrofuranyl group.

As the structural unit (a1), it is preferable to use at least one member selected from the group consisting of structural units represented by formula (a1-0-1) shown below and structural units represented by formula (a1-0-2) shown below.

[Chemical Formula 27]

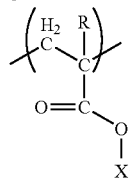

(a1-0-1)

wherein R represents a hydrogen atom, a lower alkyl group or a halogenated lower alkyl group; and $X^1$ represents an acid dissociable, dissolution inhibiting group.

[Chemical Formula 28]

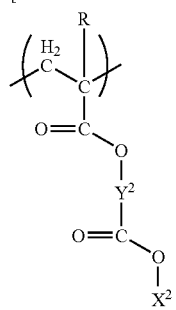

(a1-0-2)

wherein R represents a hydrogen atom, a lower alkyl group or a halogenated lower alkyl group; $X^2$ represents an acid dissociable, dissolution inhibiting group; and $Y^2$ represents an alkylene group or an aliphatic cyclic group.

In general formula (a1-0-1) shown above, lower alkyl group and halogenated lower alkyl group for R are the same as the lower alkyl group and halogenated lower alkyl group which can be bonded to the α-position of the aforementioned acrylate ester.

$X^1$ is not particularly limited as long as it is an acid dissociable, dissolution inhibiting group. Examples thereof include the aforementioned tertiary alkyl ester-type acid dissociable, dissolution inhibiting groups and acetal-type acid dissociable, dissolution inhibiting groups, and tertiary alkyl ester-type acid dissociable, dissolution inhibiting groups are preferable.

In general formula (a1-0-2), R is as defined above.

$X^2$ is the same as $X^1$ in general formula (a1-0-1).

$Y^2$ is preferably an alkylene group of 1 to 4 carbon atoms or a divalent aliphatic cyclic group. As the aliphatic cyclic group, the same as those exemplified above in connection with the explanation of "aliphatic cyclic group" can be used, except that two hydrogen atoms have been removed therefrom.

Specific examples of the structural unit (a1) include structural units represented by general formulas (a1-1) to (a1-4) shown below.

[Chemical Formula 29]

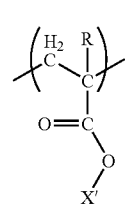

(a1-1)

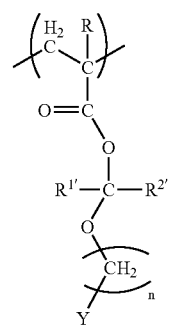

(a1-2)

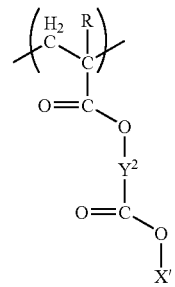

(a1-3)

-continued (a1-4)

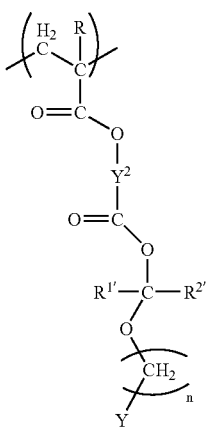

wherein X' represents a tertiary alkyl ester-type acid dissociable, dissolution inhibiting group; Y represents a lower alkyl group of 1 to 5 carbon atoms or an aliphatic cyclic group; n represents an integer of 0 to 3; $Y^2$ represents an alkylene group or an aliphatic cyclic group; R is as defined above; and $R^{1\prime}$ and $R^{2\prime}$ each independently represents a hydrogen atom or a lower alkyl group of 1 to 5 carbon atoms.

It is preferable that at least one of $R^{1\prime}$ and $R^{2\prime}$ represent a hydrogen atom, and it is more preferable that both of $R^{1\prime}$ and $R^{2\prime}$ represent a hydrogen atom. n is preferably 0 or 1.

Examples of the tertiary alkyl ester-type acid dissociable, dissolution inhibiting group for X' are the same as the above-exemplified tertiary alkyl ester-type acid dissociable, dissolution inhibiting groups for $X^1$.

Examples of the aliphatic cyclic group for Y are the same as those exemplified above in connection with the explanation of "aliphatic cyclic group".

$Y^2$ is preferably an alkylene group of 1 to 10 carbon atoms or a divalent aliphatic cyclic group. As the aliphatic cyclic group, the same as those exemplified above in connection with the explanation of "aliphatic cyclic group" can be used, except that two hydrogen atoms have been removed therefrom. When $Y^2$ represents an alkylene group of 1 to 10 carbon atoms, it is more preferable that the number of carbons is 1 to 6, still more preferably 1 to 4, and most preferably 1 to 3. When $Y^2$ represents a divalent aliphatic cyclic group, it is particularly desirable that the divalent aliphatic cyclic group be a group in which two or more hydrogen atoms have been removed from cyclopentane, cyclohexane, norbornane, isobornane, adamantane, tricyclodecane or tetracyclododecane.

Specific examples of structural units represented by general formula (a1-1) to (a1-4) are shown below.

[Chemical Formula 30]

(a1-1-1)

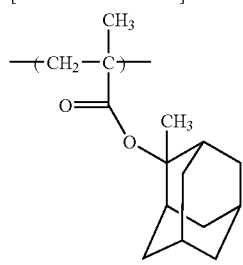

(a1-1-2)

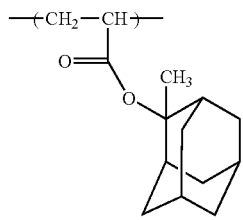

(a1-1-3)

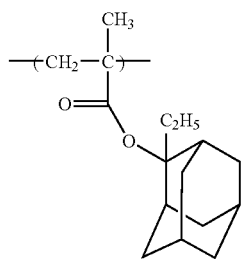

(a1-1-4)

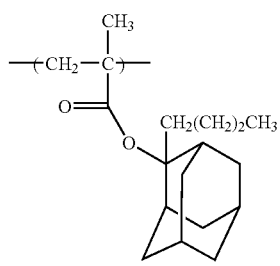

(a1-1-5)

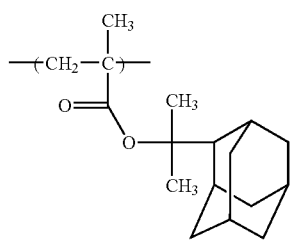

(a1-1-6)

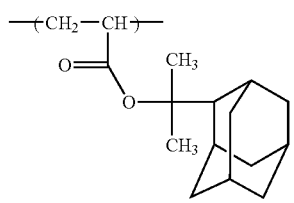

(a1-1-7)

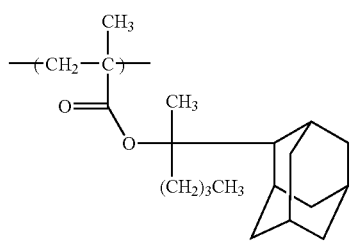

(a1-1-8)

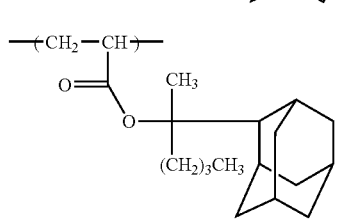

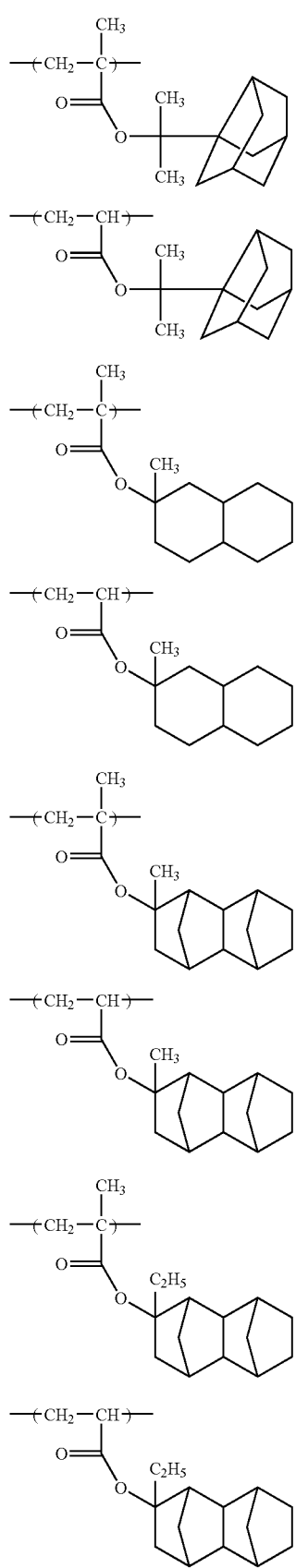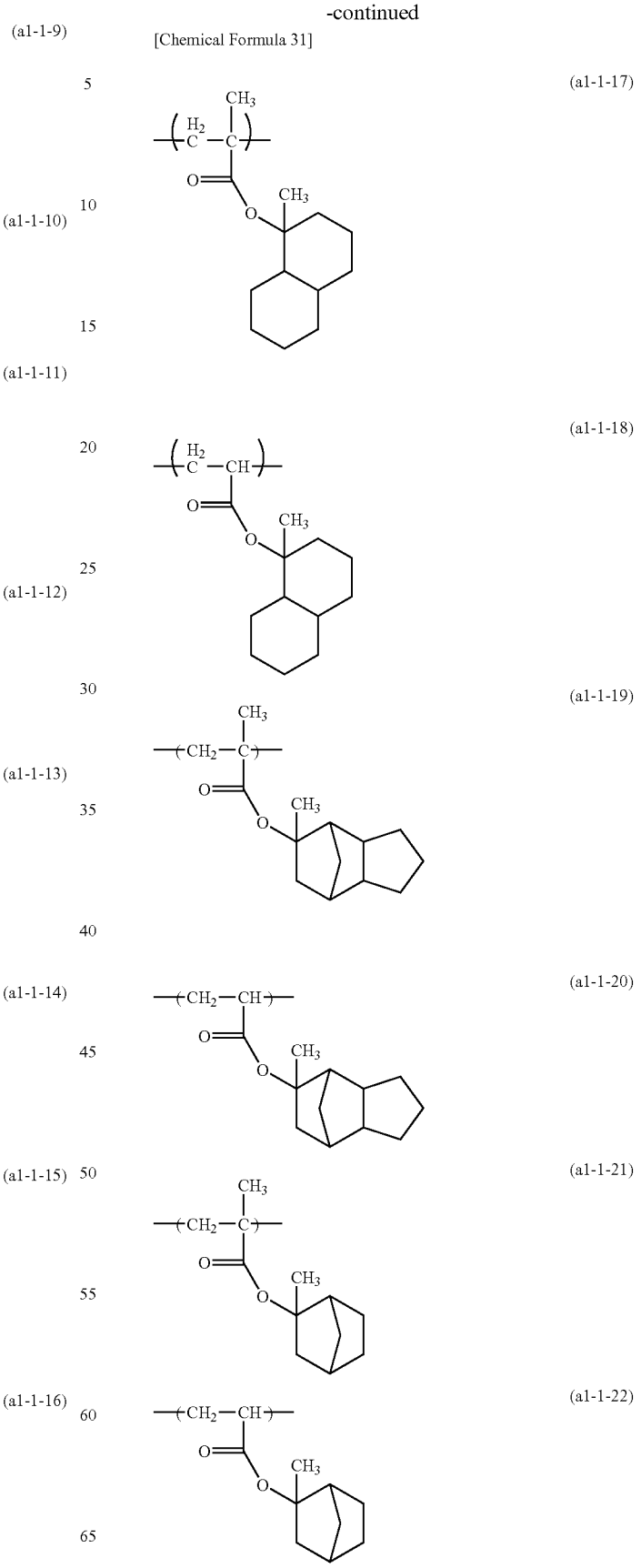

-continued
(a1-1-23)
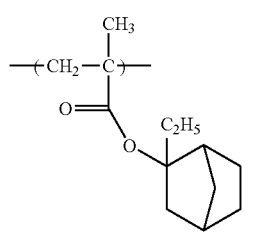
(a1-1-24)
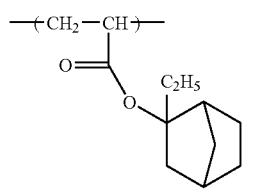
(a1-1-25)
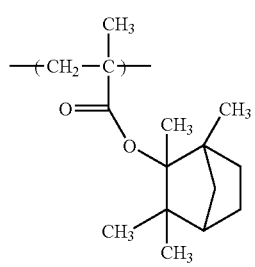
(a1-1-26)
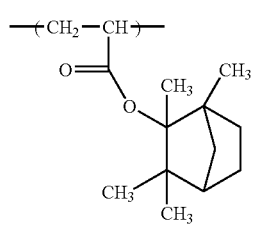
(a1-1-27)
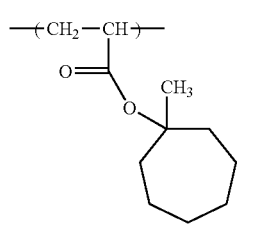
(a1-1-28)
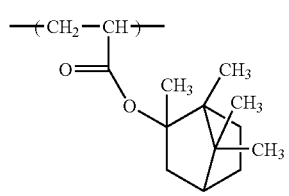
(a1-1-29)
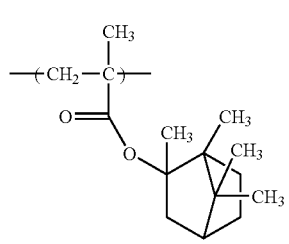
-continued
(a1-1-30)
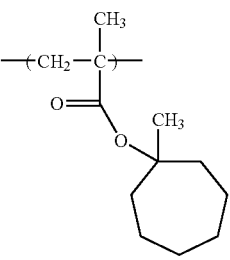
(a1-1-31)
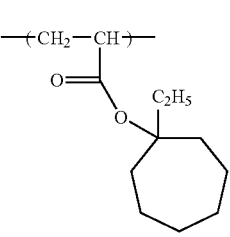
(a1-1-32)
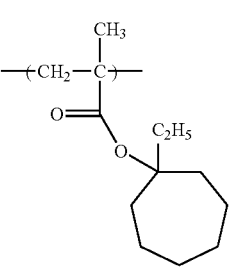
[Chemical Formula 32]
(a1-1-33)
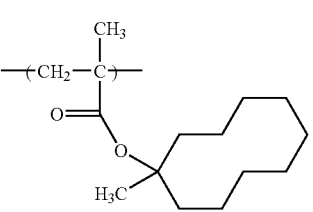
(a1-1-34)
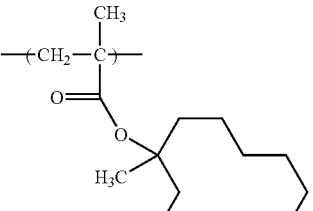
(a1-1-35)
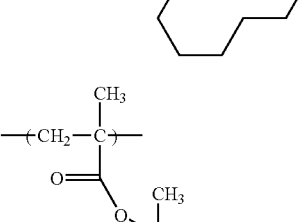

(a1-1-36) 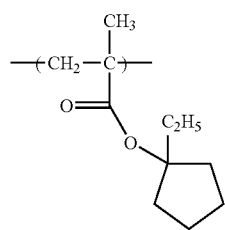
(a1-1-37) 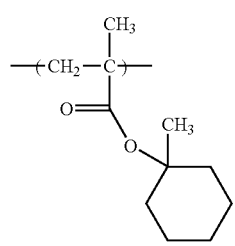
(a1-1-38) 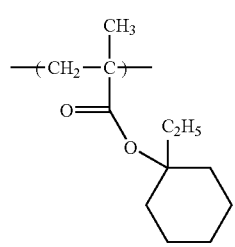
(a1-1-39) 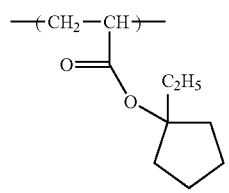
(a1-1-40) 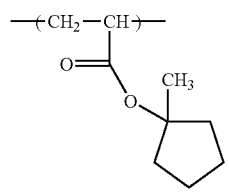
(a1-1-41) 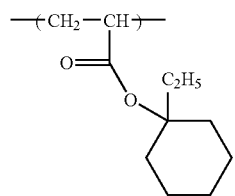
(a1-1-42) 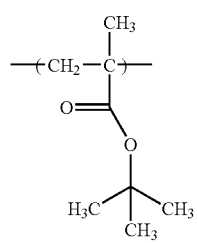
(a1-1-43) 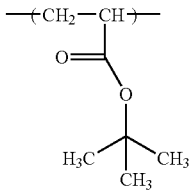
(a1-1-44) 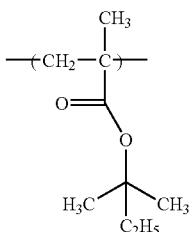
(a1-1-45) 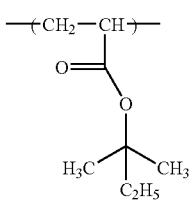
[Chemical Formula 33]
(a1-2-1) 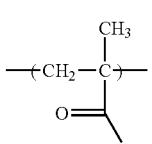
(a1-2-2) 
(a1-2-3) 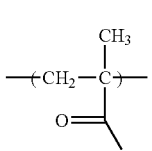
(a1-2-4) 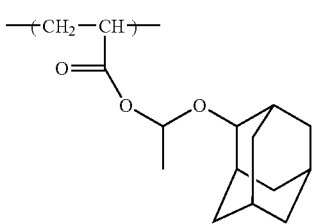

-continued
(a1-2-5)
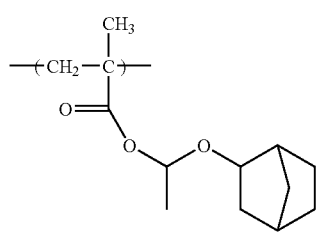
(a1-2-6)
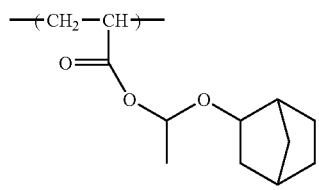
[Chemical Formula 34]
(a1-2-7)
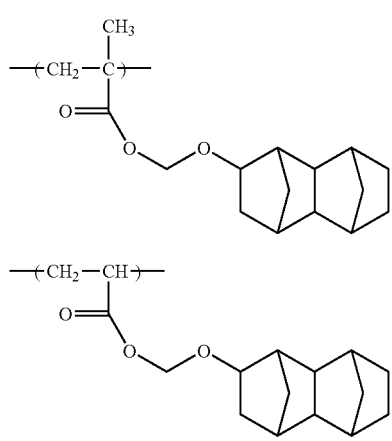
(a1-2-8)
(a1-2-9)
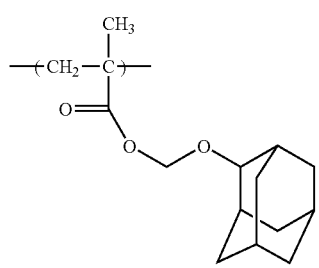
(a1-2-10)
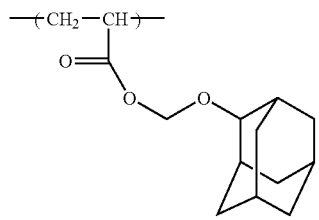
(a1-2-11)
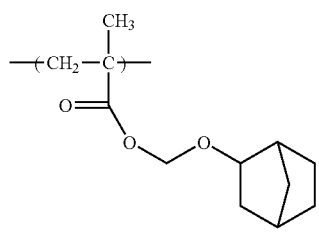
-continued
(a1-2-12)
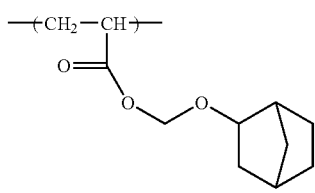
(a1-2-13)
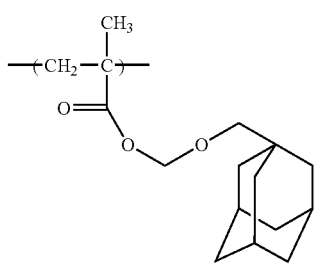
(a1-2-14)
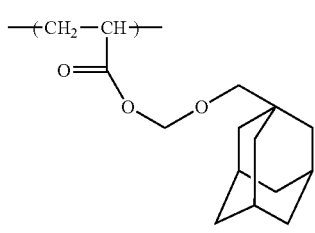
(a1-2-15)
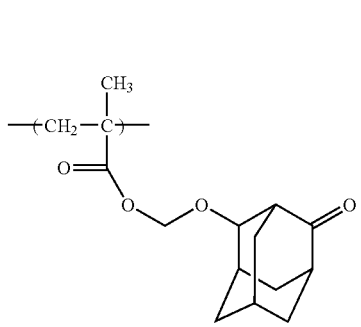
(a1-2-16)
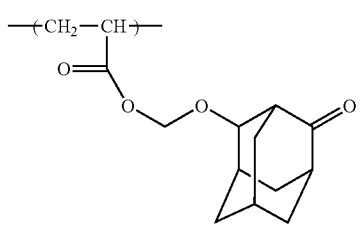
(a1-2-17)
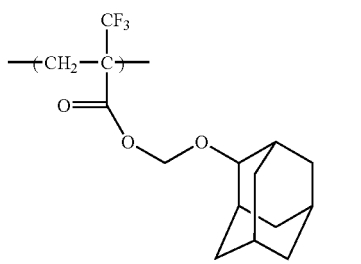

(a1-2-18) 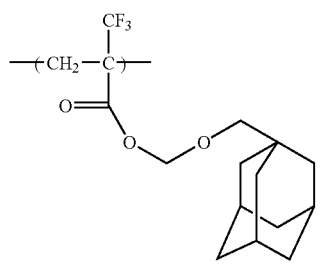
(a1-2-19) 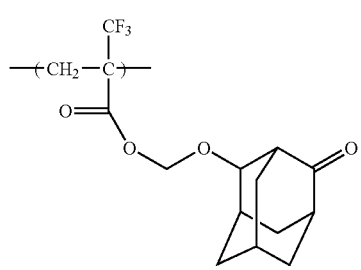
(a1-2-20) 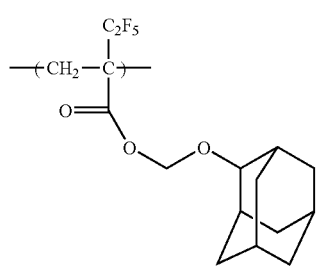
[Chemical Formula 35]
(a1-2-21) 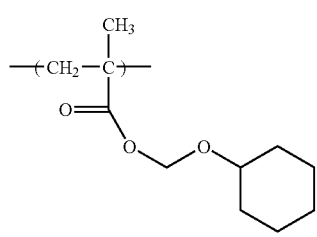
(a1-2-22) 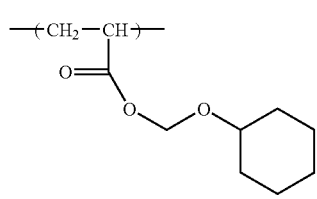
(a1-2-23) 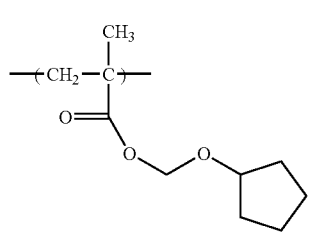
(a1-2-24) 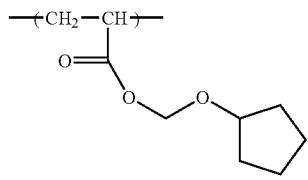
(a1-2-25) 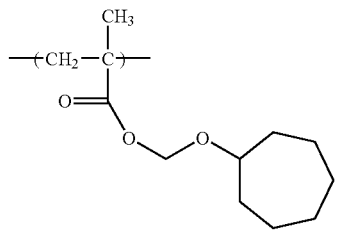
(a1-2-26) 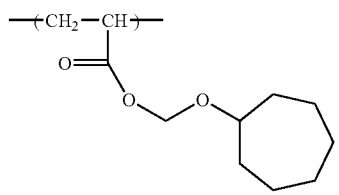
(a1-2-27) 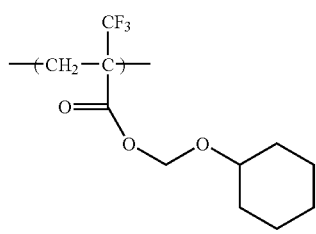
(a1-2-28) 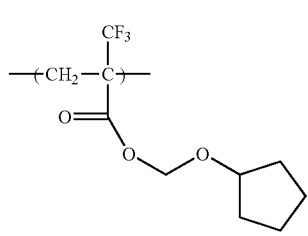
(a1-2-29) 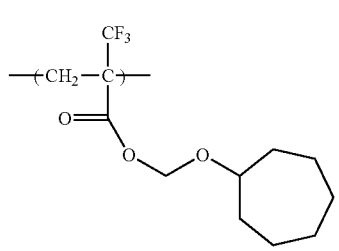
(a1-2-30) 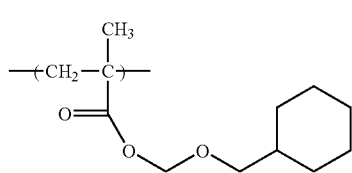

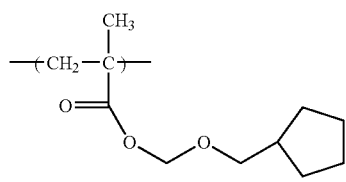 (a1-2-31)
[Chemical Formula 36]
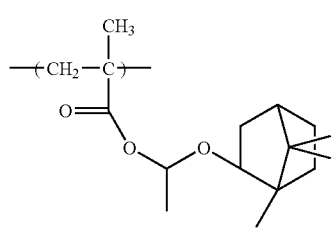 (a1-2-32)
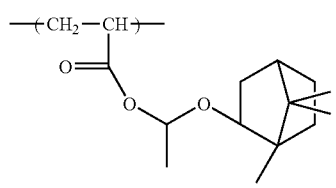 (a1-2-33)
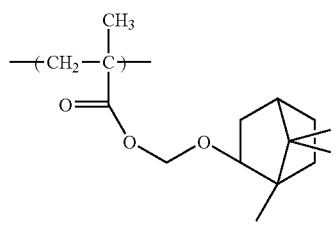 (a1-2-34)
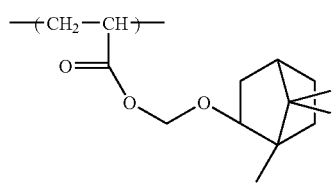 (a1-2-35)
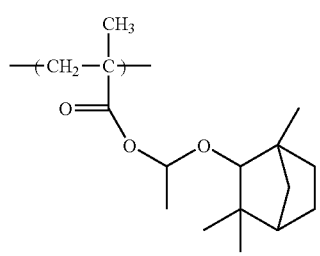 (a1-2-36)
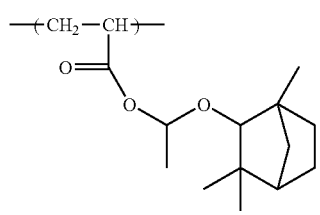 (a1-2-37)
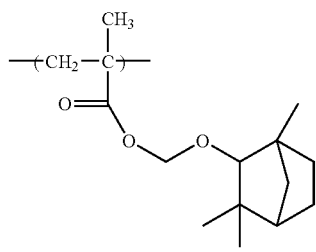 (a1-2-38)
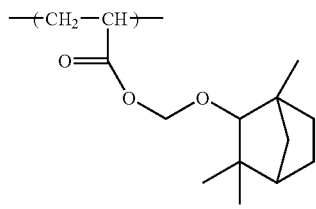 (a1-2-39)
[Chemical Formula 37]
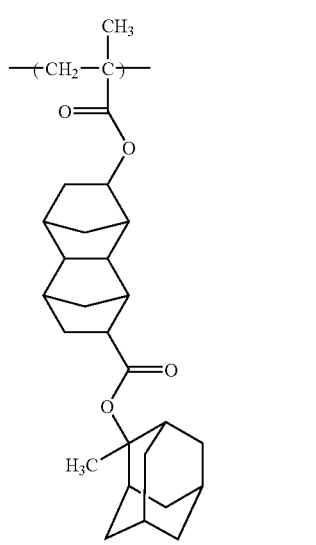 (a1-3-1)
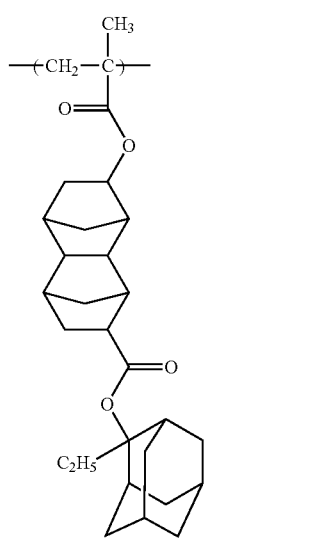 (a1-3-2)

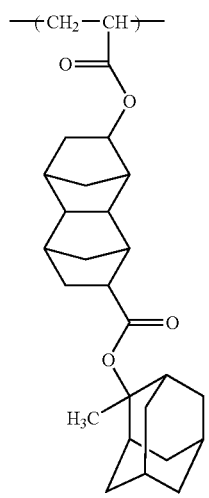 (a1-3-3)
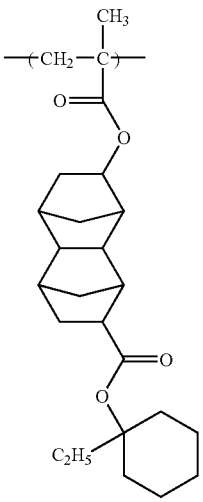 (a1-3-6)
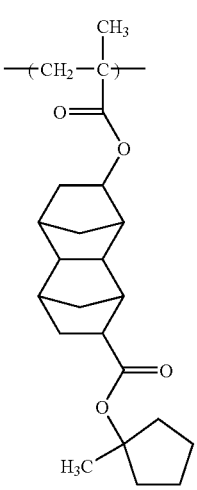 (a1-3-4)
(a1-3-7)
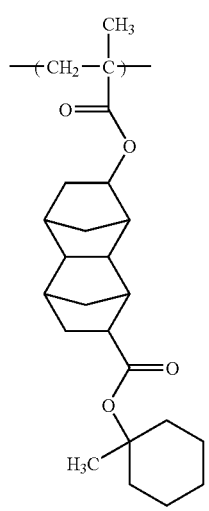 (a1-3-5)
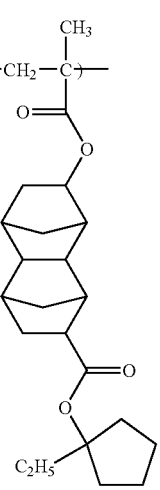 (a1-3-8)

-continued
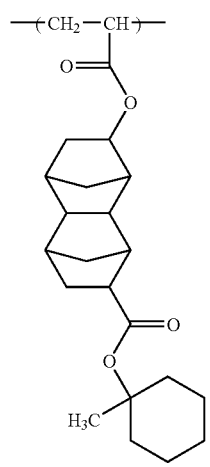 (a1-3-9)
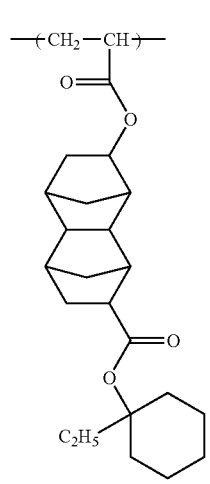 (a1-3-10)
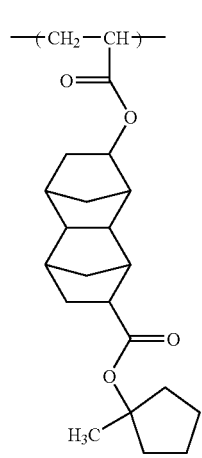 (a1-3-11)
-continued
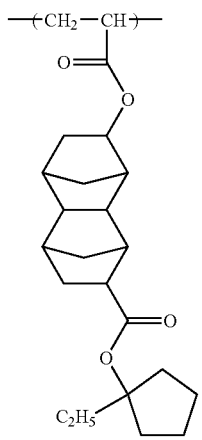 (a1-3-12)
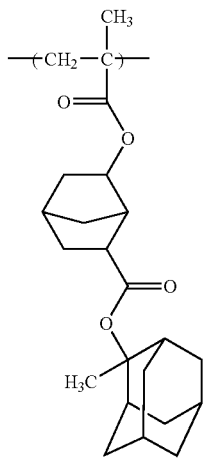 (a1-3-13)
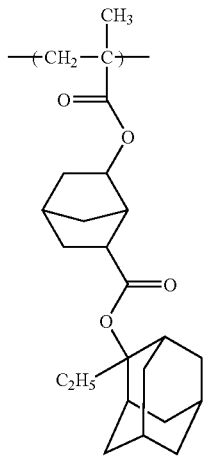 (a1-3-14)

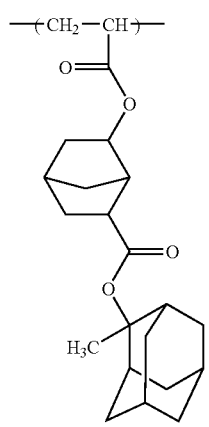 (a1-3-15)
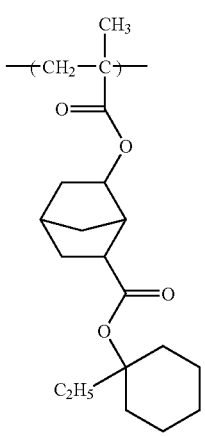 (a1-3-18)
[Chemical Formula 38]
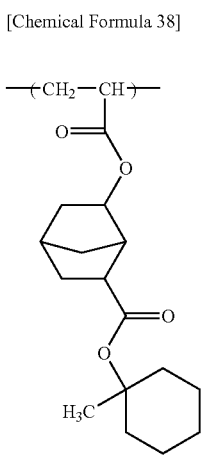 (a1-3-16)
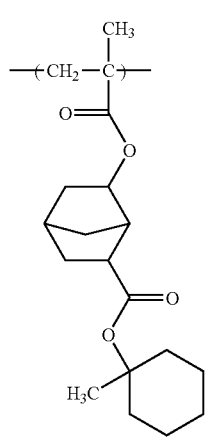 (a1-3-17)
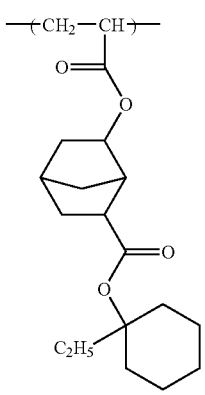 (a1-3-19)
(a1-3-20)

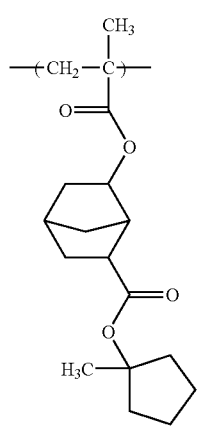
(a1-3-21)
(a1-3-22)
(a1-3-23)
(a1-3-24)
[Chemical Formula 39]
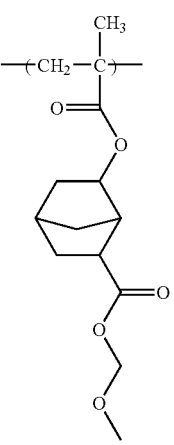
(a1-4-1)
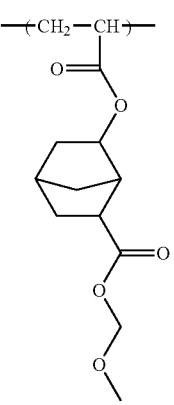
(a1-4-2)
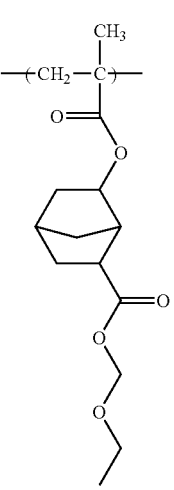
(a1-4-3)

-continued
(a1-4-4)
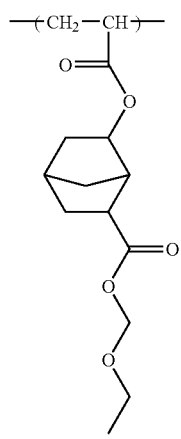
(a1-4-5)
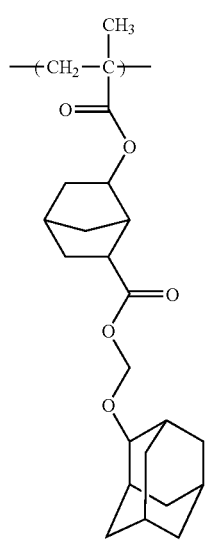
(a1-4-6)
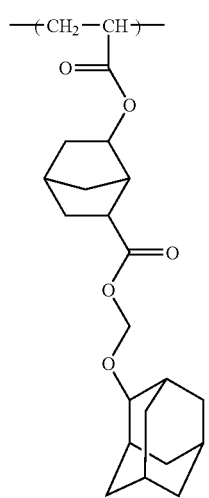
-continued
(a1-4-7)
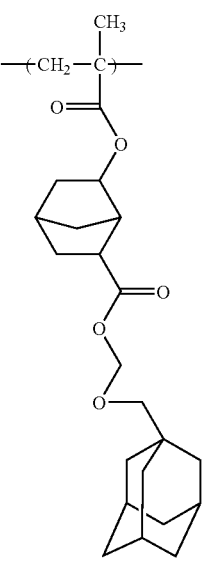
(a1-4-8)
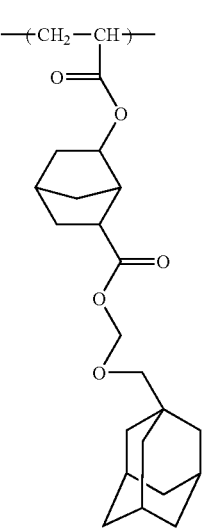
(a1-4-9)
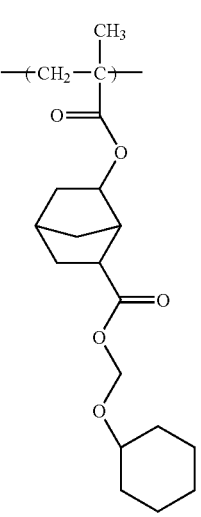

-continued
(a1-4-10)
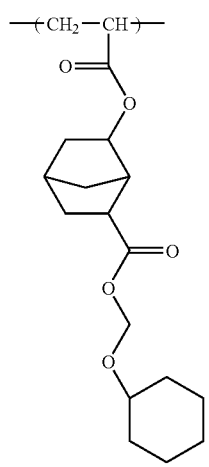
(a1-4-11)
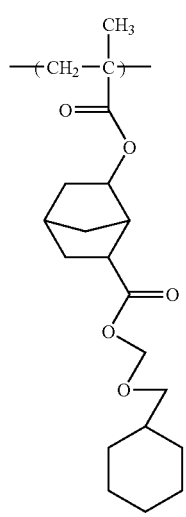
(a1-4-12)
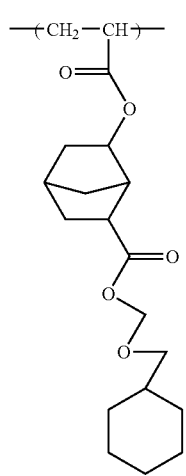
-continued
(a1-4-13)
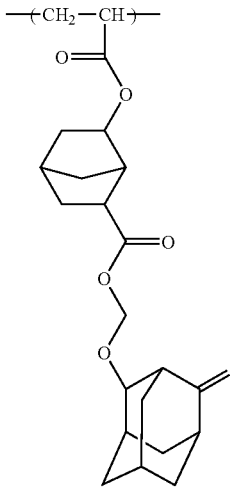
(a1-4-14)
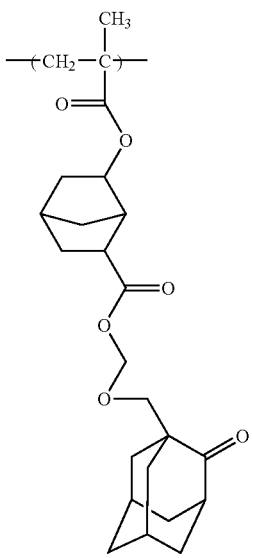
(a1-4-15)
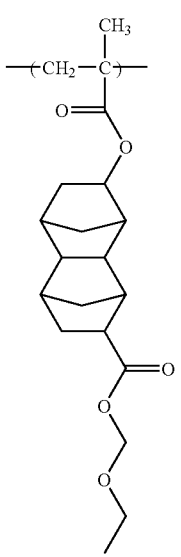

(a1-4-16)
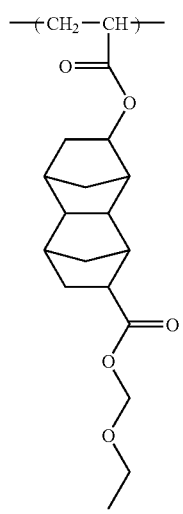
(a1-4-17)
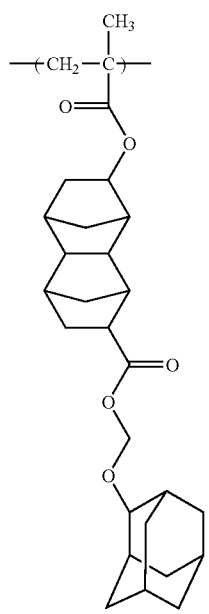
[Chemical Formula 40]
(a1-4-18)
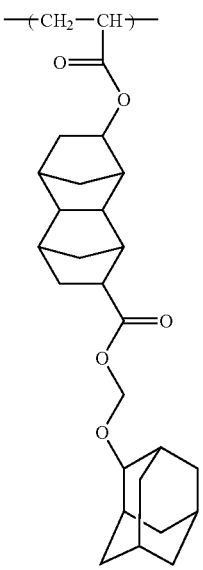
(a1-4-19)
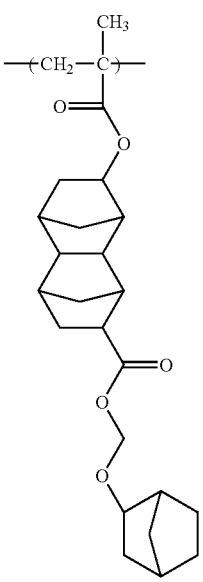

(a1-4-20)
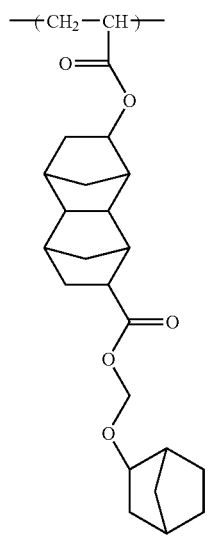
(a1-4-21)
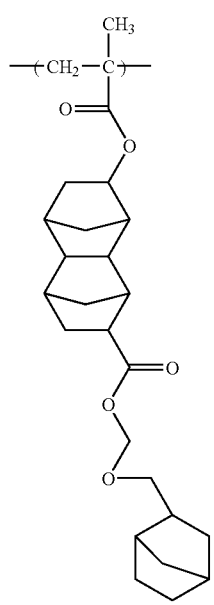
(a1-4-22)
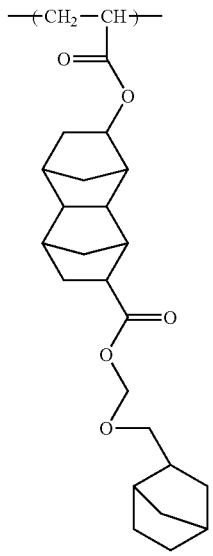
(a1-4-23)
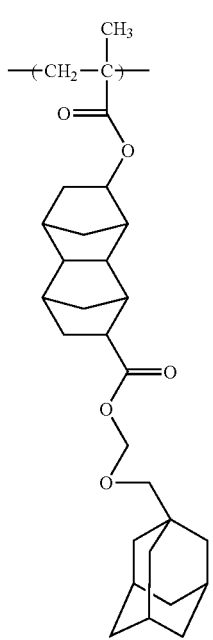

(a1-4-24) 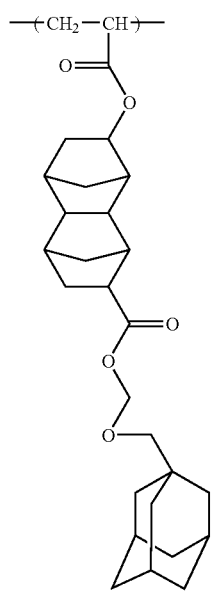
(a1-4-26) 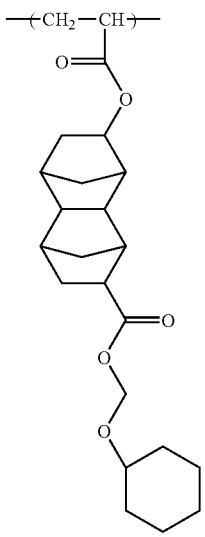
(a1-4-25) 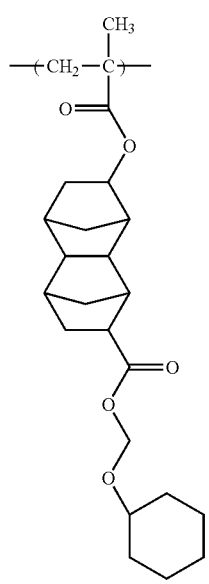
(a1-4-27) 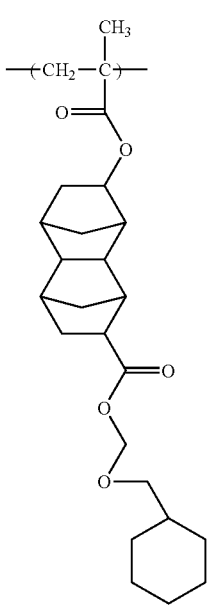

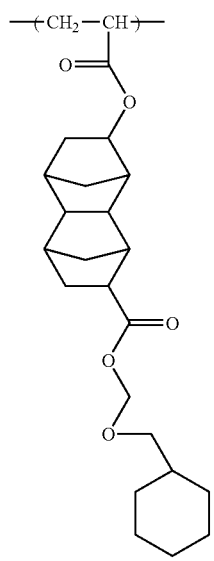
(a1-4-28)
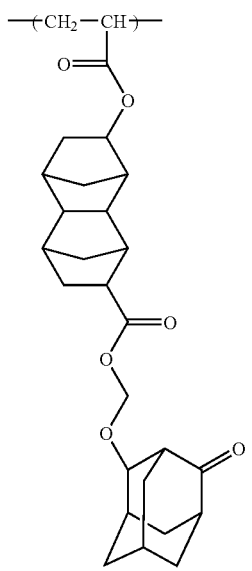
(a1-4-30)
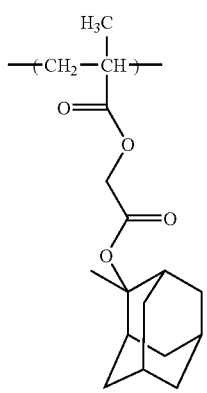
(a1-4-29)
(a1-4-31)
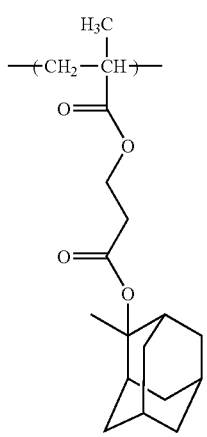
(a1-4-32)

(a1-4-33) 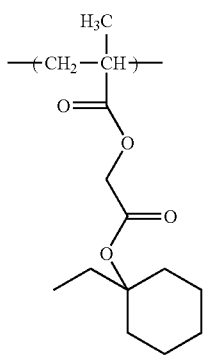
(a1-4-34) 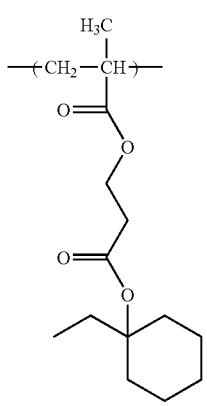
(a1-4-35) 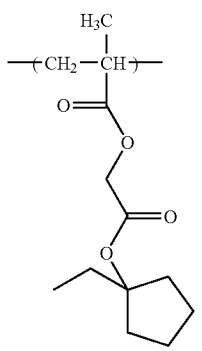
(a1-4-36) 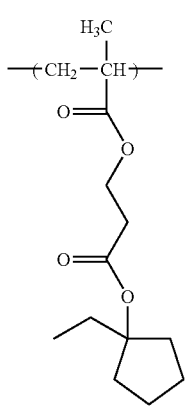
(a1-4-37) 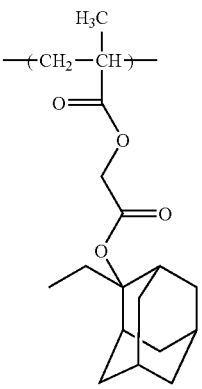
(a1-4-38) 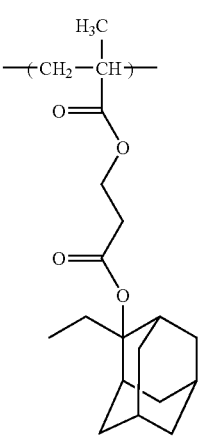
(a1-4-39) 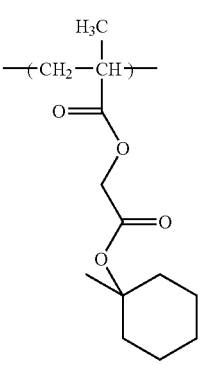
(a1-4-40) 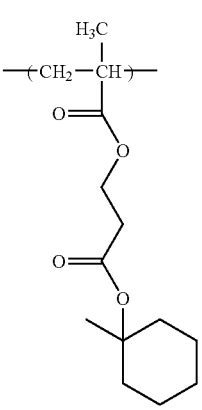

-continued (a1-4-41)

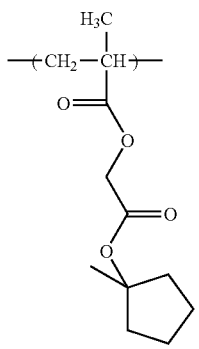

(a1-4-42)

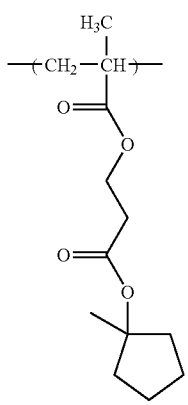

As the structural unit (a1), one type may be used alone, or two or more types may be used in combination.

Among these, structural units represented by general formula (a1-1) are preferable. More specifically, at least one structural unit selected from the group consisting of structural units represented by formulas (a1-1-1) to (a-1-6) and (a1-1-35) to (a1-1-41) is more preferable.

Further, as the structural unit (a1), structural units represented by general formula (a1-1-01) shown below which includes the structural units represented by formulas (a1-1-1) to (a1-1-4), and structural units represented by general formula (a1-1-02) shown below which includes the structural units represented by formulas (a1-1-35) to (a1-1-41) are also preferable.

[Chemical Formula 41]

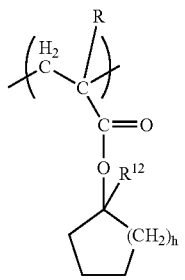

(a1-1-01)

wherein R represents a hydrogen atom, a lower alkyl group or a halogenated lower alkyl group; and $R^{11}$ represents a lower alkyl group.

[Chemical Formula 42]

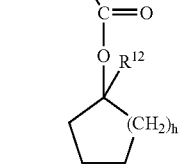

(a1-1-02)

wherein R represents a hydrogen atom, a lower alkyl group or a halogenated lower alkyl group; $R^{12}$ represents a lower alkyl group; and h represents an integer of 1 to 3.

In general formula (a1-1-01), R is as defined above. The lower alkyl group for $R^{11}$ is the same as the lower alkyl group for R above, and is preferably a methyl group or an ethyl group.

In general formula (a1-1-02), R is a defined above. The lower alkyl group for $R^{12}$ is the same as the lower alkyl group for R above. $R^{12}$ is preferably 1 or 2, and most Preferably 2.

In the component (A1), the amount of the structural unit (a1) based on the Combined total of all structural units constituting the component (A1) is preferably 10 to 80 mol %, more preferably 20 to 70 mol %, and still more preferably 25 to 50 mol %. By making the amount of the structural unit (a1) at least as large as the lower limit of the above-mentioned range, a pattern can be easily formed using a positive resist composition prepared from the component (A1). On the other hand, by making the amount of the structural unit (a1) no more than the upper limit of the above-mentioned range, a good balance can be achieved with the other structural units.

—Structural Unit (a2)

In the present invention, the component (A1) preferably has a structural unit (a2) derived from an acrylate ester having a lactone-containing cyclic group, as well as the structural unit (a1).

The term "lactone-containing cyclic group" refers to a cyclic group including one ring containing a —O—C(O)— structure (lactone ring). The term "lactone ring" refers to a single ring containing a —O—C(O)— structure, and this ring is counted as the first ring. A lactone-containing cyclic group in which the only ring structure is the lactone ring is referred to as a monocyclic group, and groups containing other ring structures are described as polycyclic groups regardless of the structure of the other rings.

When the component (A1) is used for forming a resist film, the lactone-containing cyclic group of the structural unit (a2) is effective in improving the adhesion between the resist film and the substrate, and increasing the affinity for the developing solution containing water.

As the structural unit (a2), there is no particular limitation, and an arbitrary structural unit may be used.

Specific examples of lactone-containing monocyclic groups include groups in which one hydrogen atom has been removed from γ-butyrolactone. Further, specific examples of lactone-containing polycyclic groups include groups in which one hydrogen atom has been removed from a lactone ring-containing bicycloalkane, tricycloalkane or tetracycloalkane.

More specifically, examples of the structural unit (a2) include structural units represented by general formulas (a2-1) to (a2-5) shown below.

[Chemical Formula 43]

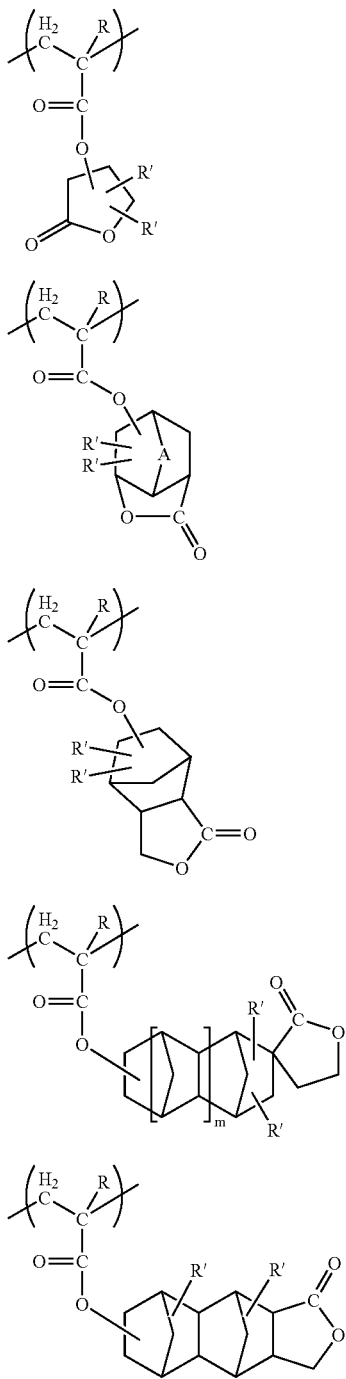

wherein R represents a hydrogen atom, a lower alkyl group or a halogenated lower alkyl group; R' represents a hydrogen atom, a lower alkyl group or an alkoxy group of 1 to 5 carbon atoms; m represents 0 or 1; and A represents an alkylene group of 1 to 5 carbon atoms or an oxygen atom.

In general formulas (a2-1) to (a2-5), R is the same as R in the structural unit (a1).

The lower alkyl group for R' is the same as the lower alkyl group for R in the structural unit (a1).

Specific examples of alkylene groups of 1 to 5 carbon atoms for A include a methylene group, ethylene group, n-propylene group and isopropylene group.

In the structural units represented by general formulas (a2-1) to (a2-5), in consideration of industrial availability, R' is preferably a hydrogen atom.

Specific examples of structural units represented by general formulas (a2-1) to (a2-5) above are shown below.

[Chemical Formula 44]

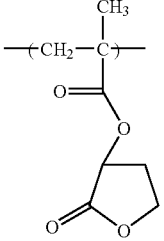

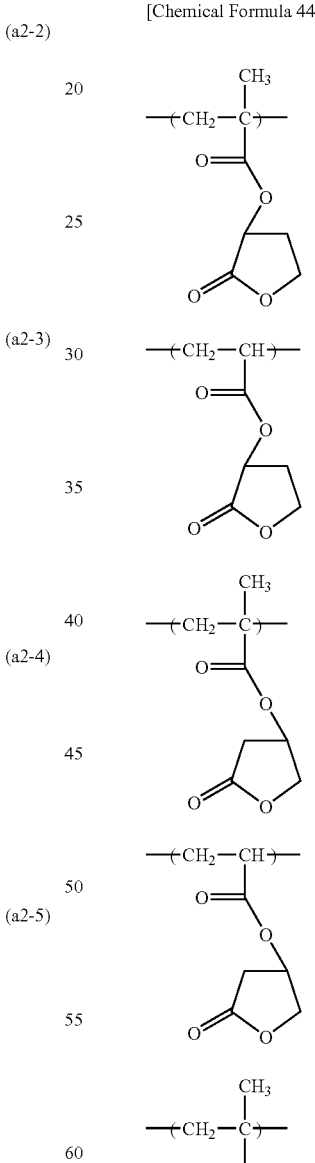

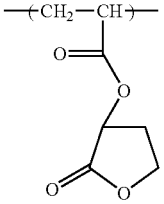

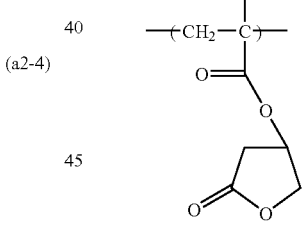

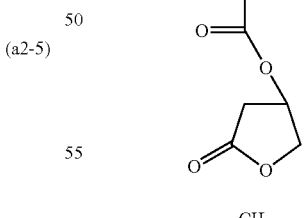

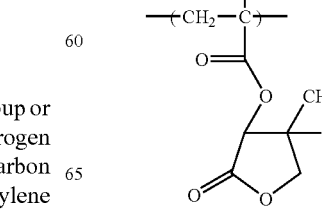

(a2-1-6)
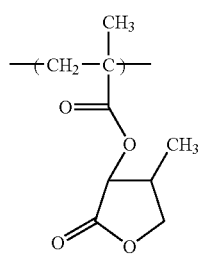
[Chemical Formula 45]
(a2-2-1)
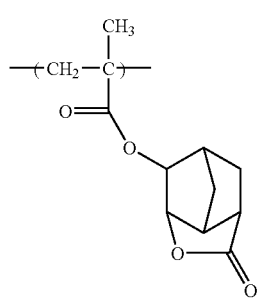
(a2-2-2)
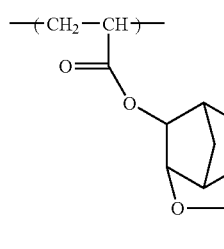
(a2-2-3)
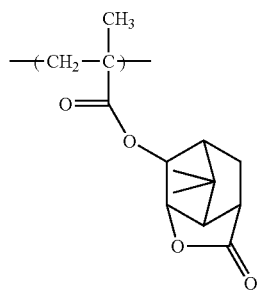
(a2-2-4)
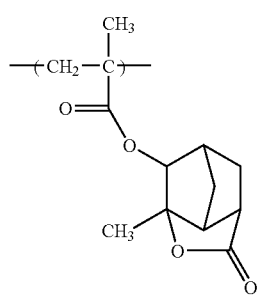
(a2-2-5)
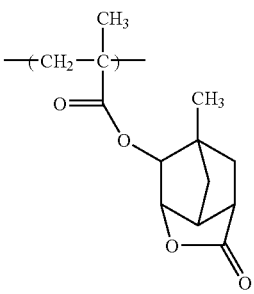
(a2-2-6)
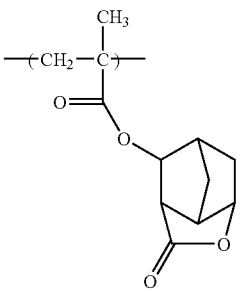
(a2-2-7)
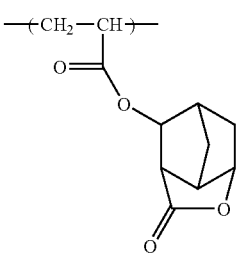
(a2-2-8)
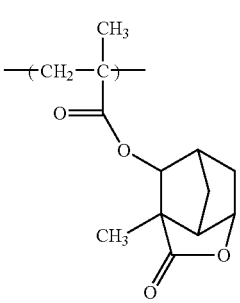
(a2-2-9)
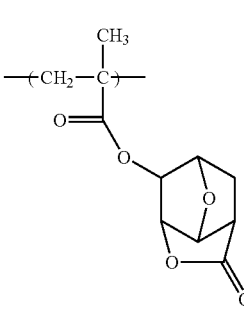

-continued
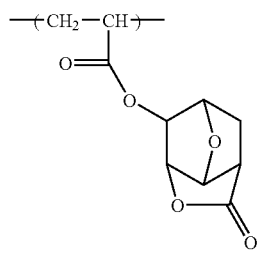
(a2-2-10)
[Chemical Formula 46]
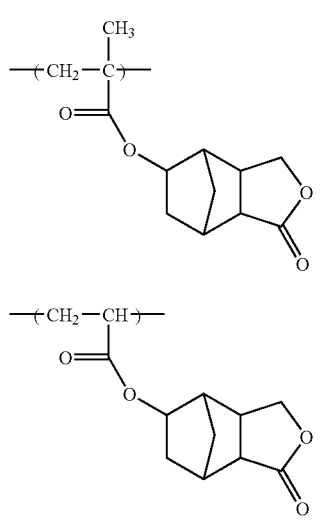
(a2-3-1)
(a2-3-2)
(a2-3-3)
(a2-3-4)
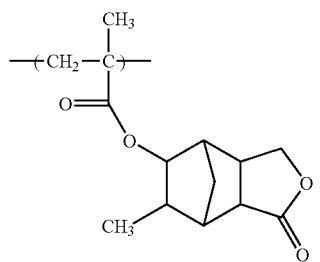
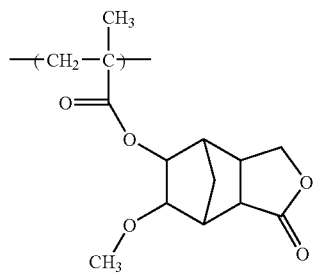
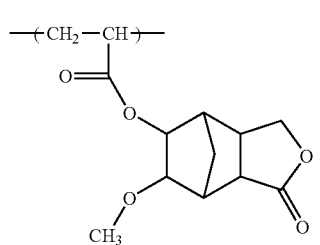
(a2-3-5)
-continued
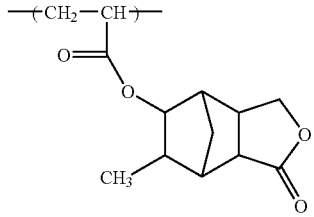
(a2-3-6)
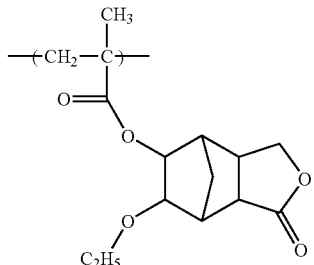
(a2-3-7)
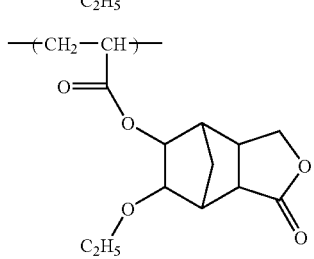
(a2-3-8)
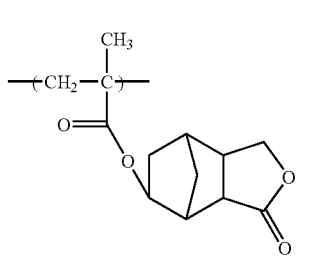
(a2-3-9)
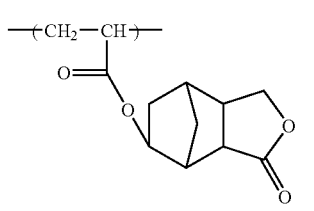
(a2-3-10)
[Chemical Formula 47]
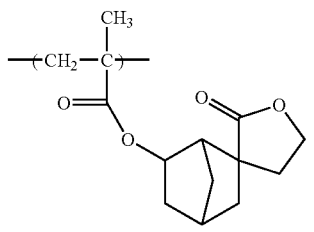
(a2-4-1)

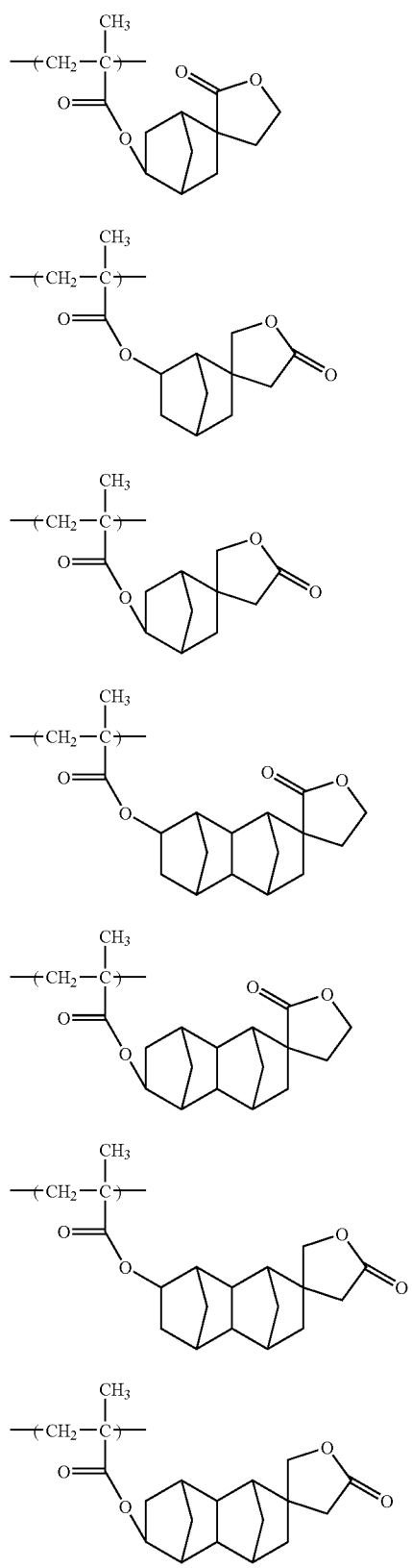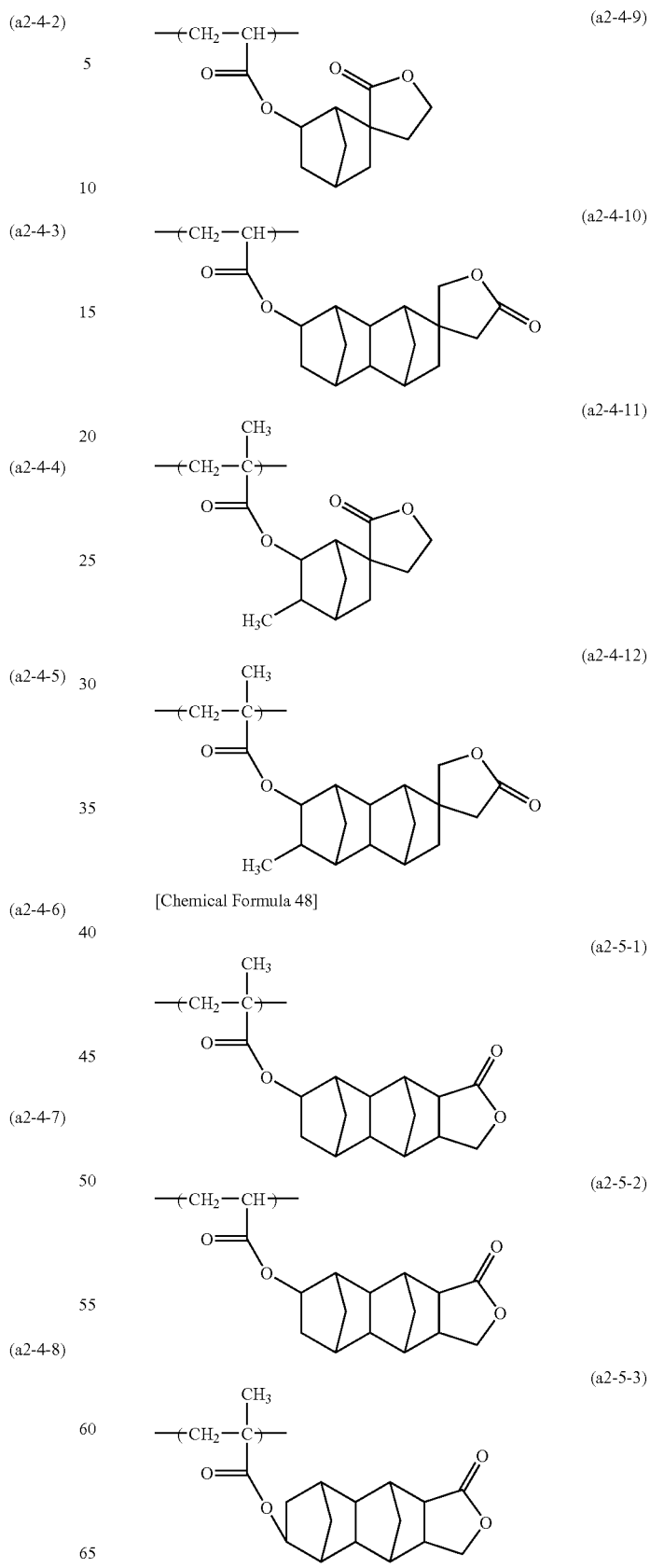

-continued

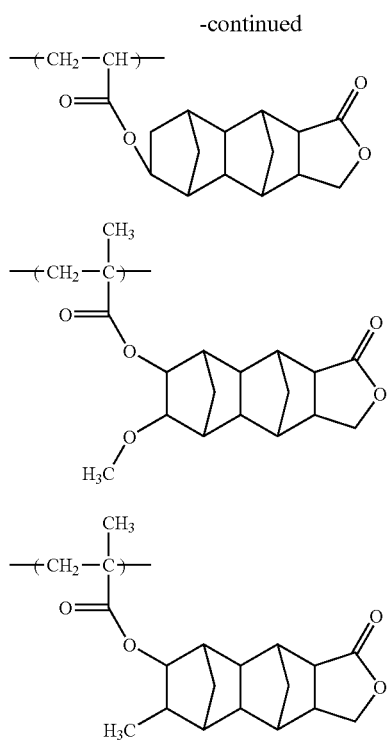

(a2-5-4)

(a2-5-5)

(a2-5-6)

Of these, at least one structural unit selected from the group consisting of formulas (a2-1) to (a2-5) is preferable, and at least one structural unit selected from the group consisting of formulas (a2-1) to (a2-3) is more preferable. Specifically, it is preferable to use at least one structural unit selected from the group consisting of formulas (a2-1-1), (a2-1-2), (a2-2-1), (a2-2-2), (a2-3-1), (a2-3-2), (a2-3-9) and (a2-3-10).

In the component (A1), as the structural unit (a2), one type of structural unit may be used, or two or more types may be used in combination.

In the component (A1), the amount of the structural unit (a2) based on the combined total of all structural units constituting the component (A1) is preferably 5 to 60 mol %, more preferably 10 to 50 mol %, and still more preferably 20 to 50 mol %. By making the amount of the structural unit (a2) at least as large as the lower limit of the above-mentioned range, the effect of using the structural unit (a2) can be satisfactorily achieved. On the other hand, by making the amount of the structural unit (a2) no more than the upper limit of the above-mentioned range, a good balance can be achieved with the other structural units.

—Structural Unit (a3)

The component (A1) preferably has a structural unit (a3) derived from an acrylate ester having a polar group-containing aliphatic hydrocarbon group, as well as the structural unit (a1) and the structural unit (a2). By including the structural unit (a3), the hydrophilicity of the component (A1) is improved, and hence, the affinity of the component (A1) for the developing solution is improved. As a result, the solubility of the exposed portions in an alkali developing solution improves, which contributes to favorable improvements in the resolution.

Examples of the polar group include a hydroxyl group, cyano group, carboxyl group, or hydroxyalkyl group in which some of the hydrogen atoms of the alkyl group have been substituted with fluorine atoms, although a hydroxyl group is particularly desirable.

Examples of the aliphatic hydrocarbon group include linear or branched hydrocarbon groups (and preferably alkylene groups) of 1 to 10 carbon atoms, and polycyclic aliphatic hydrocarbon groups (polycyclic groups). These polycyclic groups can be selected appropriately from the multitude of groups that have been proposed for the resins of resist compositions designed for use with ArF excimer lasers. The polycyclic group preferably has 7 to 30 carbon atoms.

Of the various possibilities, structural units derived from an acrylate ester that include an aliphatic polycyclic group that contains a hydroxyl group, cyano group, carboxyl group or a hydroxyalkyl group in which some of the hydrogen atoms of the alkyl group have been substituted with fluorine atoms are particularly desirable. Examples of polycyclic groups include groups in which two or more hydrogen atoms have been removed from a bicycloalkane, tricycloalkane, tetracycloalkane or the like. Specific examples include groups in which two or more hydrogen atoms have been removed from a polycycloalkane such as adamantane, norbornane, isobornane, tricyclodecane or tetracyclododecane. Of these polycyclic groups, groups in which two or more hydrogen atoms have been removed from adamantane, norbornane or tetracyclododecane are preferred industrially.

When the aliphatic hydrocarbon group within the polar group-containing aliphatic hydrocarbon group is a linear or branched hydrocarbon group of 1 to 10 carbon atoms, the structural unit (a3) is preferably a structural unit derived from a hydroxyethyl ester of acrylic acid. On the other hand, when the hydrocarbon group is a polycyclic group, structural units represented by formulas (a3-1), (a3-2), and (a3-3) shown below are preferable.

[Chemical Formula 49]

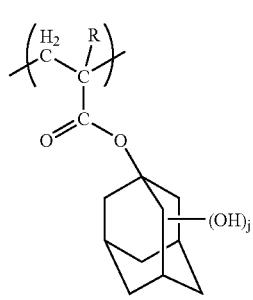

(a3-1)

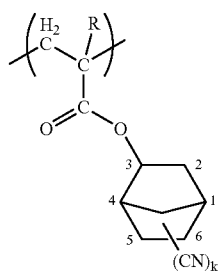

(a3-2)

-continued (a3-3)

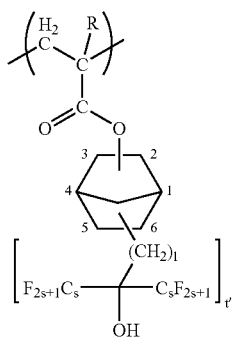

wherein R is as defined above; j is an integer of 1 to 3; k is an integer of 1 to 3; t' is an integer of 1 to 3; 1 is an integer of 1 to 5; and s is an integer of 1 to 3.

In formula (a3-1), j is preferably 1 or 2, and more preferably 1. When j is 2, it is preferable that the hydroxyl groups be bonded to the 3rd and 5th positions of the adamantyl group. When j is 1, it is preferable that the hydroxyl group be bonded to the 3rd position of the adamantyl group.

j is preferably 1, and it is particularly desirable that the hydroxyl group be bonded to the 3rd position of the adamantyl group.

In formula (a3-2), k is preferably 1. The cyano group is preferably bonded to the 5th or 6th position of the norbonyl group.

In formula (a3-3), t' is preferably 1, 1 is preferably 1 and s is preferably 1. Further, in formula (a3-3), it is preferable that a 2-norbonyl group or 3-norbonyl group be bonded to the terminal of the carboxy group of the acrylic acid. The fluorinated alkyl alcohol is preferably bonded to the 5th or 6th position of the norbonyl group.

In the component (A1), as the structural unit (a3), one type of structural unit may be used, or two or more types may be used in combination.

When the component (A1) contains the structural unit (a3), the amount of structural unit (a3) based on the combined total of all structural units constituting the component (A1) is preferably 5 to 50 mol %, more preferably 5 to 40 mol %, and still more preferably 5 to 25 mol %. By making the amount of the structural unit (a3) at least as large as the lower limit of the above-mentioned range, the effect of using the structural unit (a3) can be satisfactorily achieved. On the other hand, by making the amount of the structural unit (a3) no more than the upper limit of the above-mentioned range, a good balance can be achieved with the other structural units.

—Structural Unit (a4)

The component (A1) may also have a structural unit (a4) which is other than the above-mentioned structural units (a1) to (a3), as long as the effects of the present invention are not impaired.

As the structural unit (a4), any other structural unit which cannot be classified as one of the above structural units (a1) to (a3) can be used without any particular limitations, and any of the multitude of conventional structural units used within resist resins for ArF excimer lasers or KrF excimer lasers (and particularly for ArF excimer lasers) can be used.

As the structural unit (a4), a structural unit which contains a non-acid-dissociable aliphatic polycyclic group, and is also derived from an acrylate ester is preferable. Examples of this polycyclic group include the same groups as those described above in connection with the aforementioned structural unit (a1), and any of the multitude of conventional polycyclic groups used within the resin component of resist compositions for ArF excimer lasers or KrF excimer lasers (and particularly for ArF excimer lasers) can be used.

In consideration of industrial availability and the like, at least one polycyclic group selected from amongst a tricyclodecanyl group, adamantyl group, tetracyclododecanyl group, isobornyl group, and norbornyl group is particularly desirable. These polycyclic groups may be substituted with a linear or branched alkyl group of 1 to 5 carbon atoms.

Specific examples of the structural unit (a4) include units with structures represented by general formulas (a4-1) to (a4-5) shown below.

[Chemical Formula 50]

(a4-1)

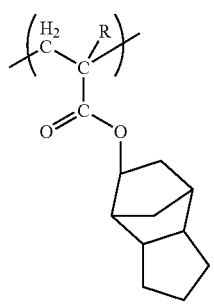

(a4-2)

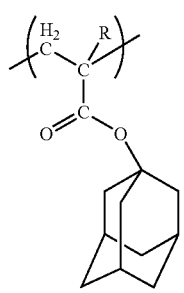

(a4-3)

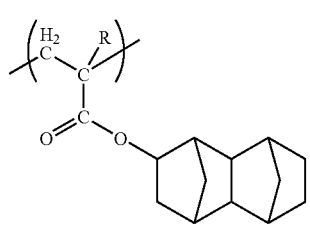

(a4-4)

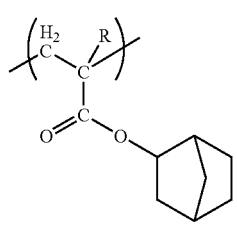

-continued (a4-5)

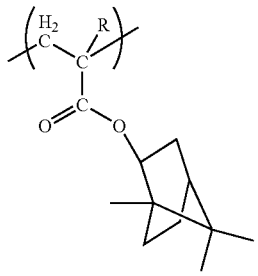

wherein R is as defined above.

When the structural unit (a4) is included in the component (A1), the amount of the structural unit (a4) based on the combined total of all the structural units that constitute the component (A1) is preferably within the range from 1 to 30 mol %, and more preferably from 10 to 20 mol %.

In the present invention, the component (A1) is a resin component (polymer) which exhibits increased solubility in an alkali developing solution under action of acid. As such a resin component (polymer), a copolymer having the structural units (a1), (a2) and (a3) can be preferably used. Examples of such a copolymer include a copolymer consisting of the structural units (a1) and (a2) and (a3), and a copolymer consisting of the structural units (a1), (a2), (a3) and (a4).

In the present invention, as the component (A1), a copolymer (A1-1) including a combination of structural units represented by general formula (A1-1) shown below or a copolymer (A1-2) including a combination of structural units represented by general formula (A1-2) shown below is preferable.

[Chemical Formula 51]

(A1-1)

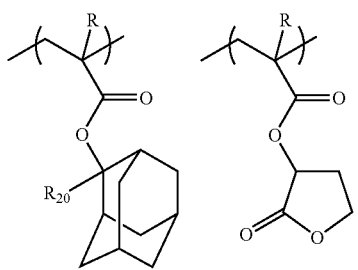

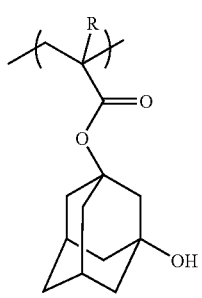

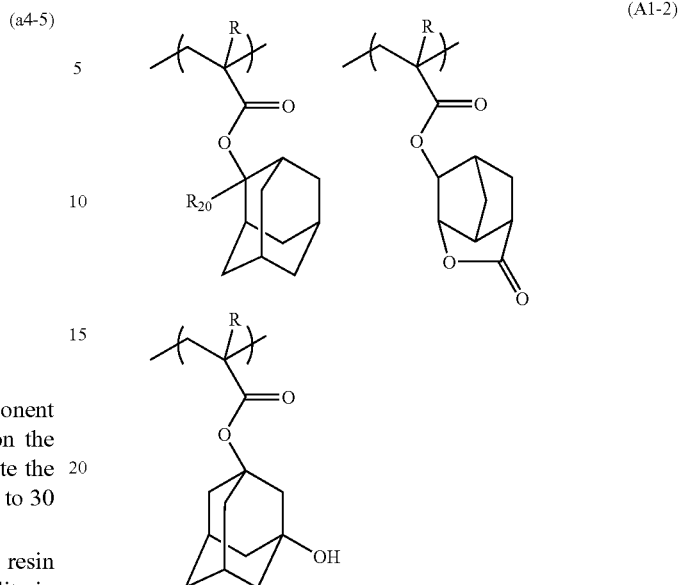

wherein R is as defined above; and $R^{20}$ represents a lower alkyl group.

In general formulas (A1-1) and (A1-2), R is as defined above, and is preferably a hydrogen atom or a methyl group.

In general formulas (A1-1) and (A1-2), $R^{20}$ represents a lower alkyl group, and is preferably a methyl group or ethyl group.

In the component (A1), as the copolymer (A1-1) or (A1-2), one type of copolymer may be used, or two or more types may be used in combination.

In the component (A1), the content of the copolymer (A1-1) or (A1-2) is preferably 70% by weight or more, more preferably 80% by weight or more, and may be even 100% by weight. It is particularly desirable that the content of the copolymer (A1-1) or (A1-2) be 100% by weight. By making the content at least as large as the lower limit of the above-mentioned range, the lithography properties as a positive resist composition are improved.

The component (A1) can be obtained, for example, by a conventional radical polymerization or the like of the monomers corresponding with each of the structural units, using a radical polymerization initiator such as azobisisobutyronitrile (AIBN).

Furthermore, in the component (A1), by using a chain transfer agent such as HS—$CH_2$—$CH_2$—$CH_2$—$C(CF_3)_2$—OH, a —$C(CF_3)_2$—OH group can be introduced at the terminals of the component (A1). Such a copolymer having introduced a hydroxyalkyl group in which some of the hydrogen atoms of the alkyl group are substituted with fluorine atoms is effective in reducing developing defects and LER (line edge roughness: unevenness of the side walls of a line pattern).

The weight average molecular weight (Mw) (the polystyrene equivalent value determined by gel permeation chromatography) of the component (A1) is not particularly limited, but is preferably 2,000 to 50,000, more preferably 3,000 to 30,000, still more preferably 4,000 to 20,000, and most preferably 5,000 to 20,000. By making the weight average molecular weight no more than the upper limit of the above-mentioned range, the component (A1) exhibits satisfactory solubility in a resist solvent when used as a resist. On the other hand, by making the weight average molecular weight at least as large as the lower limit of the above-mentioned range, dry etching resistance and cross-sectional shape of the resist pattern becomes satisfactory.

Further, the dispersity (Mw/Mn) is preferably 1.0 to 5.0, more preferably 1.0 to 3.0, and most preferably 1.2 to 2.5. Here, Mn is the number average molecular weight.

Further, as the component (A1), an alkali-soluble resin component other than the copolymers (A1-1) and (A1-2), such as other polymeric compounds used in conventional resist compositions may be used.

In the resist composition of the present invention, the amount of the component (A1) can be appropriately adjusted depending on the thickness of the resist film to be formed, and the like.

<Component (B)>

In the resist composition of the present invention, the component (B) contains an acid generator (B1) (hereafter, referred to as "component (B1)") including a compound represented by general formula (b1-8) above or an acid generator (B1') (hereafter, referred to as "component (B1')") including a compound represented by general formula (b1-9) above. In general formula (b1-8), as $R^{410}$, $R^{41}$, $R^{42}$, $R^{43}$, Q, $n_0$, $n_1$, $n_2$, $n_3$ and $X^-$, the same as those described above in connection with the compound of the third aspect of the present invention can be exemplified. Further, in general formula (b1-9), as $R^{402}$, $R^{403}$, $R^{404}$, $R^{41}$, $R^{42}$, $R^{43}$, $n_0$, $n_1$, $n_2$, n3 and $X^-$, the same as those described above in connection with the compound of the fifth aspect of the present invention can be exemplified.

When the component (B) contains the component (B1), solubility in a typical resist solvent such as propylene glycol monomethyl ether (PGME), propylene glycol monomethyl ether acetate (PGMEA) or ethyl lactate (EL) becomes satisfactory, and line width roughness (LWR) can be reduced. Further, when the component (B) contains the component (B1), the perpendicularity and rectangularity of the resist pattern are excellent, regardless of whether it is formed on an inorganic antireflection film (organic BARC) or an organic antireflection film (organic BARC), and a resist pattern having excellent lithography properties such as excellent mask error factor (MEF) can be formed.

On the other hand, when the component (B) contains the component (B1'), solubility in the aforementioned typical resist solvent becomes satisfactory, and the perpendicularity and rectangularity of the resist pattern are excellent, regardless of whether it is formed on an inorganic antireflection film (organic BARC) or an organic antireflection film (organic BARC), especially, formation of necking on the side walls can be suppressed. Further, when the component (B) contains the component (B1'), the post exposure stability of the latent image formed by the pattern-wise exposure of the resist layer is improved, and generation of defects on the surface of the formed resist pattern can be suppressed, and hence, a resist pattern having excellent lithography properties can be formed. Here, defects refers to general abnormalities of a resist pattern, which are detected when observed from right above the developed resist pattern, using a surface defect detection equipment (trade name: "CKLA") manufactured by KLA-TENCOR CORPORATION. Examples of these abnormalities include post-developing scum, foam, dust, bridges across different portions of the resist pattern, color irregularities, and foreign deposits.

Furthermore, when the component (B) contains the component (B1) or the component (B1'), it can be used in a resist composition for immersion exposure or a resist composition for forming an upper-layer resist film, and the resist composition exhibits excellent lithography properties when it is used in a method of forming a resist pattern including immersion exposure or a method of forming a resist pattern including information of a triple-layer resist laminate.

The component (B1) and the component (B1') can be added to a resist composition for immersion exposure or a resist composition for forming an upper-layer resist film in large amounts. The reason for this is presumed that the component (B1) and the component (B1') exhibit high transparency (suppression of photoabsorption) to the exposure wavelength range (especially the wavelength range of ArF excimer laser).

As the component (B), one type of acid generator may be used, or two or more types may be used in combination.

In the resist composition of the present invention, when the component (B) contains the component (B1), the amount of the component (B1) based on the entire component (B) is preferably 35% by weight or more. By making the amount of the component (B1) at least as large as the lower limit of the above-mentioned range, the shape of the resist pattern becomes satisfactory. On the other hand, when the component (B) contains the component (B1'), the amount of the component (B1') based on the entire component (B) is preferably 40% by weight or more, more preferably 70% by weight or more, and may be even 100% by weight. Especially, when the component (B1') is used in a resist composition for inunersion exposure or a resist composition for forming an upper-layer resist film, the lithography properties of the formed patterns are improved. Further, when the component (B1') is used in a resist composition for forming an upper-layer resist film, the resist composition is advantageous in that the matching of the resist with the lower-layer film becomes satisfactory in the formation of a triple-layer resist laminate, and hence, footing of the resist pattern and the like can be suppressed.

Further, in the resist composition of the present invention, when the component (B) contains the component (B1), the amount of the component (B1) is preferably 1 to 30 parts by weight, more preferably 3 to 20 parts by weight, and most preferably 5 to 18 parts by weight, relative to 100 parts by weight of the component (A). On the other hand, when the component (B) contains the component (B1'), the amount of the component (B1') is preferably 1 to 30 parts by weight, more preferably 5 to 20 parts by weight, and most preferably 7 to 18 parts by weight relative to 100 parts by weight of the component (A). By making the amount of the component (B1) or (B1') at least as large as the lower limit of the above-mentioned range, the lithography properties of the formed resist pattern can be improved, especially when it is used in a a resist composition for immersion exposure or a resist composition for forming an upper-layer resist film. On the other hand, by making the amount of the component (B1) or (B1') no more than the upper limit of the above-mentioned range, the storage stability becomes satisfactory.

In the component (B), an acid generator (B2) other than the aforementioned component (B1) and component (B1') (hereafter, referred to as "component (B2)") may be used in combination with the component (B1) or the component (B1').

As the component (B2), there is no particular limitation as long as it is an acid generator other than the component (B1) and (B1'), and any of the known acid generators used in conventional chemically amplified resist compositions can be used.

Examples of these acid generators are numerous, and include onium salt-based acid generators such as iodonium salts and sulfonium salts; oxime sulfonate-based acid generators; diazomethane-based acid generators such as bisalkyl or bisaryl sulfonyl diazomethanes and poly(bis-sulfonyl)diazomethanes; nitrobenzylsulfonate-based acid generators; iminosulfonate-based acid generators; and disulfone-based acid generators.

As an onium salt-based acid generator, a compound represented by general formula (b-0) shown below can be preferably used.

[Chemical Formula 52]

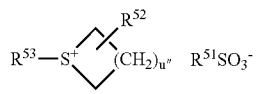

(b-0)

wherein $R^{51}$ represents a linear, branched or cyclic alkyl group, or a linear, branched or cyclic fluorinated alkyl group; $R^{52}$ represents a hydrogen atom, a hydroxyl group, a halogen atom, a linear or branched alkyl group, a linear or branched halogenated alkyl group, or a linear or branched alkoxy group; $R^{53}$ represents an aryl group which may have a substituent; and u" represents an integer of 1 to 3.

In general formula (b-0), $R^{51}$ represents a linear, branched or cyclic alkyl group, or a linear, branched or cyclic fluorinated alkyl group.

The linear or branched alkyl group preferably has 1 to 10 carbon atoms, more preferably 1 to 8 carbon atoms, and most preferably 1 to 4 carbon atoms.

The cyclic alkyl group preferably has 4 to 12 carbon atoms, more preferably 5 to 10 carbon atoms, and most preferably 6 to 10 carbon atoms.

The fluorinated alkyl group preferably has 1 to 10 carbon atoms, more preferably 1 to 8 carbon atoms, and most preferably 1 to 4 carbon atoms. The fluorination ratio of the fluorinated alkyl group (percentage of the number of fluorine atoms within the fluorinated alkyl group, based on the total number of fluorine atoms and hydrogen atoms within the alkyl group) is preferably from 10 to 100%, more preferably from 50 to 100%, and it is particularly desirable that all of the hydrogen atoms are substituted with fluorine atoms, as the acid strength increases.

$R^{51}$ is most preferably a linear alkyl group or a fluorinated alkyl group.

$R^{52}$ represents a hydrogen atom, a hydroxyl group, a halogen atom, a linear or branched alkyl group, a linear or branched halogenated alkyl group, or a linear or branched alkoxy group.

Examples of the halogen atom for $R^{52}$ include a fluorine atom, a bromine atom, a chlorine atom and an iodine atom, and a fluorine atom is preferable.

The alkyl group for $R^{52}$ is linear or branched, and preferably has 1 to 5 carbon atoms, more preferably 1 to 4 carbon atoms, and most preferably 1 to 3 carbon atoms.

The halogenated alkyl group for $R^{52}$ is a group in which some or all of the hydrogen atoms of the alkyl group have been substituted with halogen atoms. As the alkyl group of the halogenated alkyl group, the same as the alkyl group for $R^{52}$ may be exemplified. As the halogen atoms for substituting the hydrogen atoms of the alkyl group, the same as the halogen atom for $R^{52}$ may be exemplified. In the halogenated alkyl group, it is preferable that 50 to 100% of the hydrogen atoms of the alkyl group be substituted with halogen atoms, and it is more preferable that all of the hydrogen atoms are substituted with halogen atoms.

The alkoxy group for $R^{52}$ is linear or branched, and preferably has 1 to 5 carbon atoms, more preferably 1 to 4 carbon atoms, and most preferably 1 to 3 carbon atoms.

Among these, as $R^{52}$, a hydrogen atom is particularly desirable.

$R^{53}$ represents an aryl group which may have a substituent, and examples of the basic ring excluding the substituent include a naphthyl group, a phenyl group and an anthryl group. In terms of the effects of the present invention and absorption of exposure ray such as ArF excimer laser, a phenyl group is preferable.

Examples of the substituent include a hydroxyl group and a lower alkyl group (linear or branched, and preferably has no more than 5 carbon atoms, and a methyl group is particularly desirable).

As the aryl group for $R^{53}$, those which do not have a substituent are preferable.

u" is an integer of 1 to 3, preferably 2 or 3, and it is particularly desirable that u" be 3.

As preferable examples of acid generators represented by general formula (b-0), the following can be exemplified.

[Chemical Formula 53]

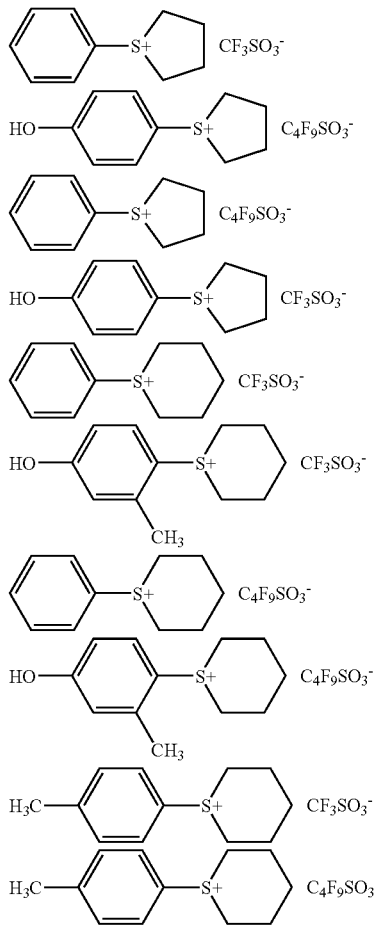

As the acid generator represented by general formula (b-0), one type may be used alone, or two or more types may be used in combination.

As an onium salt-based acid generator other than those represented by general formula (b-0), a compound represented by general formula (b-1) or (b-2) shown below can be preferably used.

[Chemical Formula 54]

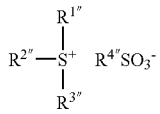

(b-1)

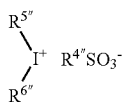

(b-2)

wherein $R^{1\prime\prime}$ to $R^{3\prime\prime}$, $R^{5\prime\prime}$ and $R^{6\prime\prime}$ each independently represents an aryl group or alkyl group, wherein two of $R^{1\prime\prime}$ to $R^{3\prime\prime}$ in formula (b-1) may be bonded to each other to form a ring with the sulfur atom; and $R^{4\prime\prime}$ represents a linear, branched or cyclic alkyl group or fluorinated alkyl group, with the proviso that at least one of $R^{1\prime\prime}$ to $R^{3\prime\prime}$ represents an aryl group, and at least one of $R^{5\prime\prime}$ and $R^{6\prime\prime}$ represents an aryl group.

In formula (b-1), $R^{1\prime\prime}$ to $R^{3\prime\prime}$ each independently represents an aryl group or an alkyl group. In formula (b-1), two of $R^{1\prime\prime}$ to $R^{3\prime\prime}$ in formula (b-1) may be bonded to each other to form a ring with the sulfur atom.

Further, among $R^{1\prime\prime}$ to $R^{3\prime\prime}$, at least one group represents an aryl group. Among $R^{1\prime\prime}$ to $R^{3\prime\prime}$, two or more groups are preferably aryl groups, and it is particularly desirable that all of $R^{1\prime\prime}$ to $R^{3\prime\prime}$ are aryl groups.

The aryl group for $R^{1\prime\prime}$ to $R^{3\prime\prime}$ is not particularly limited. For example, an aryl group having 6 to 20 carbon atoms may be used in which some or all of the hydrogen atoms of the aryl group may or may not be substituted with alkyl groups, alkoxy groups, halogen atoms or hydroxyl groups.

The aryl group is preferably an aryl group having 6 to 10 carbon atoms because it can be synthesized at a low cost. Specific examples thereof include a phenyl group and naphthyl group.

The alkyl group, with which hydrogen atoms of the aryl group may be substituted, is preferably an alkyl group having 1 to 5 carbon atoms, and most preferably a methyl group, an ethyl group, a propyl group, an n-butyl group, or a tert-butyl group.

The alkoxy group, with which hydrogen atoms of the aryl group may be substituted, is preferably an alkoxy group having 1 to 5 carbon atoms, and most preferably a methoxy group, ethoxy group, n-propoxy group, iso-propoxy group, n-butoxy group or tert-butoxy group.

The halogen atom, with which hydrogen atoms of the aryl group may be substituted, is preferably a fluorine atom.

The alkyl group for $R^{1\prime\prime}$ to $R^{3\prime\prime}$ is not particularly limited and includes, for example, a linear, branched or cyclic alkyl group having 1 to 10 carbon atoms. In terms of achieving excellent resolution, the alkyl group preferably has 1 to 5 carbon atoms. Specific examples thereof include a methyl group, an ethyl group, an n-propyl group, an isopropyl group, an n-butyl group, an isobutyl group, an n-pentyl group, a cyclopentyl group, a hexyl group, a cyclohexyl group, a nonyl group, and a decanyl group, and a methyl group is most preferable because it is excellent in resolution and can be synthesized at a low cost.

It is particularly desirable that each of $R^{1\prime\prime}$ to $R^{3\prime\prime}$ is a phenyl group or a naphthyl group.

When two of $R^{1\prime\prime}$ to $R^{3\prime\prime}$ in formula (b-1) are bonded to each other to form a ring with the sulfur atom, it is preferable that the two of $R^{1\prime\prime}$ to $R^{3\prime\prime}$ form a 3 to 10-membered ring including the sulfur atom, and it is particularly desirable that the two of $R^{1\prime\prime}$ to $R^{3\prime\prime}$ form a 5 to 7-membered ring including the sulfur atom. When two of $R^{1\prime\prime}$ to $R^{3\prime\prime}$ in formula (b-1) are bonded to each other to form a ring with the sulfur atom, the remaining one of $R^{1\prime\prime}$ to $R^{3\prime\prime}$ is preferably an aryl group. As examples of the aryl group, the same as the above-mentioned aryl groups for $R^{1\prime\prime}$ to $R^{3\prime\prime}$ can be exemplified.

$R^{4\prime\prime}$ represents a linear, branched or cyclic alkyl or fluorinated alkyl group.

The linear or branched alkyl group preferably has 1 to 10 carbon atoms, more preferably 1 to 8 carbon atoms, and most preferably 1 to 4 carbon atoms.

The cyclic alkyl group is preferably a cyclic group, as described for $R^{1\prime\prime}$, having 4 to 15 carbon atoms, more preferably 4 to 10 carbon atoms, and most preferably 6 to 10 carbon atoms.

The fluorinated alkyl group preferably has 1 to 10 carbon atoms, more preferably 1 to 8 carbon atoms, and most preferably 1 to 4 carbon atoms. Further, the fluorination ratio of the fluorinated alkyl group (percentage of fluorine atoms within the alkyl group) is preferably from 10 to 100%, more preferably from 50 to 100%, and it is particularly desirable that all hydrogen atoms are substituted with fluorine atoms because the acid strength increases.

$R^{4\prime\prime}$ is most preferably a linear or cyclic alkyl group or fluorinated alkyl group.

In formula (b-2), $R^{5\prime\prime}$ and $R^{6\prime\prime}$ each independently represents an aryl group or alkyl group. At least one of $R^{5\prime\prime}$ and $R^{6\prime\prime}$ represents an aryl group. It is preferable that both of $R^{5\prime\prime}$ and $R^{6\prime\prime}$ represent an aryl group.

As the aryl group for $R^{5\prime\prime}$ and $R^{6\prime\prime}$, the same as the aryl groups for $R^{1\prime\prime}$ to $R^{3\prime\prime}$ can be exemplified.

As the alkyl group for $R^{5\prime\prime}$ and $R^{6\prime\prime}$, the same as the alkyl groups for $R^{1\prime\prime}$ to $R^{3\prime\prime}$ can be exemplified.

It is particularly desirable that both of $R^{5\prime\prime}$ and $R^{6\prime\prime}$ represents a phenyl group.

As $R^{4\prime\prime}$ in formula (b-2), the same as those mentioned above for $R^{4\prime\prime}$ in formula (b-1) can be exemplified.

Specific examples of suitable onium salt-based acid generators represented by formula (b-1) or (b-2) include diphenyliodonium trifluoromethanesulfonate or nonafluorobutanesulfonate; bis(4-tert-butylphenyl)iodonium trifluoromethanesulfonate or nonafluorobutanesulfonate; triphenylsulfonium trifluoromethanesulfonate, heptafluoropropanesulfonate or nonafluorobutanesulfonate; tri(4-methylphenyl)sulfonium trifluoromethanesulfonate, heptafluoropropanesulfonate or nonafluorobutanesulfonate; dimethyl(4-hydroxynaphthyl)sulfonium trifluoromethanesulfonate, heptafluoropropanesulfonate or nonafluorobutanesulfonate; monophenyldimethylsulfonium trifluoromethanesulfonate, heptafluoropropanesulfonate or nonafluorobutanesulfonate; diphenylmonomethylsulfonium trifluoromethanesulfonate, heptafluoropropanesulfonate or nonafluorobutanesulfonate; (4-methylphenyl)diphenylsulfonium trifluoromethanesulfonate, heptafluoropropanesulfonate or nonafluorobutanesulfonate; (4-methoxyphenyl)diphenylsulfonium trifluoromethanesulfonate, heptafluoropropanesulfonate or nonafluorobutanesulfonate; tri(4-tert-butyl)phenylsulfonium trifluoromethanesulfonate, heptafluoropropanesulfonate or nonafluorobutanesulfonate; diphenyl(1-(4-methoxy)naphthyl)sulfonium trifluoromethanesulfonate, heptafluoropropanesulfonate or nonafluorobutanesulfonate; di(1-naphthyl)

phenylsulfonium trifluoromethanesulfonate, heptafluoropropanesulfonate or nonafluorobutanesulfonate; 1-phenyltetrahydrothiophenium trifluoromethanesulfonate, heptafluoropropanesulfonate or nonafluorobutanesulfonate; 1-(4-methylphenyl)tetrahydrothiophenium trifluoromethanesulfonate, heptafluoropropanesulfonate or nonafluorobutanesulfonate; 1-(3,5-dimethyl-4-hydroxyphenyl)tetrahydrothiophenium trifluoromethanesulfonate, heptafluoropropanesulfonate or nonafluorobutanesulfonate; 1-(4-methoxynaphthalene-1-yl)tetrahydrothiophenium trifluoromethanesulfonate, heptafluoropropanesulifonate or nonafluorobutanesulfonate; 1-(4-ethoxynaphthalene-1-yl)tetrahydrothiophenium trifluoromethanesulfonate, heptafluoropropanesulfonate or nonafluorobutanesulfonate; 1-(4-n-butoxynaphthalene-1-yl)tetrahydrothiophenium trifluoromethanesulfonate, heptafluoropropanesulfonate or nonafluorobutanesulfonate; 1-phenyltetrahydrothiopyranium trifuoromethanesulfonate, heptafluoropropanesulfonate or nonafluorobutanesulfonate; 1-(4-hydroxyphenyl)tetrahydrothiopyranium trifluoromethanesulfonate, heptafluoropropanesulfonate or nonafluorobutanesulfonate; 1-(3,5-dimethyl-4-hydroxyphenyl)tetrahydrothiopyranium trifluoromethanesulfonate, heptafluoropropanesulfonate or nonafluorobutanesulfonate; and 1-(4-methylphenyl)tetrahydrothiopyranium trifluoromethanesulfonate, heptafluoropropanesulfonate or nonafluorobutanesulfonate. It is also possible to use onium salts in which the anion moiety of these onium salts are replaced by methanesulfonate, n-propanesulfonate, n-butanesulfonate, or n-octanesulfonate.

Further, onium salt-based acid generators in which the anion moiety in general formula (b-1) or (b-2) is replaced by an anion moiety represented by general formula (b-3) or (b-4) shown above (the cation moiety is the same as (b-1) or (b-2)) may be used.

Furthermore, as an onium salt-based acid generator, a sulfonium salt having a cation moiety represented by general formula (b-5) or (b-6) shown below may be used.

[Chemical Formula 55]

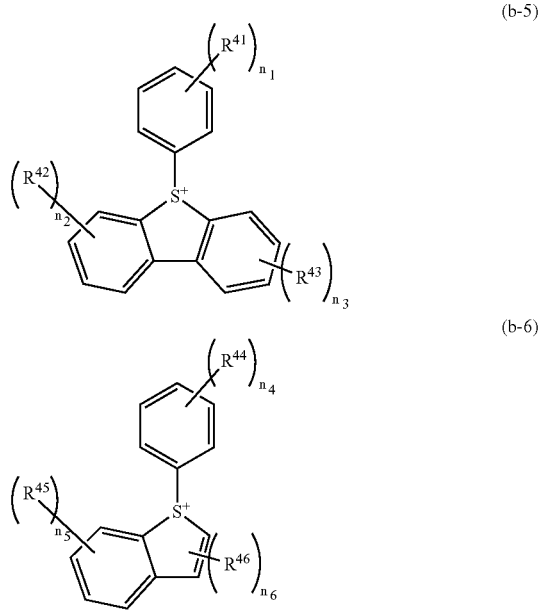

wherein $R^{41}$ to $R^{46}$ each independently represents an alkyl group, an acetyl group, an alkoxy group, a carboxy group, a hydroxyl group or a hydroxyalkyl group; $n_1$ to $n_5$ each independently represents an integer of 0 to 3; and $n_6$ represents an integer of 0 to 2.

With respect to $R^{41}$ to $R^{46}$, the alkyl group is preferably an alkyl group of 1 to 5 carbon atoms, more preferably a linear or branched alkyl group, and most preferably a methyl group, ethyl group, propyl group, isopropyl group, n-butyl group or tert butyl group.

The alkoxy group is preferably an alkoxy group of 1 to 5 carbon atoms, more preferably a linear or branched alkoxy group, and most preferably a methoxy group or ethoxy group.

The hydroxyalkyl group is preferably the aforementioned alkyl group in which one or more hydrogen atoms have been substituted with hydroxy groups, and examples thereof include a hydroxymethyl group, hydroxyethyl group and hydroxypropyl group.

When the subscripts $n_1$ to $n_6$ of $R^{41}$ to $R^{46}$ represent an integer of 2 or more, the plurality of $R^{41}$ to $R^{46}$ may be the same or different.

$n_1$ is preferably 0 to 2, more preferably 0 or 1, and still more preferably 0.

It is preferable that $n_2$ and $n_3$ each independently represent 0 or 1, and more preferably 0.

$n_4$ is preferably 0 to 2, and more preferably 0 or 1.

$n_5$ is preferably 0 or 1, and more preferably 0.

$n_6$ is preferably 0 or 1, and more preferably 1.

The anion moiety of the sulfonium salt having a cation moiety represented by general formula (b-5) or (b-6) is not particularly limited, and the same anion moieties for onium salt-based acid generators which have been proposed may be used. Examples of such anion moieties include fluorinated alkylsulfonic acid ions such as anion moieties ($R^{4"}SO_3^-$) for onium salt-based acid generators represented by general formula (b-1) or (b-2) shown above; and anion moieties represented by general formula (b-3) or (b-4) shown above. Among these, fluorinated alkylsulfonic acid ions are preferable, more preferably fluorinated alkylsulfonic acid ions of 1 to 4 carbon atoms, and linear perfluoroalkylsulfonic acid ions of 1 to 4 carbon atoms are particularly desirable. Specific examples include a trifluoromethylsulfonic acid ion, heptafluoro-n-propylsulfonic ion and nonafluoro-n-butylsulfonic acid ion.

In the present description, an oximesulfonate-based acid generator is a compound having at least one group represented by general formula (B-1) shown below, and has a feature of generating acid by irradiation. Such oximesulfonate-based acid generators are widely used for a chemically amplified resist composition, and can be appropriately selected.

[Chemical Formula 56]

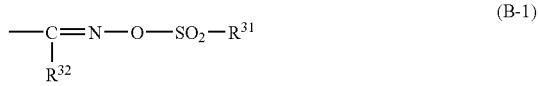

(B-1)

wherein $R^{31}$ and $R^{32}$ each independently represents an organic group.

The organic group for $R^{31}$ and $R^{32}$ refers to a group containing a carbon atom, and may include atoms other than carbon atoms (e.g., a hydrogen atom, an oxygen atom, a nitrogen atom, a sulfur atom, a halogen atom (such as a fluorine atom and a chlorine atom) and the like).

As the organic group for $R^{31}$, a linear, branched, or cyclic alkyl group or aryl group is preferable. The alkyl group or the aryl group may have a substituent. The substituent is not particularly limited, and examples thereof include a fluorine atom and a linear, branched, or cyclic alkyl group having 1 to 6 carbon atoms. The expression "having a substituent" means that some or all of the hydrogen atoms of the alkyl group or the aryl group are substituted with substituents.

The alkyl group preferably has 1 to 20 carbon atoms, more preferably 1 to 10 carbon atoms, still more preferably 1 to 8 carbon atoms, still more preferably 1 to 6 carbon atoms, and most preferably 1 to 4 carbon atoms. As the alkyl group, a partially or completely halogenated alkyl group (hereinafter, sometimes referred to as a "halogenated alkyl group") is particularly desirable. The "partially halogenated alkyl group" refers to an alkyl group in which some of the hydrogen atoms are substituted with halogen atoms, and the "completely halogenated alkyl group" refers to an alkyl group in which all of the hydrogen atoms are substituted with halogen atoms. Examples of the halogen atom include a fluorine atom, a chlorine atom, a bromine atom and an iodine atom, and a fluorine atom is particularly desirable. In other words, the halogenated alkyl group is preferably a fluorinated alkyl group.

The aryl group preferably has 4 to 20 carbon atoms, more preferably 4 to 10 carbon atoms, and most preferably 6 to 10 carbon atoms. As the aryl group, partially or completely halogenated aryl group is particularly desirable. The "partially halogenated aryl group" refers to an aryl group in which some of the hydrogen atoms are substituted with halogen atoms, and the "completely halogenated aryl group" refers to an aryl group in which all of hydrogen atoms are substituted with halogen atoms.

As $R^{31}$, an alkyl group of 1 to 4 carbon atoms which has no substituent or a fluorinated alkyl group of 1 to 4 carbon atoms is particularly desirable.

As the organic group for $R^{32}$, a linear, branched, or cyclic alkyl group, aryl group, or cyano group is preferable. Examples of the alkyl group and the aryl group for $R^{32}$ are the same as those of the alkyl group and the aryl group for $R^{31}$.

As $R^{32}$, a cyano group, an alkyl group of 1 to 8 carbon atoms having no substituent or a fluorinated alkyl group of 1 to 8 carbon atoms is particularly desirable.

Preferred examples of the oxime sulfonate-based acid generator include compounds represented by general formula (B-2) or (B-3) shown below.

[Chemical Formula 57]

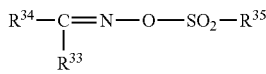

(B-2)

wherein $R^{33}$ represents a cyano group, an alkyl group having no substituent or a halogenated alkyl group; $R^{34}$ represents an aryl group; and $R^{35}$ represents an alkyl group having no substituent or a halogenated alkyl group.

[Chemical Formula 58]

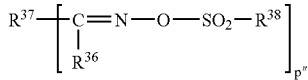

(B-3)

wherein $R^{36}$ represents a cyano group, an alkyl group having no substituent or a halogenated alkyl group; $R^{37}$ represents a divalent or trivalent aromatic hydrocarbon group; $R^{38}$ represents an alkyl group having no substituent or a halogenated alkyl group; and p" represents 2 or 3.

In general formula (B-2), the alkyl group having no substituent or the halogenated alkyl group for $R^{33}$ preferably has 1 to 10 carbon atoms, more preferably 1 to 8 carbon atoms, and most preferably 1 to 6 carbon atoms.

As $R^{33}$, a halogenated alkyl group is preferable, and a fluorinated alkyl group is more preferable.

The fluorinated alkyl group for $R^{33}$ preferably has 50% or more of the hydrogen atoms thereof fluorinated, more preferably 70% or more, and most preferably 90% or more.

Examples of the aryl group for $R^{34}$ include groups in which one hydrogen atom has been removed from an aromatic hydrocarbon ring, such as a phenyl group, a biphenyl group, a fluorenyl group, a naphthyl group, an anthryl group, and a phenantryl group, and heteroaryl groups in which some of the carbon atoms constituting the ring(s) of these groups are substituted with hetero atoms such as an oxygen atom, a sulfur atom, and a nitrogen atom. Of these, a fluorenyl group is preferable.

The aryl group for $R^{34}$ may have a substituent such as an alkyl group of 1 to 10 carbon atoms, a halogenated alkyl group, or an alkoxy group. The alkyl group and halogenated alkyl group as the substituent preferably has 1 to 8 carbon atoms, and more preferably 1 to 4 carbon atoms. The halogenated alkyl group is preferably a fluorinated alkyl group.

The alkyl group having no substituent or the halogenated alkyl group for $R^{35}$ preferably has 1 to 10 carbon atoms, more preferably 1 to 8 carbon atoms, and most preferably 1 to 6 carbon atoms.

As $R^{35}$, a halogenated alkyl group is preferable, and a fluorinated alkyl group is more preferable.

In terms of enhancing the strength of the acid generated, the fluorinated alkyl group for $R^{35}$ preferably has 50% or more of the hydrogen atoms fluorinated, more preferably 70% or more, still more preferably 90% or more. A completely fluorinated alkyl group in which 100% of the hydrogen atoms are substituted with fluorine atoms is particularly desirable.

In general formula (B-3), the alkyl group having no substituent and the halogenated alkyl group for $R^{36}$ are the same as the alkyl group having no substituent and the halogenated alkyl group for $R^{33}$.

Examples of the divalent or trivalent aromatic hydrocarbon group for $R^{37}$ include groups in which one or two hydrogen atoms have been removed from the aryl group for $R^{34}$.

As the alkyl group having no substituent or the halogenated alkyl group for $R^{38}$, the same one as the alkyl group having no substituent or the halogenated alkyl group for $R^{35}$ can be used.

p" is preferably 2.

Specific examples of suitable oxime sulfonate-based acid generators include α-(p-toluenesulfonyloxyimino)-benzyl cyanide, α-(p-chlorobenzenesulfonyloxyimino)-benzyl cyanide, α-(4-nitrobenzenesulfonyloxyimino)-benzyl cyanide, α-(4-nitro-2-trifluoromethylbenzenesulfonyloxyimino)-benzyl cyanide, α-(benzenesulfonyloxyimino)-4-chlorobenzyl cyanide, α-(benzenesulfonyloxyimino)-2,4-dichlorobenzyl cyanide, α-(benzenesulfonyloxyimino)-2,6-dichlorobenzyl cyanide, α-(benzenesulfonyloxyimino)-4-methoxybenzyl cyanide, α-(2-chlorobenzenesulfonyloxyimino)-4-methoxybenzyl cyanide, α-(benzenesulfonyloxyimino)-thien-2-yl acetonitrile, α-(4-dodecylbenzenesulfonyloxyimino)benzyl cyanide, α-[(p-toluenesulfonyloxyimino)-4-methoxyphenyl]acetonitrile, α-[(dodecylbenzenesulfonyloxyimino)-4- methoxyphenyl]acetonitrile, α-(tosyloxyimino)-4-thienyl cyanide, α-(methylsulfonyloxyimino)-1-cyclopentenyl acetonitrile, α-(methylsulfonyloxyimino)-1-cyclohexenyl acetonitrile, α-(methylsulfonyloxyimino)-1-cycloheptenyl acetonitrile, α-(methylsulfonyloxyimino)-1-cyclooctenyl acetonitrile, α-(trifluoromethylsulfonyloxyimino)-1-cyclopentenyl acetonitrile, α-(trifluoromethylsulfonyloxyimino)-cyclohexyl acetonitrile, α-(ethylsulfonyloxyimino)-ethyl acetonitrile, α-(propylsulfonyloxyimino)-propyl acetonitrile, α-(cyclohexylsulfonyloxyitnino)-cyclopentyl acetonitrile, α-(cyclohexylsulfonyloxyimino)-cyclohexyl acetonitrile, α-(cyclohexylsulfonyloxyimino)-1-cyclopentenyl acetonitrile, α-(ethylsulfonyloxyimino)-1-cyclopentenyl acetonitrile, α-(isopropylsulfonyloxyimino)-1-cyclopentenyl acetonitrile, α-(n-butylsulfonyloxyimino)-1-cyclopentenyl acetonitrile, α-(ethylsulfonyloxyimino)-1-cyclohexenyl acetonitrile, α-(isopropylsulfonyloxyimino)-1-cyclohexenyl acetonitrile, α-(n-butylsulfonyloxyimino)-1-cyclohexenyl acetonitrile, α-(methylsulfonyloxyimino)-phenyl acetonitrile, α-(methylsulfonyloxyimino)-p-methoxyphenyl acetonitrile, α-(trifluoromethylsulfonyloxyimino)-phenyl acetonitrile, α-(trifluoromethylsulfonyloxyimino)-p-methoxyphenyl acetonitrile, α-(ethylsulfonyloxyimino)-p-methoxyphenyl acetonitrile, α-(propylsulfonyloxyimino)-p-methylphenyl acetonitrile, and α-(methylsulfonyloxyimino)-p-bromophenyl acetonitrile.

Further, oxime sulfonate-based acid generators disclosed in Japanese Unexamined Patent Application, First Publication No. Hei 9-208554 (Chemical Formulas 18 and 19 shown in paragraphs [0012] to [0014]) and oxime sulfonate-based acid generators disclosed in WO 2004/074242A2 (Examples 1 to 40 described at pages 65 to 85) may be preferably used.

Furthermore, as preferable examples, the following can be exemplified.

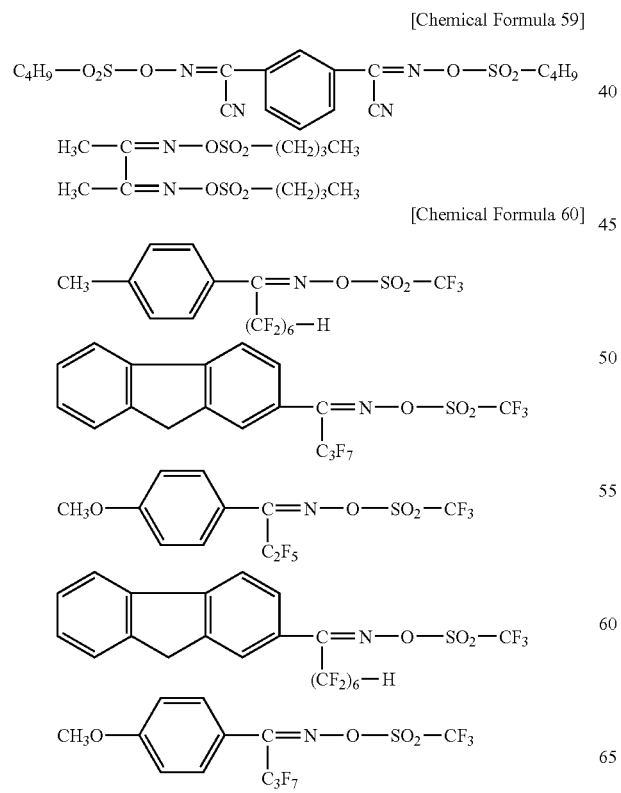

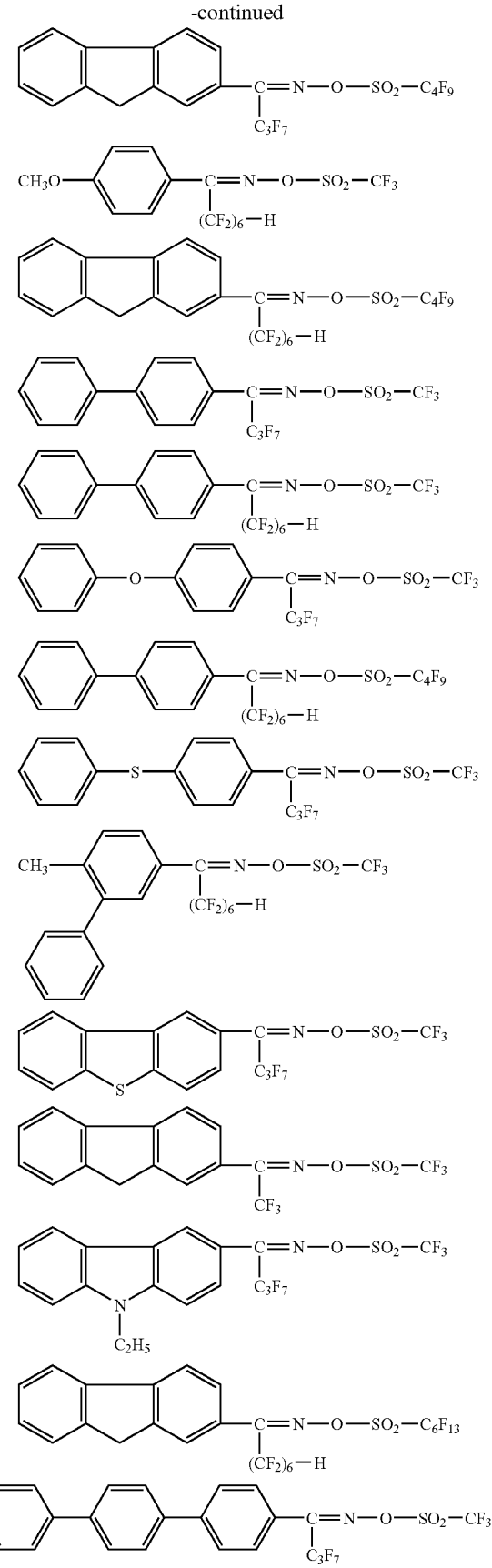

-continued

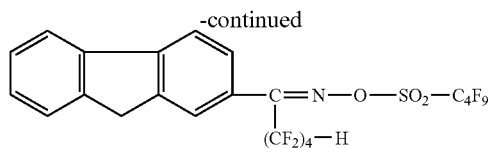

Among the above-exemplified compounds, the following 4 compounds are preferable.

[Chemical Formula 61]

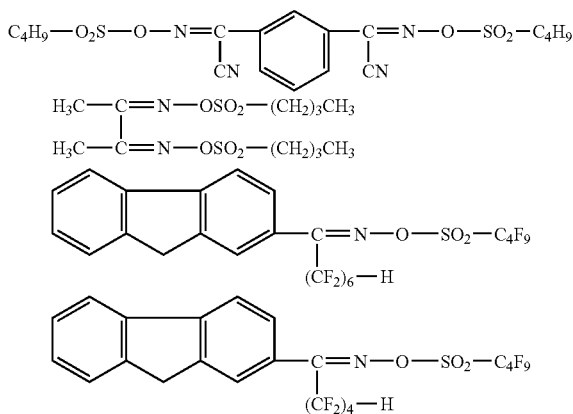

Of the aforementioned diazomethane-based acid generators, specific examples of suitable bisalkyl or bisaryl sulfonyl diazomethanes include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and bis(2,4-dimethylphenylsulfonyl)diazomethane.

Further, diazomethane-based acid generators disclosed in Japanese Unexamined Patent Application, First Publication No. Hei 11-035551, Japanese Unexamined Patent Application, First Publication No. Hei 11-035552 and Japanese Unexamined Patent Application, First Publication No. Hei 11-035573 may be preferably used.

Furthermore, as poly(bis-sulfonyl)diazomethanes, those disclosed in Japanese Unexamined Patent Application, First Publication No. Hei 11-322707, including 1,3-bis(phenylsulfonyldiazomethylsulfonyl)propane, 1,4-bis(phenylsulfonyldiazomethylsulfonyl)butane, 1,6-bis(phenylsulfonyldiazomethylsulfonyl)hexane, 1,10-bisphenylsulfonyldiazomethylsulfonyl)decane, 1,2-bis(cyclohexylsulfonyldiazomethylsulfonyl)ethane, 1,3-bis(cyclohexylsulfonyldiazomethylsulfonyl)propane, 1,6-bis(cyclohexylsulfonyldiazomethylsulfonyl)hexane, and 1,10-bis(cyclohexylsulfonyldiazomethylsulfonyl)decane, may be exemplified.

As the component (B2), one type of acid generator may be used, or two or more types may be used in combination.

The total amount of the component (B) within the resist composition of the present invention is 0.5 to 30 parts by weight, and preferably 1 to 20 parts by weight, relative to 100 parts by weight of the component (A). When the amount of the component (B) is within the above-mentioned range, formation of a resist pattern can be satisfactorily performed. Further, by virtue of the above-mentioned range, a uniform solution can be obtained and the storage stability becomes satisfactory.

<Component (D)>

In the resist composition of the present invention, for improving the resist pattern shape and the post exposure stability of the latent image formed by the pattern-wise exposure of the resist layer, it is preferable to add a nitrogen-containing organic compound (D) (hereafter referred to as the component (D)) as an optional component.

A multitude of these components (D) have already been proposed, and any of these known compounds may be used, although an aliphatic amine, and particularly a secondary aliphatic amine or tertiary aliphatic amine is preferable. In the present description and claims, the term "aliphatic" is a relative concept used in relation to the term "aromatic", and defines a group or compound that has no aromaticity.

The term "aliphatic cyclic group" refers to a monocyclic group or polycyclic group that has no aromaticity. An aliphatic amine is an amine having one or more aliphatic groups, and the aliphatic groups preferably have 1 to 12 carbon atoms.

Examples of these aliphatic amines include amines in which at least one hydrogen atom of ammonia ($NH_3$) has been substituted with an alkyl group or hydroxyalkyl group of no more than 12 carbon atoms (i.e., alkylamines or alkylalcoholamines), and cyclic amines.

Specific examples of alkylamines and alikylalcoholamines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine, and tri-n-dodecylamine; and alkyl alcohol amines such as diethanolamine, triethanolamine, diisopropanolamine, triisopropanolamine, di-n-octanolamine, and tri-n-octanolamine. Among these, trialkylamines of 5 to 10 carbon atoms are preferable, tri-n-pentylamine and tri-n-octylamine are more preferable, and tri-n-pentylamine is particularly desirable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine, and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

These compounds can be used either alone, or in combinations of two or more different compounds.

The component (D) is typically used in an amount within a range from 0.01 to 5.0 parts by weight, relative to 100 parts by weight of the component (A).

<Optional Component>[Component (E)]

Furthermore, in the resist composition of the present invention, for preventing any deterioration in sensitivity, and improving the resist pattern shape and the post exposure stability of the latent image formed by the pattern-wise exposure of the resist layer, at least one compound (E) (hereafter referred to as the component (E)) selected from the group consisting of an organic carboxylic acid, or a phosphorus oxo acid or derivative thereof can be added.

Examples of suitable organic carboxylic acids include acetic acid, malonic acid, citric acid, malic acid, succinic acid, benzoic acid, and salicylic acid.

Examples of phosphorus oxo acids or derivatives thereof include phosphoric acid, phosphonic acid and phosphinic acid. Among these, phosphonic acid is particularly desirable.

Examples of oxo acid derivatives include esters in which a hydrogen atom within the above-mentioned oxo acids is substituted with a hydrocarbon group. Examples of the hydrocarbon group include an alkyl group of 1 to 5 carbon atoms and an aryl group of 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenylphosphonic acid, diphenyl phosphonate and dibenzyl phosphonate.

Examples of phosphinic acid derivatives include phosphinic acid esters such as phenylphosphinic acid.

As the component (E), one type may be used alone, or two or more types may be used in combination.

As the component (E), an organic carboxylic acid is preferable, and salicylic acid is particularly desirable.

The component (E) is typically used in an amount within a range from 0.01 to 5.0 parts by weight, relative to 100 parts by weight of the component (A).

<Component (O)>

If desired, other miscible additives can also be added to the resist composition of the present invention. Examples of such miscible additives include additive resins for improving the performance of the resist film, surfactants for improving the applicability, dissolution inhibitors, plasticizers, stabilizers, colorants, halation prevention agents, and dyes.

<Component (S)>

The resist composition according to the first aspect of the present invention can be prepared by dissolving the materials for the resist composition in an organic solvent (hereafter, frequently referred to as "component (S)").

The component (S) may be any organic solvent which can dissolve the respective components to give a uniform solution, and any one or more kinds of organic solvents can be appropriately selected from those which have been conventionally known as solvents for a chemically amplified resist.

Examples thereof include lactones such as γ-butyrolactone; ketones such as acetone, methyl ethyl ketone, cyclohexanone, methyl-n-pentyl ketone, methyl isopentyl ketone, and 2-heptanone; polyhydric alcohols, such as ethylene glycol, diethylene glycol, propylene glycol and dipropylene glycol; compounds having an ester bond, such as ethylene glycol monoacetate, diethylene glycol monoacetate, propylene glycol monoacetate, and dipropylene glycol monoacetate; polyhydric alcohok derivatives including compounds having an ether bond, such as a monoalkylether (e.g., monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; and aromatic organic solvents such as anisole, ethylbenzylether, cresylmethylether, diphenylether, dibenzylether, phenetole, butylphenylether, ethylbenzene, diethylbenzene, pentylbenzene, isopropylbenzene, toluene, xylene, cymene and mesitylene.

These solvents can be used individually, or in combination as a mixed solvent.

Among these, propylene glycol monomethyl ether acetate (PGMEA), propylene glycol monomethyl ether (PGME), ethyl lactate (EL) and γ-butyrolactone are preferable.

Further, among the mixed solvents, a mixed solvent obtained by mixing PGMEA with a polar solvent is preferable. The mixing ratio (weight ratio) of the mixed solvent can be appropriately determined, taking into consideration the compatibility of the PGMEA with the polar solvent, but is preferably in the range of 1:9 to 9:1, more preferably from 2:8 to 8:2.

Specifically, when EL is mixed as the polar solvent, the PGMEA:EL weight ratio is preferably from 1:9 to 9:1, and more preferably from 2:8 to 8:2. Alternatively, when PGME is mixed as the polar solvent, the PGMEA:PGME is preferably from 1:9 to 9:1, more preferably from 2:8 to 8:2, and still more preferably 3:7 to 7:3.

Further, as the component (S), a mixed solvent of at least one of PGMEA and EL with γ-butyrolactone is also preferable. The mixing ratio (former:latter) of such a mixed solvent is preferably from 70:30 to 95:5.

Furthermore, as the component (S), a mixed solvent of a mixture of PGMEA and PGME with γ-butyrolactone is also preferable. The mixing ratio (former: latter) of such a mixed solvent is preferably from 99.9:0.1 to 80:20, more preferably from 99.9:0.1 to 90:10, and most preferably from 99:9:0.1 to 95:5.

By virtue of the above-mentioned range, the rectangularity of the resist pattern is improved.

The amount of the organic solvent is not particularly limited, and is appropriately adjusted to a concentration which enables coating of a coating solution to a substrate, depending on the thickness of the coating film. In general, the organic solvent is used in an amount such that the solid content of the resist composition becomes within the range from 2 to 20% by weight, and preferably from 4 to 15% by weight.

The resist composition of the present invention is a novel resist composition which was conventionally unknown. By the resist composition of the present invention, a resist pattern having excellent perpendicularity and rectangularity can be formed, regardless of whether the resist pattern is formed on an inorganic antireflection film (organic BARC) or an organic antireflection film (organic BARC). Especially, in the resist composition of the present invention, when the component (B) contains the component (B1), line width roughness (LWR) can be reduced, and a resist pattern having excellent lithography properties such as excellent mask error factor (MEF) can be formed. On the other hand, especially when the component (B) contains the component (B1'), formation of necking on the side walls of the resist pattern can be suppressed.

The reasons for these have not yet been elucidated, but are presumed as follows.

In the present invention, an acid generator (B1) containing the compound represented by general formula (b1-8) above or an acid generator (B1') containing the compound represented by general formula (b1-9) above is used. As compared to acid generators having triphenylsulfonium (TPS) or the like as the cation moiety, the component (B1) and the component (B1') are advantageous in that photoabsorption is effectively suppressed in the exposure wavelength range (especially the wavelength range of ArF excimer laser) and they exhibit high transparency, and hence, they can be used in large amounts in the resist composition. Further, the component (B1) and the component (B1') exhibit excellent solubility in an organic solvent (resist solvent) for dissolving the respective components of the resist composition. As a result, it is presumed that the concentration of the acid generator within the resist film is increased, and efficiency of acid generation is enhanced.

Furthermore, in the compound represented by general formula (b1-9) above, for example, by using a highly hydrophobic group such as a cyclic alkyl group for $R^{404}$, so as to enhance the hydrophobicity of the alkoxyalkyl group including $R^{402}$, $R^{403}$ and $R^{404}$, the dispersity of the compound within the resist film becomes excellent. As a result, it is presumed that the compound can be more uniformly dispersed within the resist film than conventional acid generators.

Therefore, it is presumed that the acid generated from the component (B1') upon exposure is more uniformly dispersed within the resist film than conventional acid generators.

For the reasons described above, in the resist composition of the present invention, by using a base component in combination with an acid generator (the component (B1) or the component (B1')), it is presumed that a resist pattern having excellent perpendicularity and rectangularity can be formed, regardless of whether the resist pattern is formed on an inorganic antireflection film (organic BARC) or an organic antireflection film (organic BARC). Especially, when the component (B) contains the component (B1), line width roughness (LWR) can be reduced, and a resist pattern having excellent lithography properties such as excellent mask error factor (MEF) can be formed. On the other hand, especially when the component (B) contains the component (B1'), formation of necking on the side walls of the resist pattern can be suppressed. Further, since the component (B1') exhibits excellent solubility in a resist solvent, the post exposure stability of the latent image formed by the pattern-wise exposure of the resist layer is improved, and generation of defects on the surface of the formed resist pattern can be suppressed, and hence, a resist pattern having excellent lithography properties can be formed.

In addition, it is presumed that the resist composition of the present invention can be preferably used as a resist composition for immersion exposure in a method of forming a resist pattern including immersion exposure, and excellent lithography properties can be achieved. Further, it is presumed that the resist composition of the present invention can be preferably used as a resist composition for forming an upper-layer resist film in a method of forming a resist pattern including formation of a triple-layer resist laminate, and excellent lithography properties can be achieved.

The MEF is a parameter that indicates how faithfully mask patterns of differing dimensions can be reproduced by using the same exposure dose with fixed pitch and changing the mask size (line width and space width). The closer the MEF value is to 1, the better the mask reproducibility.

The compound represented by general formula (b1-8) above has a structure in which a phenolic hydroxyl group is protected by an oxycarbonyl group including the acid dissociable, dissolution inhibiting group $R^{401}$, and the structure does not change at unexposed portions. Similarly, the compound represented by general formula (b1-9) above has a structure in which a phenolic hydroxyl group is protected by an alkoxyalkyl group including $R^{402}$, $R^{403}$ and $R^{404}$, i.e., an acetal-type acid dissociable, dissolution inhibiting group, and the structure does not change at unexposed portions. Therefore, it is presumed that the compound represented by general formula (b1-8) above and the compound represented by general formula (b1-9) above exhibit the effect of suppressing the component (A1) from dissolving in an alkali developing solution at unexposed portions of the resist film.

On the other hand, at exposed portions, the alkoxyalkyl group within the compound represented by general formula (b1-9) above is dissociated from the oxygen atom constituting the phenolic hydroxyl group by the generated acid during post exposure bake (PEB). As a result, it is presumed that a compound having a phenolic hydroxyl group is generated, and the compound exhibit the effect of promoting dissolution of the component (A1) in an alkali developing solution.

For the reasons described above, it is presumed that, when the resist composition of the present invention is a positive resist composition, the compound represented by general formula (b1-8) above or the compound represented by general formula (b1-9) above exhibits the effects of promoting dissolution at exposed portions and suppressing dissolution at unexposed portions. As a result, it is presumed that a high contrast between exposed portions and unexposed portions can be achieved, and a resist pattern having an excellent perpendicularity can be formed. Especially, when the compound represented by general formula (b1-9) is used, it is presumed that a resist pattern having excellent rectangularity can be formed, and formation of necking on the side walls of the resist pattern can be suppressed.

<<Method of Forming a Resist Pattern>>

Next, the method of forming a resist pattern according to the second aspect of the present invention will be described.

The method of forming a resist pattern according to the present invention includes: applying a resist composition of the first aspect of the present invention to a substrate to form a resist film on the substrate; conducting exposure of the resist film; and alkali-developing the resist film to form a resist pattern.

More specifically, the method for forming a resist pattern according to the present invention can be performed, for example, as follows. Firstly, a resist composition according to the first aspect of the present invention is applied onto a substrate using a spinner or the like, and a prebake (post applied bake (PAB)) is conducted under temperature conditions of 80 to 150° C. for 40 to 120 seconds, preferably 60 to 90 seconds to form a resist film. Then, for example, using an ArF exposure apparatus or the like, the resist film is selectively exposed to an ArF excimer laser beam through a desired mask pattern, followed by post exposure bake (PEB) under temperature conditions of 80 to 150° C. for 40 to 120 seconds, preferably 60 to 90 seconds. Subsequently, developing is conducted using an alkali developing solution such as a 0.1 to 10% by weight aqueous solution of tetramethylamrnmoniun hydroxide, preferably followed by rinsing with pure water, and drying. If desired, bake treatment (post bake) can be conducted following the developing. In this manner, a resist pattern that is faithful to the mask pattern can be obtained.

The substrate is not specifically limited and a conventionally known substrate can be used. For example, substrates for electronic components, and such substrates having wiring patterns formed thereon can be exemplified. Specific examples of the material of the substrate include metals such as silicon wafer, copper, chromium, iron and aluminum; and glass. Suitable materials for the wiring pattern include copper, aluminum, nickel, and gold.

Further, as the substrate, any one of the above-exemplified substrates provided with an inorganic and/or organic film on the surface thereof may be used. As the inorganic film, an inorganic antireflection film (inorganic BARC) can be exemplified. As the organic film, an organic antireflection film (organic BARC) can be exemplified.

The wavelength to be used for exposure is not particularly limited and the exposure can be conducted using radiations such as ArF excimer laser, KrF excimer laser, $F_2$ excimer laser, extreme ultraviolet rays (EUV), vacuum ultraviolet rays (VUV), electron beam (EB), X-rays, and soft X-rays. The resist composition of the present invention is effective to KrF excimer laser, ArF excimer laser, EB and EUV, and particularly effective to ArF excimer laser. Further, the resist composition of the present invention is also effective to immersion exposure.

EXAMPLES

As follows is a description of examples of the present invention, although the scope of the present invention is by no way limited by these examples.

Synthesis Example 1

Synthesis of Intermediate Compound (b1-51)

[Chemical Formula 62]

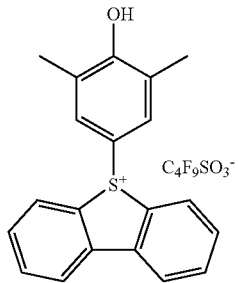

(b1-61)

1.99 g of diphosphorus pentaoxide was added to 120.2 g of methanesulfonic acid, and 5.86 g of 2,6-dimethylphenol was added thereto. The resulting solution was cooled down to 20° C. or lower in a water bath, and 8.01 g of dibenzothiophenoxide was gradually added thereto. Then, the water bath was removed, and a reaction was effected at room temperature for 14 hours. Thereafter, a mixed solution of 180.3 g of water and 180.3 g of dichloromethane was cooled down to 10° C. or lower, and the reaction liquid was dropwise added thereto gradually while maintaining the temperature of the reaction liquid at 25° C. or lower. Then, the aqueous phase was extracted from the reaction liquid by separation, and 13.54 g of sodium nonafluorobutane sulfonate was added thereto and stirred at room temperature for 1.5 hours. Then, 314.3 g of dichloromethane was added thereto and stirred, and the organic phase was extracted by separation. The organic phase was washed with 118.2 g of pure water until the organic phase became neutral, and the organic phase was extracted by separation. To the organic phase was added hexane (360.6 g) as a poor solvent to obtain crystals. The obtained crystals were dried at 40° C. under reduced pressure, thereby obtaining 12.0 g of an intermediate compound (yield: 40%).

The intermediate compound was analyzed by $^1$H-NMR and $^{19}$F-NMR.

$^1$H-NMR (DMSO-d6, 600 MHz): δ (ppm)=9.59 (br s, 1H, He), 8.49 (d, 2H, H$^a$), 8.25 (d, 2H, H$^d$), 7.95 (t, 2H, H$^c$), 7.74 (t, 2H, H$^b$), 7.20 (s, 2H, H$^e$), 2.14 (s, 6H, H$^f$).

$^{19}$F-NMR (Acetone-d6, 376 MHz): δ ppm)=−81.2, −114.6, −121.5, −126.0.

From the results shown above, it was confirmed that the intermediate compound had the structure shown below.

[Chemical Formula 63]

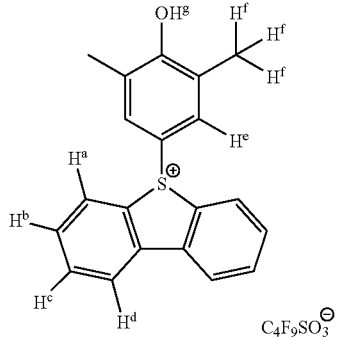

Example 1

Synthesis of Compound (b1-81)

[Chemical Formula 64]

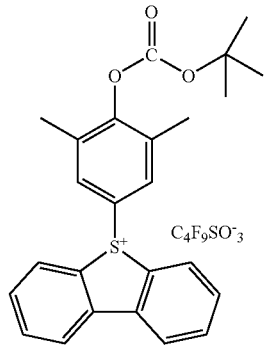

(b1-81)

45.4 g of dichloromethane, 9.1 g of the intermediate compound (b1-5 1) and 0.4 g of N,N-dimethylaminopyridine were mixed together, 4.0 g of di-tert-butyl-dicarbonate was added to the resulting slurry, and a reaction was effected at 40° C. for 1 hour. Thereafter, the resultant was washed with diluted hydrochloric acid, followed by washing with water. Then, a dichloromethane solution of the resultant was dropwise added to 275 g of hexane, thereby obtaining 9.5 g of the objective compound in the form of a white powder (yield: 95%).

The obtained compound was analyzed by $^1$H-NMR and $^{19}$F-NMR.

$^1$H-NMR (DMSO-d6, 400 MHz): δ(ppm)=8.53 (d, 2H, H$^a$), 8.36 (d, 2H, H$^d$), 7.97 (t, 2H, H$^c$), 7.77 (t, 2H, H$^b$), 7.44 (s, 2H, H$^e$), 2.11 (s, 6H, CH$_3$), 1.47(s, 9H, tBu).

$^{19}$F-NMR (DMSO-d6, 376 MHz): δ(ppm)=−80.4, −114.8, −121.4, −125.7.

Further, as a result of a thermal analysis (TG-DTA), it was found that the peak decomposition temperature (Td) was 146° C., and the mass loss at that portion was 14.5%. This mass loss corresponds to the loss due to the elimination of the tert-butoxycarbonyl group.

From the results shown above, it was confirmed that the compound had a structure shown below.

[Chemical Formula 65]

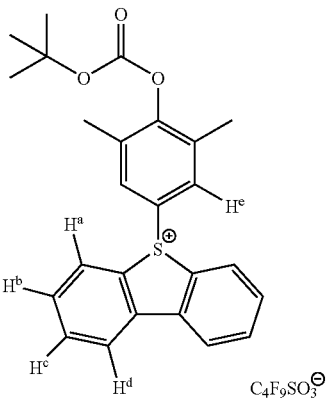

<Evaluation of Solubility>

With respect to the aforementioned compound of the third aspect of the present invention ((B)-1: (b1-81)), phenyldibenzothiophenium nonafluorobutane sulfonate ((B)-2: chemical formula (b1-01) shown below), di(1-naphthyl)phenylsulfonium nonafluorobutane sulfonate ((B)-3: chemical formula (b'-01) shown below) and the aforementioned intermediate compound ((B)-4: (b1-51)), the solubility was evaluated as follows.

[Chemical Formula 66]

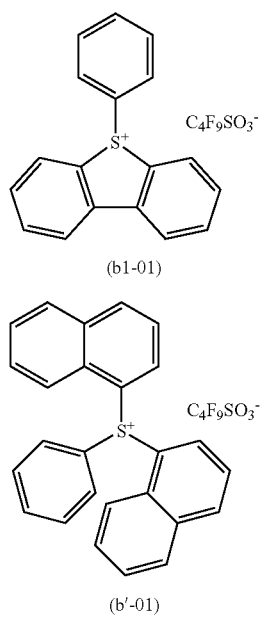

(b1-01)

[Chemical Formula 67]

(b'-01)

With respect to each of the compounds, propylene glycol monomethyl ether acetate (PGMEA) solutions, propylene glycol monomethyl ether (PGME) solutions and ethyl lactate (EL) solutions of various concentrations were prepared. The prepared solutions were stirred to evaluate the concentration at which the acid generator was completely dissolved.

The results are shown in Table 1. It was confirmed that the solubility of the compound (b1-81) according to the third aspect of the present invention in PGMEA, PGME and EL (which are typical resist solvents) was about the same level as phenyldibenzothiophenium nonafluorobutane sulfonate (b1-01) which is known to exhibit excellent solubility, and superior to di(1-naphthyl)phenylsulfonium nonafluorobutane sulfonate and the aforementioned intermediate compound (b1-51) which are widely used as acid generators.

TABLE 1

|  | Example 1 (B)-1 (b1-81) | Reference Example (B)-2 (b1-01) | Reference Example (B)-3 (b'-01) | Reference Example (B)-4 (b1-51) |
|---|---|---|---|---|
| Solubility in PGME (% by weight) | 10 | 10-15 | <2 | <2 |
| Solubility in PGMEA (% by weight) | 20 | 20 | 5 | 10-15 |
| Solubility in EL (% by weight) | 20 | 20 | 5 | 10-15 |

Example 2,

Comparative Example 1

Base Component (A)

The copolymer (A)-1 used as the component (A) in Example 2 and Comparative Example 1 is shown below.

The weight average molecular weight (Mw) and dispersity (Mw/Mn) of the copolymer (A)-1 are also shown below. The weight average molecular weight (Mw) and dispersity (Mw/Mn) were determined by the polystyrene equivalent value as measured by gel permeation chromatography (GPC).

Further, the compositional ratio was determined by carbon NMR. In the chemical formula, the subscript numerals of the respective structural units indicate the percentage (mol %) of the respective structural units within the copolymer

[Chemical Formula 68]

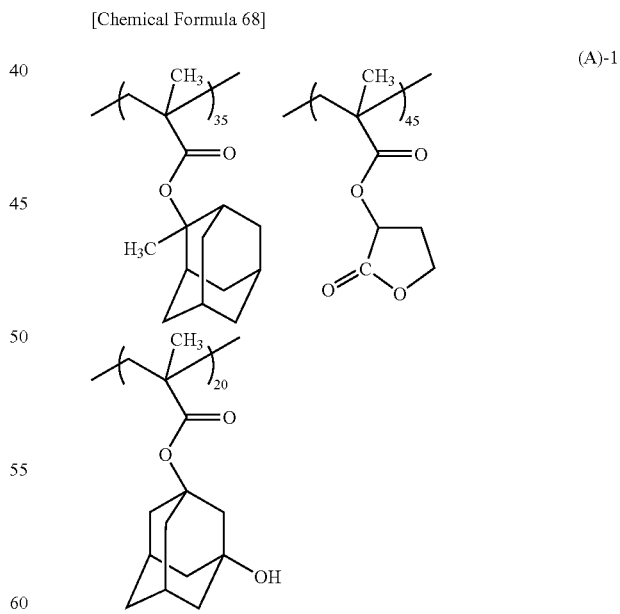

(Mw: 7,000, Mw/Mn: 2.0; the copolymer was synthesized by a conventional dropwise polymerization method using monomers which derive the respective structural units. In chemical formula (A)-1, the subscript numerals on the brackets indicate the percentage (mol %) of the respective structural units within the copolymer. The compositional ratio was determined by $^{13}$C-NMR. Further, Mw and Mw/Mn were determined by the polystyrene equivalent value as measured by gel permeation chromatography (GPC).)

<Preparation of Positive Resist Composition Solution>

The components shown in Table 2 were mixed together and dissolved to obtain positive resist composition solutions.

TABLE 2

|  | (A) | (B) | (D) | (E) | (S) | |
|---|---|---|---|---|---|---|
| Example 2 | (A)-1 [100] | (B)-1 [13.82] | (D)-1 [0.54] | (E)-1 [1.32] | (S)-1 [2200] | (S)-2 [10] |
| Comparative Example 1 | (A)-1 [100] | (B)-2 [11.0] | (D)-1 [0.54] | (E)-1 [1.32] | (S)-1 [2200] | (S)-2 [10] |

In Table 2, the reference characters indicate the following. Further, the values in brackets [ ] indicate the amount (in terms of parts by weight) of the component added. The amount of (B)-1 in Example 2 is the molar equivalent to the amount of (B)-1 in Comparative Example 1.

(B)-1: an acid generator represented by chemical formula (b1-81) shown below (compound of Example 1)

(B)-2: an acid generator represented by chemical formula (b1-01) shown below

[Chemical Formula 69]

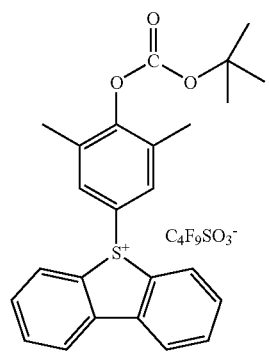

(b1-81)

[Chemical Formula 70]

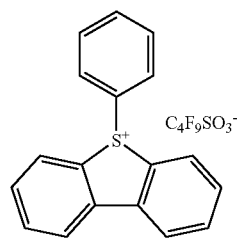

(b1-01)

(D)-1: tri-n-pentylamine
(E)-1: salicylic acid
(S)-1: a mixed solvent of PGMEA/PGME=6/4 (weight ratio)
(S)-2: γ-butyrolactone <Evaluation of Lithography Properties>

Using the obtained positive resist composition solutions, resist patterns were formed, and the following lithography properties were evaluated.

[Formation of Resist Pattern]

An organic anti-reflection film composition (product name: ARC-29A, manufactured by Brewer Science Ltd.) was applied onto an 8-inch silicon wafer using a spinner, and the composition was then baked at 205° C. for 60 seconds, thereby forming an organic anti-reflection film having a film thickness of 82 nm. Then, the positive resist composition solution obtained above was applied onto the anti-reflection film using a spinner, and was then prebaked (PAB) on a hotplate at the temperature indicated in Table 3 for 60 seconds and dried, thereby forming a resist film having a film thickness of 120 nm.

Subsequently, the resist film was selectively irradiated with an ArF excimer laser (193 nm) through a mask pattern, using an ArF exposure apparatus NSR-S302 (manufactured by Nikon Corporation, NA (numerical aperture)=0.60, 2/3 annular illumination). Thereafter, a post exposure bake (PEB) treatment was conducted at the temperature indicated in Table 3 for 60 seconds, followed by development for 30 seconds at 23° C. in a 2.38% by weight aqueous solution of tetramethylammonium hydroxide. Then, the resist was washed for 30 seconds with pure water, followed by drying by shaking, thereby forming a line and space (1:1) resist pattern (L/S pattern). In this manner, the optimum exposure dose (sensitivity: Eop, mJ/cm$^2$) for forming a L/S pattern having a line width of 120 nm and a pitch of 240 nm was determined.

[Line Width Roughness]

With respect to the L/S pattern having a line width of 120 nm and a pitch of 240 nm formed with the above-mentioned Eop, 5 points in the lengthwise direction of the line were measured using a measuring SEM (product name: S-9220, manufactured by Hitachi, Ltd.), and from the results, the value of 3 times the standard deviation s (i.e., 3 s) was calculated as a yardstick of LWR. The results are shown in Table 3.

The smaller this 3 s value is, the lower the level of roughness of the line width, indicating that a resist pattern with a uniform width was obtained.

[Evaluation of Mask Error Factor (MEF)]

With the above-mentioned Eop, L/S patterns were formed using a mask pattern targeting a L/S pattern having a line width of 130 nm and a pitch of 260 nm and a mask pattern targeting a L/S pattern having a line width of 120 nm and a pitch of 260 nm. With respect to the formed L/S patterns, the MEF was determined by the following formula.

$$MEF=|CD_{130}-CD_{120}|/|MD_{130}-MD_{120}|$$

In this formula, $CD_{130}$ and $CD_{120}$ represent the respective line widths (nm) of the actual L/S patterns respectively formed using the mask pattern targeting a line width of 130 nm and the mask pattern targeting a line width of 120 nm, and $MD_{130}$ and $MD_{120}$ represent the respective target line widths (nm), meaning $MD_{130}$=130 and $MD_{120}$=120. The closer the MEF value is to 1, the better the mask reproducibility of the resist pattern formed.

The results are shown in Table 3.

TABLE 3

|  | Example 2 | Comparative Example 1 |
|---|---|---|
| PAB temperature (° C.) | 110 | 110 |
| PEB temperature (° C.) | 110 | 110 |
| Eop (mJ/cm$^2$) | 97.5 | 56.0 |
| LWR | 8.7 | 10.4 |
| MEF | 1.85 | 2.02 |

The resist pattern formed in Example 2 using a resist composition according to the present invention had excellent perpendicularity, as compared to the resist pattern formed in Comparative Example 1, and footing at the substrate interface was suppressed. Further, from the results shown in Table 3, it was confirmed that the resist pattern formed in Example 2 using a resist composition according to the present invention had excellent LWR and MEF, as compared to the resist pattern formed in Comparative Example 1.

From the results shown above, it was confirmed that the resist composition of Example 2 according to the present invention could achieve excellent lithography properties.

Examples 3 to 5

Base Component (A)

The copolymer (A)-2 used as the component (A) in Examples 3 to 5 is shown below.

The weight average molecular weight (Mw) and dispersity (Mw/Mn) of the copolymer (A)-2 are also shown below. The weight average molecular weight (Mw) and dispersity (Mw/Mn) were determined by the polystyrene equivalent value as measured by gel permeation chromatography (GPC).

Further, the compositional ratio was determined by carbon NMR. In the chemical formula, the subscript numerals of the respective structural units indicate the percentage (mol %) of the respective structural units within the copolymer.

[Chemical Formula 71]

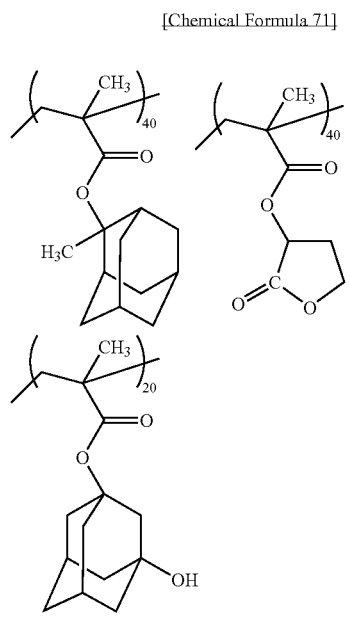

(A)-2

(Mw: 5,000, Mw/Mn: 1.6; the copolymer was synthesized by a conventional dropwise polymerization method using monomers which derive the respective structural units.)

<Preparation of Positive Resist Composition Solution>

The components shown in Table 4 were mixed together and dissolved to obtain positive resist composition solutions.

TABLE 4

| | (A) | (B) | | | (D) | (E) | (S) | |
|---|---|---|---|---|---|---|---|---|
| Example 3 | (A)-2 [100] | (B)-1 [11.0] | (B)-3 [2.0] | | (D)-1 [0.54] | (E)-1 [1.32] | (S)-1 [2200] | (S)-2 [10] |
| Example 4 | (A)-2 [100] | (B)-1 [5.0] | (B)-4 [6.0] | (B)-5 [2.0] | (D)-1 [0.40] | (E)-1 [1.32] | (S)-1 [2200] | (S)-2 [10] |

TABLE 4-continued

| | (A) | (B) | | | (D) | (E) | (S) | |
|---|---|---|---|---|---|---|---|---|
| Example 5 | (A)-2 [100] | (B)-1 [5.0] | (B)-4 [6.0] | (B)-3 [2.0] | (D)-1 [0.50] | (E)-1 [1.32] | (S)-1 [2200] | (S)-2 [10] |

In Table 4, the reference characters indicate the following. Further, the values in brackets [ ] indicate the amount (in terms of parts by weight) of the component added. The amount of (B)-1 in Example 3 is the molar equivalent to the amount of (B)-2 in Comparative Example 1.

(B)-1: an acid generator represented by chemical formula (b1-81) shown above (compound of Example 1)

(B)-3: triphenylsulfonium heptafluoro-n-propane sulfonate (B)-4: an acid generator represented by chemical formula (b-5-5) shown below (B)-5: tri(4-tert-butyl)phenylsulfonium nonafluoro-n-butane sulfonate

[Chemical Formula 72]

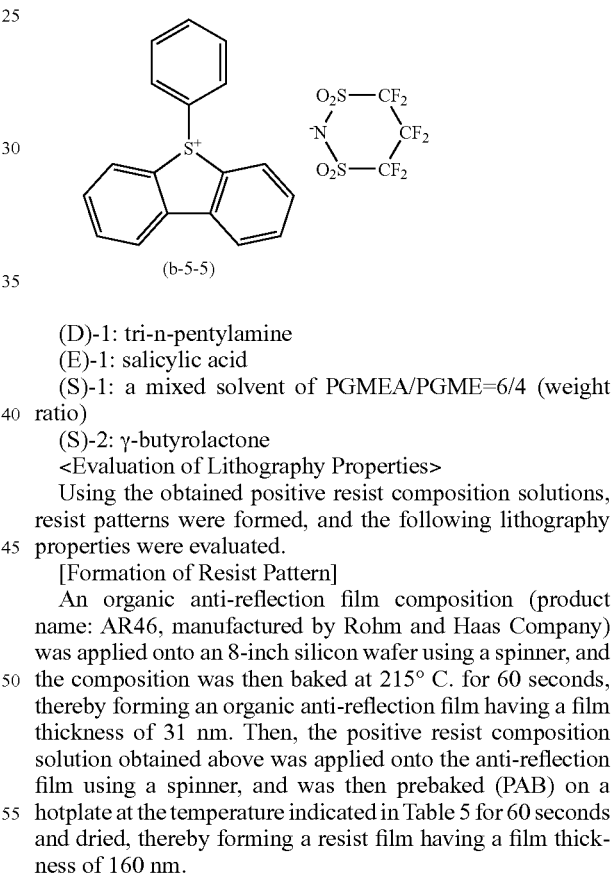

(b-5-5)

(D)-1: tri-n-pentylamine
(E)-1: salicylic acid
(S)-1: a mixed solvent of PGMEA/PGME=6/4 (weight ratio)
(S)-2: γ-butyrolactone <Evaluation of Lithography Properties>

Using the obtained positive resist composition solutions, resist patterns were formed, and the following lithography properties were evaluated.

[Formation of Resist Pattern]

An organic anti-reflection film composition (product name: AR46, manufactured by Rohm and Haas Company) was applied onto an 8-inch silicon wafer using a spinner, and the composition was then baked at 215° C. for 60 seconds, thereby forming an organic anti-reflection film having a film thickness of 31 nm. Then, the positive resist composition solution obtained above was applied onto the anti-reflection film using a spinner, and was then prebaked (PAB) on a hotplate at the temperature indicated in Table 5 for 60 seconds and dried, thereby forming a resist film having a film thickness of 160 nm.

Subsequently, the resist film was selectively irradiated with an ArF excimer laser (193 nm) through a mask pattern, using an ArF exposure apparatus NSR-S306 (manufactured by Nikon Corporation, NA (numerical aperture)=0.78, Dipole Y). Thereafter, a post exposure bake (PEB) treatment was conducted at the temperature indicated in Table 5 for 60 seconds, followed by development for 30 seconds at 23° C. in a 2.38% by weight aqueous solution of tetramethylanunonium hydroxide. Then, the resist was washed for 30 seconds with pure water, followed by drying by shaking, thereby forming a line and space (1:1) resist pattern (L/S pattern). In this manner, the optimum exposure dose (sensitivity: Eop, mJ/cm$^2$) for forming a L/S pattern having a line width of 90 nm and a pitch of 198 nm was determined.

[Line Width Roughness]

With respect to the L/S pattern having a line width of 90 nm and a pitch of 198 nm formed with the above-mentioned Eop, 5 points in the lengthwise direction of the line were measured using a measuring SEM ((product name: S-9220, manufactured by Hitachi, Ltd.)), and from the results, the value of 3 times the standard deviation s (i.e., 3 s) was calculated as a yardstick of LWR. The results are shown in Table 5.

The smaller this 3 s value is, the lower the level of roughness of the line width, indicating that a resist pattern with a uniform width was obtained.

[Evaluation of Mask Error Factor (MEF)]

With the above-mentioned Eop, L/S patterns were formed using a mask pattern targeting a L/S pattern having a line width of 90 nm and a pitch of 198 nm and a mask pattern targeting a L/S pattern having a line width of 80 nm and a pitch of 198 nm. With respect to the formed L/S patterns, the MEF was determined in the same manner as in Example 2.

The results are shown in Table 5.

TABLE 5

|  | Example 3 | Example 4 | Example 5 |
| --- | --- | --- | --- |
| PAB temperature (° C.) | 110 | 110 | 110 |
| PEB temperature (° C.) | 110 | 110 | 110 |
| Eop (mJ/cm$^2$) | 32.4 | 29.4 | 23.1 |
| LWR | 5.3 | 5.2 | 6.2 |
| MEF | 1.22 | 1.32 | 1.37 |

The resist patterns formed in Example 3 to 5 using resist compositions according to the present invention had excellent perpendicularity, and footing at the substrate interface was suppressed. Further, from the results shown in Table 5, it was confirmed that the resist patterns formed in Examples 3 to 5 using resist compositions according to the present invention had excellent LWR and MEF.

Example 6

Synthesis of Compound (b1-141)

[Chemical Formula 73]

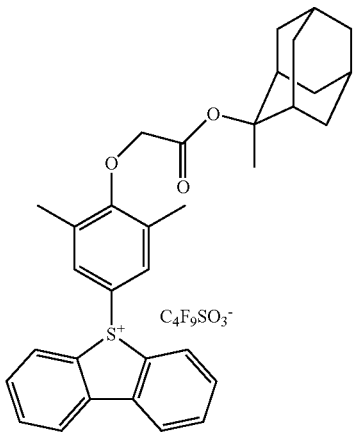

(b1-141)

6.05 g of the aforementioned intermediate compound (b1-51) was dissolved in 60.5 g of dehydrated tetrahydrofuran and cooled with ice. Then, 0.48 g of sodium hydride (purity: 60%) was gradually added thereto, followed by addition of 3.45 g of 2-methyl-2-adamantane bromoacetate. A reaction was effected under reflux for 21 hours. Thereafter, the reaction liquid was dropwise added to 81.8 g of pure water which had been cooled with ice in advance, and extraction was conducted 3 times with 108.8 g of dichloromethane. The organic phase was condensed to obtain a solid, and the obtained solid was dissolved in 40.55 g of dichloromethane. The organic phase was washed with diluted hydrochloric acid, followed by washing with water. Then, the resulting dichloromethane solution was dropwise added to 608.25 g of n-hexane, thereby obtaining 6.95 g of the objective compound (yield: 85.7%).

The obtained compound was analyzed by NMR.

$^1$H-NMR (DMSO-d6, 400 MHz): δ(ppm)=8.49 (d, 2H, ArH), 8.30 (d, 2H, ArH), 7.93 (t, 2H, ArH), 7.73 (t, 2H, ArH), 7.30 (s, 2H, ArH), 4.52 (s, CH2), 2.16-2.24 (br s, 8H, Ar—CH3+Adamantane), 1.45-1.92 (m, 15H, Adamantane+CH3).

$^{19}$F-NMR (DMSO-d6, 376 MHz): δ(ppm)=−77.7, −112.0, −118.6, −122.9.

From the results shown above, it was confirmed that the compound had a structure shown above.

Synthesis Example 2

Synthesis of Intermediate Compound (b1-52)

[Chemical Formula 74]

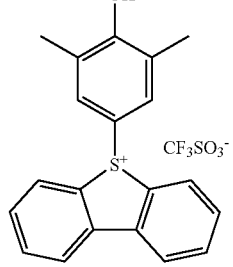

(b1-52)

1.99 g of diphosphorus pentaoxide was added to 120.2 g of methanesulfonic acid, and 5.86 g of 2,6-dimethylphenol was added thereto. The resulting solution was cooled down to 20° C. or lower in a water bath, and 8.01 g of dibenzothiophenoxide was gradually added thereto. Then, the water bath was removed, and a reaction was effected at room temperature for 14 hours. Thereafter, a mixed solution of 180.3 g of water and 180.3 g of dichloromethane was cooled down to 10° C. or lower, and the reaction liquid was dropwise added thereto gradually while maintaining the temperature of the reaction liquid at 25° C. or lower. Then, the aqueous phase was extracted from the reaction liquid by separation, and 7.53 g of potassium trifluoromethane sulfonate was added thereto and stirred at room temperature for 1 hour. A precipitated powder was filtered, and washed with pure water (90.9 g) 3 times. The powder was dried in vacuum, thereby obtaining 6.36 g of the objective compound (yield: 35.0%).

The obtained compound was analyzed by NMR.

$^1$H-NMR (DMSO-d6, 400 MHz): δ(ppm)=9.73 (br s, 1H, OH), 8.47 (d, 2H, ArH), 8.24 (d, 2H, ArH), 7.91 (t, 2H, ArH), 7.71 (t, 2H, ArH), 7.18 (s, 2H, ArH), 2.10 (s, CH3).

$^{19}$F-NMR (DMSO-d6, 376 MHz): δ(ppm)=−75.0.

From the results shown above, it was confirmed that the compound had a structure shown above.

Example 7

Synthesis of Compound (b1-142)

[Chemical Formula 75]

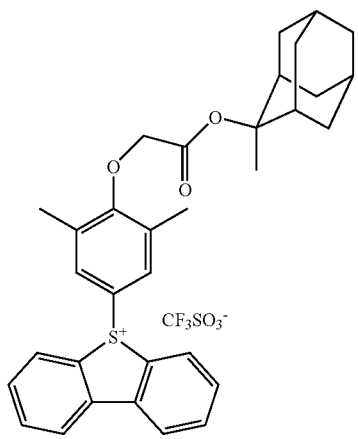
(b1-142)

4.54 g of the intermediate compound (b1-52) was dissolved in 68.1 g of dehydrated tetrahydrofuran and cooled with ice. Then, 0.48 g of sodium hydride (purity: 60%) was gradually added thereto, followed by addition of 3.45 g of 2-methyl-2-adamantane bromoacetate. A reaction was effected under reflux for 21 hours. Thereafter, the reaction liquid was dropwise added to 76.7 g of pure water which had been cooled with ice in advance, and extraction was conducted 3 times with 102.0 g of dichloromethane. The organic phase was condensed to obtain a solid, and the obtained solid was dissolved in 66.10 g of dichloromethane. The organic phase was washed with diluted hydrochloric acid, followed by washing with water. Then, the resulting dichloromethane solution was dropwise added to 661.0 g of n-hexane, thereby obtaining 4.32 g of the objective compound (yield: 65.4%).

The obtained compound was analyzed by NMR.

$^1$H-NMR (DMSO-d6, 400 MHz): δ(ppm)=8.49 (d, 2H, ArH), 8.30 (d, 2H, ArH), 7.93 (t, 2H, ArH), 7.73 (t, 2H, ArH), 7.30 (s, 2H, ArH), 4.52 (s, CH2), 2.16-2.24 (br s, 8H, Ar—CH3+Adamantane), 1.44-1.92 (m, 15H, Adamantane+CH3).

$^{19}$F-NMR (DMSO-d6, 376 MHz): δ(ppm)=−75.0.

From the results shown above, it was confirmed that the compound had a structure shown above.

Example 8

Preparation of Positive Resist Composition Solution

The components shown in Table 6 were mixed together and dissolved to obtain a positive resist composition solution.

TABLE 6

| | (A) | (B) | (D) | (E) | (S) | |
|---|---|---|---|---|---|---|
| Example 8 | (A)-1 [100] | (B)-6 [15.9] | (D)-1 [0.54] | (E)-1 [1.32] | (S)-1 [2200] | (S)-2 [10] |

In Table 6, the reference characters indicate the following. Further, the values in brackets [ ] indicate the amount (in terms of parts by weight) of the component added.

(B)-6: an acid generator represented by chemical formula (b1-141) shown above (compound of Example 6)

<Evaluation of Lithography Properties>

Using the obtained positive resist composition solution, a resist pattern was formed in the same manner as in Example 2 and Comparative Example 1, and the lithography properties were evaluated. The results are shown in Table 7.

TABLE 7

| | Example 8 |
|---|---|
| PAB temperature (° C.) | 110 |
| PEB temperature (° C.) | 110 |
| Eop (mJ/cm$^2$) | 110 |
| LWR | 9.2 |
| MEF | 1.93 |

The resist pattern formed in Example 8 using a resist composition according to the present invention, like the resist pattern formed in Example 2, had excellent perpendicularity, as compared to the resist pattern formed in Comparative Example 1, and footing at the substrate interface was suppressed. Further, from the results shown in Table 7, it was confirmed that the resist pattern formed in Example 8 using a resist composition according to the present invention, like the resist pattern formed in Example 2, had excellent LWR and MEF, as compared to the resist pattern formed in Comparative Example 1.

From the results shown above, it was confirmed that the resist composition of Example 8 according to the present invention could achieve excellent lithography properties.

Synthesis Example 3

Synthesis of Compound (3)

[Chemical Formula 76]

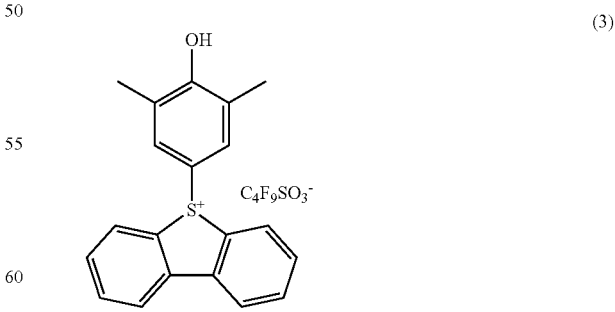
(3)

12.0 g of a compound (3) represented by chemical formula (3) shown above was obtained in the same manner as in Synthesis Example 1.

The obtained compound (3) was analyzed by NMR. As a result, it was confirmed that the obtained compound (3) had the same structure as the aforementioned intermediate compound (b1-51).

Synthesis Example 4

Synthesis of Compound (4)

[Chemical Formula 77]

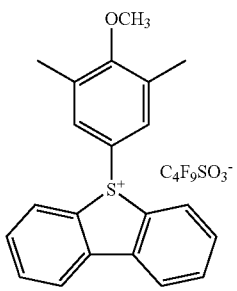

(4)

0.50 g of diphosphorus pentaoxide was added to 30 g of methanesulfonic acid, and 1.63 g of 2,6-dimethylanisole was added thereto. The resulting solution was cooled down to 20° C. or lower in a water bath, and 2.00 g of dibenzothiophenoxide was gradually added thereto. Then, the water bath was removed, and a reaction was effected at room temperature for 14 hours. Thereafter, a mixed solution of 45 g of water and 45 g of dichloromethane was cooled down to 10° C. or lower, and the reaction liquid was dropwise added thereto gradually while maintaining the temperature of the reaction liquid at 25° C. or lower. Then, the aqueous phase was extracted from the reaction liquid by separation, and 3.38 g of potassium nonafluorobutane sulfonate was added thereto and stirred at room temperature for 2.5 hours. Then, 31.0 g of dichloromethane was added thereto and stirred, and the organic phase was extracted by separation. The organic phase was washed with 11.7 g of pure water until the organic phase became neutral, and the organic phase was extracted by separation. The extracted organic phase was condensed and dried, thereby obtaining 0.89 g of a compound (4) represented by chemical formula (4) shown above.

The obtained compound (4) was analyzed by $^1$H-NMR and $^{19}$F-NMR.

$^1$H-NMR (CDCl$_3$, 400 MHz): δ(ppm)=8.26 (d, 2H, H$^a$), 8.08 (d, 2H, H$^d$), 7.86 (t, 2H, H$^c$), 7.63 (t, 2H, H$^b$), 7.27 (s, 2H, H$^e$), 3.73 (s, 3H, H$^g$), 2.22 (s, 6H, H$^f$).

$^{19}$F-NMR (CDCl$_3$, 376 MHz): δ(ppm)=80.8, 11.3, 121.3, 125.7.

From the results shown above, it was confirmed that the compound had a structure shown below.

[Chemical Formula 78]

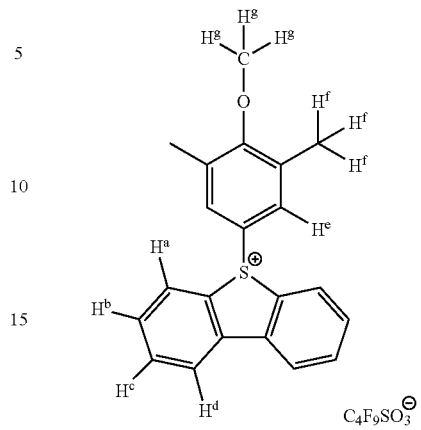

Synthesis Example 5

Synthesis of Compound (5)

[Chemical Formula 79]

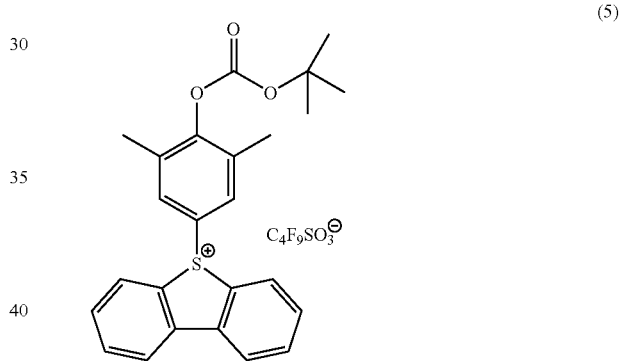

(5)

45.4 g of dichloromethane, 9.1 g of the aforementioned compound (3) and 0.4 g of N,N-dimethylaminopyridine were mixed together, 4.0 g of di-tert-butyl-dicarbonate was added to the resulting slurry, and a reaction was effected at 40° C. for 1 hour. Thereafter, the resultant was washed with diluted hydrochloric acid, followed by washing with water. Then, a dichloromethane solution of the resultant was dropwise added to 275 g of hexane, thereby obtaining 9.5 g of the compound (5) represented by chemical formula (5) above in the form of a white powder (yield: 95%).

The obtained compound was analyzed by $^1$H-NMR and $^{19}$F-NMR.

$^1$H-NMR (DMSO-d6, 400 MHz): δ(ppm)=8.53 (d, 2H, H$^a$), 8.36 (d, 2H, H$^d$), 7.97 (t, 2H, H$^c$), 7.77 (t, 2H, H$^b$), 7.44 (s, 2H, H$^e$), 2.11 (s, 6H, CH$_3$), 1.47 (s, 9H, tBu).

$^{19}$F-NMR(DMSO-d6, 376 MHz): δ(ppm)=−80.4, −114.8, −121.4, −125.7.

Further, as a result of a thermal analysis (TG-DTA), it was found that the peak decomposition temperature (Td) was 146° C., and the mass loss at that portion was 14.5%. This mass loss corresponds to the loss due to the elimination of the tert-butoxycarbonyl group.

From the results shown above, it was confirmed that the compound had a structure shown below.

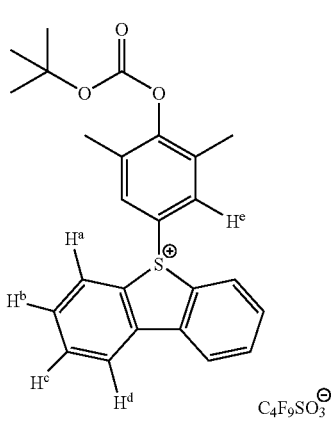

Example 9

Synthesis of Compound (b1-91)

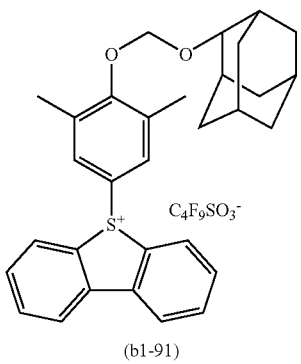

(b1-91)

The aforementioned compound (3) (6.1 g) was added to 42.4 g of a tetrahydrofuran solution, and cooled with ice. Then, sodium hydride (0.44 g) was added thereto, and a tetrahydrofuran (4.4 g) solution of 2-adamantane chloromethyl ether (2.2 g) was dropwise added thereto. Then, the resultant was elevated to room temperature and stirred for 1 hour. The reaction liquid was dropwise added to water, and extraction of the resulting solution was conducted with dichloromethane (90 g). Thereafter, the dichloromethane phase was washed with diluted hydrochloric acid, followed by washing with water. The resulting dichloromethane solution was dropwise added to hexane (150 g), thereby obtaining 6.1 g of the objective compound (b1-91) in the form of a white powder.

The obtained compound was analyzed by $^1$H-NMR and $^{19}$F-NMR.

$^1$H-NMR (DMSO-d6, 400 MHz): δ(ppm)=8.52 (d, 2H, H$^a$), 8.33 (d, 2H, H$^d$), 7.96 (t, 2H, H$^c$), 7.76 (t, 2H, H$^b$), 7.32 (s, 2H, H$^e$), 5.13 (s, 2H, CH$_2$), 2.21 (s, 6H, CH$_3$), 1.38-1.98 (m, 15H, Adamantane).

$^{19}$F-NMR (DMSO-d6, 376 MHz): δ(ppm)=−80.4, −114.8, −121.4, −125.7.

From the results shown above, it was confirmed that the obtained compound had a structure shown below.

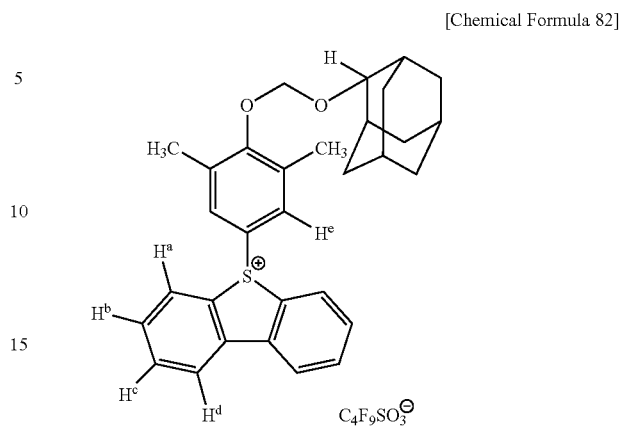

Example 10

Synthesis of Compound (b 1-100)

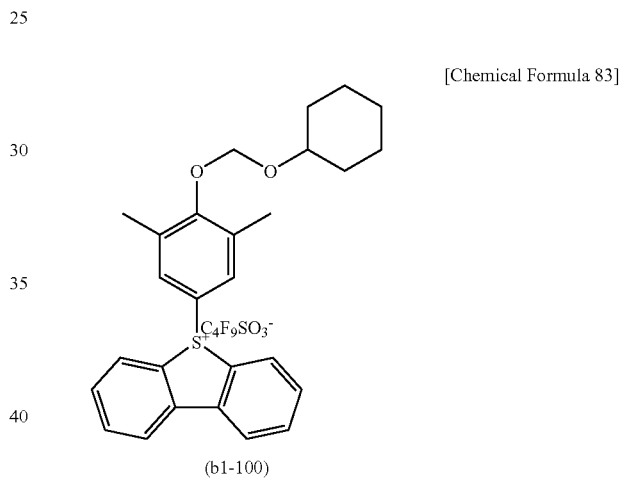

(b1-100)

In a nitrogen atmosphere, 6.1 g of the aforementioned compound (3) was added to 72.6 g of a tetrahydrofuran solution, and cooled with ice. Then, 0.44 g of sodium hydride was added thereto, and a tetrahydrofuran (4.4 g) solution of 1.7 g of chloromethyl cyclohexyl ether was dropwise added thereto. Then, the resultant was elevated to room temperature and stirred for 1 hour. The reaction liquid was dropwise added to water, and extraction of the resulting solution was conducted with 90 g of dichloromethane. Thereafter, the dichloromethane phase was washed with diluted hydrochloric acid, followed by washing with water. The resulting dichloromethane solution was dropwise added to 150 g of hexane, thereby obtaining 5.7 g of the objective compound in the form of a white powder.

The obtained compound was analyzed by $^1$H-NMR.

$^1$H-NMR (DMSO-d6, 400 MHz): δ(ppm)=8.51 (d, 2H, H$^a$), 8.32 (d, 2H, H$^d$), 7.97 (t, 2H, H$^c$), 7.76 (t, 2H, H$^b$), 7.32 (s, 2H, H$^e$), 5.10 (s, 2H, H$^f$), 3.21 (s, 1H, H$^g$), 2.22 (s, 6H, H$^h$), 1.12-1.87 (m, 10H, Cyclohexyl).

$^{19}$F-NMR (DMSO-d6, 376 MHz): δ(ppm)=−0.4, −114.5, −121.1, −125.3.

From the results shown above, it was confirmed that the obtained compound had a structure shown below.

[Chemical Formula 84]

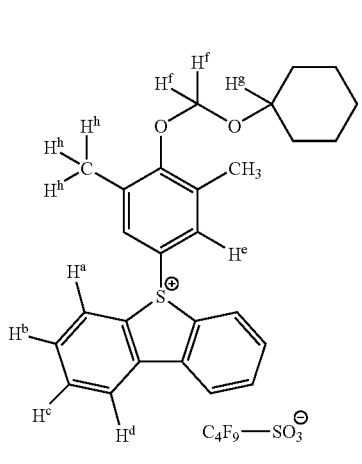

[Chemical Formula 85]

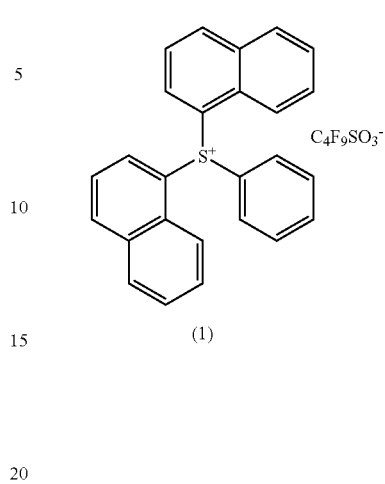

Examples 11-12

Comparative Examples 2-3 and Reference Examples 1-3

<Evaluation of Solubility>

With respect to a compound (1) represented by chemical formula (1) shown below, a compound (2) represented by chemical formula (2) shown below, the aforementioned compounds (3) to (5), the aforementioned compound (b1-91) and the aforementioned compound (b1-100), the solubility was evaluated as follows.

With respect to each of the compounds, propylene glycol monomethyl ether acetate (PGMEA) solutions, propylene glycol monomethyl ether (PGME) solutions and ethyl lactate (EL) solutions of various concentrations were prepared. The prepared solutions were stirred to evaluate the concentration at which the acid generator was completely dissolved. The results are shown in Table 8.

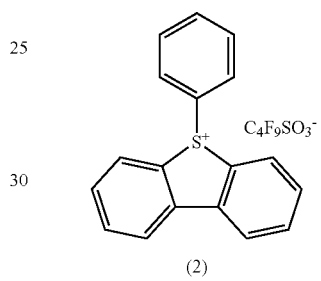

It was confirmed that the solubility of the compounds (b1-91) and (b1-100) according to the present invention in PGMEA, PGME and EL (which are typical resist solvents) was significantly superior to the compounds (1) to (5).

Example 13 and Reference Examples 4 to 7

Preparation of Positive Resist Composition Solution

The components shown in Table 9 were mixed together and dissolved to obtain positive resist composition solutions.

TABLE 8

|  | Ex. 11 | Ex. 12 | Comp. Ex. 2 | Comp. Ex. 3 | Ref. Ex. 1 | Ref. Ex. 2 | Ref. Ex. 3 |
|---|---|---|---|---|---|---|---|
| Compound | b1-91 | b1-100 | (1) | (2) | (3) | (4) | (5) |
| Solubility in PGMEA (% by weight) | >30 | >30 | <2.0 | 10~15 | 0.6 | 5~10 | 10.0 |
| Solubility in PGME (% by weight) | >30 | >30 | 5.0 | 20.0 | 10~15 | 20.0 | 20.0 |
| Solubility in EL (% by weight) | >30 | >30 | 5.0 | 20.0 | 10~15 | 15~20 | 20.0 |

TABLE 9

|  | Component (A) | Component (B) | Component (D) | Component (E) | Component (S) | |
|---|---|---|---|---|---|---|
| Ex. 13 | (A)-1 | (B)-1' | (D)-1 | (E)-1 | (S)-1 | (S)-2 |
|  | [100] | [15.08] | [0.54] | [1.32] | [2000] | [10] |
| Ref. Ex. 4 | (A)-1 | (B)-2' | (D)-1 | (E)-1 | (S)-1 | (S)-2 |
|  | [100] | [11.00] | [0.54] | [1.32] | [2000] | [10] |

TABLE 9-continued

|  | Component (A) | Component (B) | Component (D) | Component (E) | Component (S) | |
|---|---|---|---|---|---|---|
| Ref. Ex. 5 | (A)-1 | (B)-3' | (D)-1 | (E)-1 | (S)-1 | (S)-2 |
|  | [100] | [11.86] | [0.54] | [1.32] | [2000] | [10] |
| Ref. Ex. 6 | (A)-1 | (B)-4' | (D)-1 | (E)-1 | (S)-1 | (S)-2 |
|  | [100] | [12.14] | [0.54] | [1.32] | [2000] | [10] |
| Ref. Ex. 7 | (A)-1 | (B)-5' | (D)-1 | (E)-1 | (S)-1 | (S)-2 |
|  | [100] | [13.82] | [0.54] | [1.32] | [2000] | [10] |

In Table 9, the reference characters indicate the following. Further, the values in brackets [ ] indicate the amount (in terms of parts by weight) of the component added.

(A)-1: a polymer represented by chemical formula (A)-1 above (B)-1': an acid generator represented by chemical formula (b1-91) above (compound of Example 9)

(B)-2': an acid generator represented by chemical formula (2) above (B)-3': an acid generator represented by chemical formula (3) above (compound of Synthesis Example 3)

(B)-4': an acid generator represented by chemical formula (4) above (compound of Synthesis Example 4) (B)-5': an acid generator represented by chemical formula (5) above (compound of Synthesis Example 5)

(D)-1: tri-n-pentylamine (E)-1: salicylic acid (S)-1: a mixed solvent of PGMEA/PGME=6/4 (weight ratio)

(S)-2: γ-butyrolactone

The molar amounts of (B)-1' to (B)-5' are the same.

<Evaluation of Lithography Properties>

Using the obtained positive resist composition solutions, resist patterns were formed, and the following lithography properties were evaluated.

[Resolution Sensitivity]

An organic antireflection film was formed on an 8-inch silicon wafer in the same manner as in Example 2 and Comparative Example 1, and a resist film having a film thickness of 120 nm was formed on the organic antireflection film in substantially the same manner as in Example 2 and Comparative Example 1, except that the PAB temperature was changed to 110° C.

Subsequently, a line and space (1:1) resist pattern (L/S pattern) was formed in substantially the same manner as in Example 2 and Comparative Example 1, except that the PEB temperature was changed to 110° C., and a 6% halftone mask pattern was used. In this manner, the optimum exposure dose (sensitivity: Eop, mJ/cm$^2$) for forming a L/S pattern having a line width of 120 nm and a pitch of 240 nm was determined.

The results are shown in Table 10.

[Evaluation of Exposure Margin (EL Margin)]

L/S patterns with a target dimension of a line width of 120 nm and a pitch of 240 nm were formed by changing the exposure dose.

The exposure dose with which a L/S (1:1) pattern having a dimension of the target dimension (120 nm) ±5% (i.e., 114 to 126 nm) was determined, and the EL margin (unit: %) was determined by the following formula:

$$EL\ margin\ (\%) = (|E1 - E2|/Eop) \times 100$$

wherein E1 represents the exposure dose (mJ/cm$^2$) for forming a L/S pattern having a line width of 126 nm, and E2 represents the exposure dose (mJ/cm$^2$) for forming a L/S pattern having a line width of 114 nm.

The larger the value of EL margin, the smaller the fluctuation in the pattern size accompanied by the variation in the exposure dose.

As a result, it was found that the pattern formed by using the resist composition of Example 13 exhibited an EL margin value larger than the other patterns formed by using the resist compositions of Reference Examples 4 to 7. The results are shown in Table 10.

TABLE 10

|  | Ex. 13 | Ref. Ex. 4 | Ref. Ex. 5 | Ref. Ex. 6 | Ref. Ex. 7 |
|---|---|---|---|---|---|
| Eop (mJ/cm$^2$) | 64.0 | 55.0 | 59.5 | 65.5 | 92.0 |
| EL (%) | 8.15 | 7.63 | 7.14 | 6.67 | 7.81 |

[Pattern Shape]

The cross-sectional shape of the resist patterns was observed by a scanning electron microscope (product name: S-4700; manufactured by Hitachi, Ltd.). As a result, it was found that the shape of the resist pattern of Example 13 was superior to the resist patterns of Reference Examples 4 to 7 in that no necking on the side walls of the resist pattern was observed, and the perpendicularity and rectangularity were high. Further, generation of defects on the resist pattern surface was suppressed.

Examples 14-15 and Comparative Example 4

Preparation of Positive Resist Composition Solution

The components shown in Table 11 were mixed together and dissolved to obtain positive resist composition solutions.

TABLE 11

|  | Component (A) | Component (B) | | Component (D) | Component (S) |
|---|---|---|---|---|---|
| Ex. 14 | (A)-2 | (B)-1 | (B)-7 | (D)-1 | (S)-1 |
|  | [100] | [10.97] | [4.00] | [0.1] | [2200] |
| Ex. 15 | (A)-2 | (B)-6 | (B)-7 | (D)-1 | (S)-1 |
|  | [100] | [10.22] | [4.00] | [0.1] | [2200] |
| Comp. Ex. 4 | (A)-2 | (B)-8 | | (D)-1 | (S)-1 |
|  | [100] | [4.94] | | [0.1] | [2200] |

In Table 11, the reference characters indicate the following. Further, the values in brackets [ ] indicate the amount (in terms of parts by weight) of the component added.

(A)-2': a polymer represented by chemical formula (A)-2' shown below (B)-1': an acid generator represented by chemical formula (b1-91) shown above (compound of Example 9)

(B)-6: an acid generator represented by chemical formula (b1-100) shown above (compound of Example 10)

(B)-7: triphenylsulfonium heptafluoro-n-propane sulfonate (B)-8: tripehnylsulfonium nonafluoro-n-butane sulfonate (D)-1: tri-n-pentylamine (S)-1: a mixed solvent of PGMEA/PGME=6/4 (weight ratio)

[Chemical Formula 86]

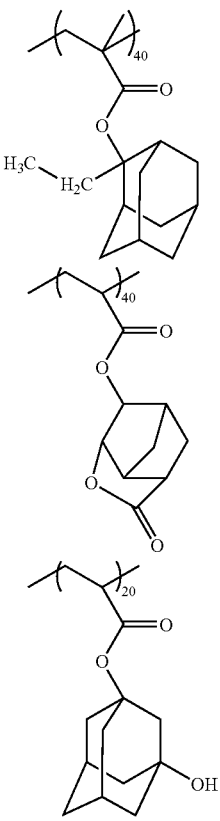

(A)-2'

[Mw=7,000, Mw/Mn=2.0]

The polymer (A)-2' was synthesized by a conventional dropwise polymerization method using monomers which derive the respective structural units. In chemical formula (A)-2', the subscript numerals on the brackets indicate the percentage (mol %) of the respective structural units within the copolymer. The compositional ratio was determined by $^{13}$C-NMR. Further, Mw and Mw/Mn were determined by the polystyrene equivalent value as measured by gel permeation chromatography (GPC).

<Evaluation of Lithography Properties>

Using the obtained positive resist composition solutions, resist patterns were formed, and the following lithography properties were evaluated.

[Resolution·Sensitivity]

An organic anti-reflection film composition (product name: ARC-29A, manufactured by Brewer Science Ltd.) was applied onto an 8-inch silicon wafer using a spinner, and the composition was then baked at 205° C. for 60 seconds, thereby forming an organic anti-reflection film having a film thickness of 89 nm. Then, the positive resist composition solution obtained above was applied onto the anti-reflection film using a spinner, and was then prebaked (PAB) on a hotplate at 110° C. for 60 seconds and dried, thereby forming a resist film having a film thickness of 120 nm.

Subsequently, the resist film was selectively irradiated with an ArF excimer laser (193 nm) through a mask pattern, using an ArF exposure apparatus NSR-S609B (manufactured by Nikon Corporation, NA (numerical aperture)=1.07, 2/3 annular illumination). Thereafter, a post exposure bake (PEB) treatment was conducted at 110° C. for 60 seconds, followed by development for 30 seconds at 23° C. in a 2.38% by weight aqueous solution of tetramethylammonium hydroxide. Then, the resist was washed for 30 seconds with pure water, followed by drying by shaking, thereby forming a contact hole pattern (C/H pattern) having a hole diameter of 75 nm and a pitch of 131 nm. The optimum exposure dose (sensitivity: Bop, mJ/cm$^2$) for forming the contact pattern was determined. As a result, it was found that the Eop was 50 mJ/cm$^2$ in Example 14, 49 mJ/cm$^2$ in Example 15, and 34 mJ/cm$^2$ in Comparative Example 4.

[Pattern Shape]

The C/H pattern having a hole diameter of 75 nm and a pitch of 131 nm was observed by a scanning electron microscope (product name: S-9220, manufactured by Hitachi, Ltd.). As a result, it was found that the removability (ability to allow substantially equivalent holes to be formed) of the C/H patterns formed in Examples 14 and 15 was superior to the C/H pattern formed in Comparative Example 4. Further, with respect to the C/H pattern formed in Comparative Example 4, it was confirmed that some portions of the resist film were not completely removed from the holes (substantially equivalent holes could not be formed).

From the results shown above, it was confirmed that by using the resist composition of the present invention, excellent lithography properties can be achieved.

The invention claimed is:

1. A resist composition comprising a base component (A) which exhibits changed solubility in an alkali developing solution under action of acid and an acid-generator component (B) which generates acid upon irradiation, said acid-generator component (B) comprising an acid generator (B1) comprised of a compound represented by general formula (b1-8) shown below or an acid generator (B1') comprised of a compound represented by general formula (b1-9) shown below:

[Chemical Formula 1]

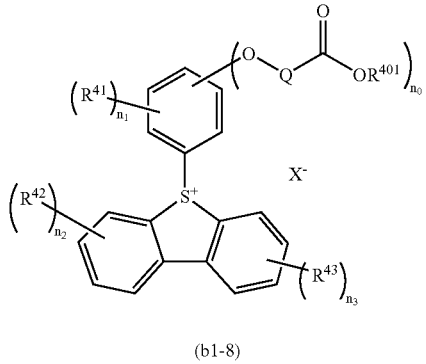

(b1-8)

wherein R$^{401}$ represents an acid dissociable, dissolution inhibiting group; R$^{41}$ to R$^{43}$ each independently represents a halogen atom, a halogenated alkyl group, an alkyl group, an acetyl group, an alkoxy group, a carboxy group or a hydroxyalkyl group; Q represents a divalent linking group or a single bond; n$_0$ represents an integer of 1 to 3, and n$_1$ to n$_3$ each independently represents an integer of 0 to 3, with the proviso that n$_0$+n$_1$ is 5 or less; and X$^-$ represents an anion;

[Chemical Formula 2]

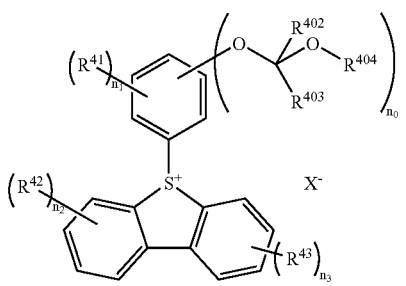

(b1-9)

wherein $R^{41}$ to $R^{43}$ each independently represents a halogen atom, a halogenated alkyl group, an alkyl group, an acetyl group, an alkoxy group, a carboxy group or a hydroxyalkyl group; $R^{402}$ and $R^{403}$ each independently represents a hydrogen atom, an alkyl group or a halogenated alkyl group; $R^{404}$ represents an alkyl group or a halogenated alkyl group, wherein $R^{403}$ and $R^{404}$ may be bonded to each other to form a ring structure; $n_0$ represents an integer of 1 to 3, and $n_1$ to $n_3$ each independently represents an integer of 0 to 3, with the proviso that $n_0+n_1$ is 5 or less; and $X^-$ represents an anion.

2. The resist composition according to claim 1, wherein $R^{401}$ in general formula (b1-8) is an acid dissociable, dissolution inhibiting group represented by general formula (b1-8-0) shown below:

[Chemical Formula 3]

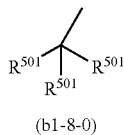

(b1-8-0)

wherein the plurality of $R^{501}$ may be the same or different, and at least one $R^{501}$ represents a linear or branched alkyl group of 1 to 4 carbon atoms; and the remaining two $R^{501}$ each independently represents a linear or branched alkyl group of 1 to 4 carbon atoms or a monovalent aliphatic cyclic group of 4 to 20 carbon atoms, or the remaining two $R^{501}$ may be bonded to each other to form a divalent aliphatic cyclic group of 4 to 20 carbon atoms including the carbon atom to which the two $R^{501}$ are bonded.

3. The resist composition according to claim 1, wherein $R^{404}$ in general formula (b1-9) is a cyclic alkyl group.

4. The resist composition according to claim 1, wherein said base component (A) is a base component which exhibits increased solubility in an alkali developing solution under action of acid.

5. The resist composition according to claim 4, wherein said base component (A) is a resin component (A1), and has a structural unit (a1) derived from an acrylate ester containing an acid dissociable, dissolution inhibiting group.

6. The resist composition according to claim 5, wherein said base component (A) further has a structural unit (a2) derived from an acrylate ester having a lactone-containing cyclic group.

7. The resist composition according to claim 5, wherein said base component (A) further has a structural unit (a3) derived from an acrylate ester having a polar group-containing aliphatic hydrocarbon group.

8. The resist composition according to claim 1, which further comprises a nitrogen-containing organic compound (D).

9. A method of forming a resist pattern, comprising: applying a resist composition of any one of claims 1 to 8 to a substrate to form a resist film on the substrate; conducting exposure of said resist film; and alkali-developing said resist film to form a resist pattern.

10. A compound represented by general formula (b1-8) shown below:

[Chemical Formula 4]

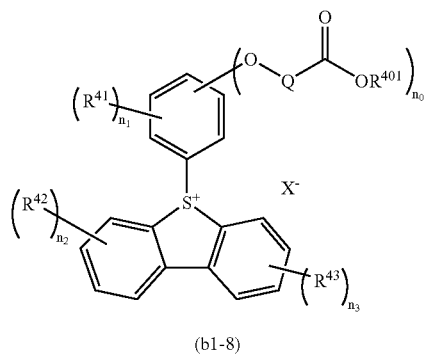

(b1-8)

wherein $R^{401}$ represents an acid dissociable, dissolution inhibiting group; $R^{41}$ to $R^{43}$ each independently represents a halogen atom, a halogenated alkyl group, an alkyl group, an acetyl group, an alkoxy group, a carboxy group or a hydroxyalkyl group; Q represents a divalent linking group or a single bond; $n_0$ represents an integer of 1 to 3, and $n_1$ to $n_3$ each independently represents an integer of 0 to 3, with the proviso that $n_0+n_1$ is 5 or less; and $X^-$ represents an anion.

11. The compound according to claim 10, wherein $R^{401}$ is an acid dissociable, dissolution inhibiting group represented by general formula (b1-8-0) shown below:

[Chemical Formula 5]

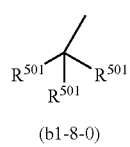

(b1-8-0)

wherein the plurality of $R^{501}$ may be the same or different, and at least one $R^{501}$ represents a linear or branched alkyl group of 1 to 4 carbon atoms; and the remaining two $R^{501}$ each independently represents a linear or branched alkyl group of 1 to 4 carbon atoms or a monovalent aliphatic cyclic group of 4 to 20 carbon atoms, or the remaining two $R^{501}$ may be bonded to each other to form a divalent aliphatic cyclic group of 4 to 20 carbon atoms including the carbon atom to which the two $R^{501}$ are bonded.

12. An acid generator comprising a compound of claim 10 or 11.

13. A compound represented by general formula (b1-9) shown below:

[Chemical Formula 6]

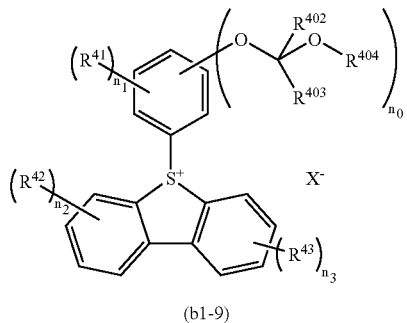

(b1-9)

wherein $R^{41}$ to $R^{43}$ each independently represents a halogen atom, a halogenated alkyl group, an alkyl group, an acetyl group, an alkoxy group, a carboxy group or a hydroxyalkyl group; $R^{402}$ and $R^{403}$ each independently represents a hydrogen atom, an alkyl group or a halogenated alkyl group; $R^{404}$ represents an alkyl group or a halogenated alkyl group, wherein $R^{403}$ and $R^{404}$ may be bonded to each other to form a ring structure; $n_0$ represents an integer of 1 to 3, and $n_1$ to $n_3$ each independently represents an integer of 0 to 3, with the proviso that $n_0+n_1$ is 5 or less; and $X^-$ represents an anion.

14. The compound according to claim 13, wherein $R^{404}$ is a cyclic alkyl group.

15. An acid generator comprising a compound of claim 13 or 14.

* * * * *

UNITED STATES PATENT AND TRADEMARK OFFICE
CERTIFICATE OF CORRECTION

PATENT NO. : 7,488,568 B2  Page 1 of 1
APPLICATION NO. : 12/060695
DATED : February 10, 2009
INVENTOR(S) : Iwai et al.

It is certified that error appears in the above-identified patent and that said Letters Patent is hereby corrected as shown below:

On the cover page, item (30) Foreign Application Priority Data, insert

-- JAPAN 2007-101926 04/09/2007

JAPAN 2007-135427 05/22/2007

JAPAN 2007-306388 11/27/2007 --

Signed and Sealed this

Second Day of June, 2009

JOHN DOLL
*Acting Director of the United States Patent and Trademark Office*